US008961917B2

(12) United States Patent
Gore et al.

(10) Patent No.: US 8,961,917 B2
(45) Date of Patent: Feb. 24, 2015

(54) LANTHANUM CARBONATE HYDROXIDE, LANTHANUM OXYCARBONATE AND METHODS OF THEIR MANUFACTURE AND USE

(75) Inventors: Ashok Yeshwant Gore, Tustin, CA (US); Edward A. Schauer, Sparks, NV (US); Matthew Stewart, Reno, NV (US); Ramsharan Singh, Irvine, CA (US)

(73) Assignee: Spectrum Pharmaceuticals, Inc., Irvine, CA (US)

( * ) Notice: Subject to any disclaimer, the term of this patent is extended or adjusted under 35 U.S.C. 154(b) by 533 days.

(21) Appl. No.: 13/106,637

(22) Filed: May 12, 2011

(65) Prior Publication Data

US 2011/0280956 A1 Nov. 17, 2011

Related U.S. Application Data

(60) Provisional application No. 61/333,887, filed on May 12, 2010.

(51) Int. Cl.
*C01B 15/10* (2006.01)
*A61K 33/24* (2006.01)
(Continued)

(52) U.S. Cl.
CPC ............... *A61K 33/24* (2013.01); *A61K 9/0056* (2013.01); *A61K 9/0095* (2013.01); *A61K 9/10* (2013.01); *A61K 9/1623* (2013.01); *A61K 9/1652* (2013.01); *A61K 9/2018* (2013.01); *A61K 9/2027* (2013.01); *A61K 9/205* (2013.01); *A61K 9/2054* (2013.01); *A61K 9/2068* (2013.01); *C01F 17/005* (2013.01); *A61K 9/4866* (2013.01); *C01P 2002/72* (2013.01); *C01P 2004/03* (2013.01); *C01P 2004/61* (2013.01); *C01P 2006/10* (2013.01); *C01P 2006/11* (2013.01); *C01P 2006/12* (2013.01); *C01P 2006/80* (2013.01)
USPC .......................................................... 423/263

(58) Field of Classification Search
USPC .......................................................... 423/263
See application file for complete search history.

(56) References Cited

U.S. PATENT DOCUMENTS

| | | | |
|---|---|---|---|
| 3,692,671 | A | 9/1972 | Recht |
| 3,768,989 | A | 10/1973 | Goetzinger et al. |

(Continued)

FOREIGN PATENT DOCUMENTS

| | | | |
|---|---|---|---|
| AU | 601998 | B2 | 9/1990 |
| CN | 1184428 | A | 6/1998 |

(Continued)

OTHER PUBLICATIONS

European Examination Report for Application No. EP 10151585.6 dated Aug. 31, 2012.

(Continued)

*Primary Examiner* — Richard M Rump
(74) *Attorney, Agent, or Firm* — Lerner, David, Littenberg, Krumholz & Mentlik, LLP

(57) ABSTRACT

The present invention is a method of producing a lanthanum carbonate hydroxide or lanthanum oxycarbonate which has improved properties. The method involves the use of a water soluble lanthanum and a water soluble non-alkali metal carbonate or bicarbonate. The resulting material can be used as a phosphate binder individually or for treating patients with hyperphosphatemia.

7 Claims, 23 Drawing Sheets

Batch 100808

Batch 100908

(51) Int. Cl.

| | |
|---|---|
| ***A61K 9/00*** | (2006.01) |
| ***A61K 9/10*** | (2006.01) |
| ***A61K 9/16*** | (2006.01) |
| ***A61K 9/20*** | (2006.01) |
| ***C01F 17/00*** | (2006.01) |
| *A61K 9/48* | (2006.01) |

(56) References Cited

U.S. PATENT DOCUMENTS

| | | | | |
|---|---|---|---|---|
| 3,922,331 | A | 11/1975 | MacDonald et al. | |
| 3,922,333 | A | 11/1975 | Mazdiyasni et al. | |
| 4,240,048 | A | 12/1980 | Zumsteg | |
| 4,454,162 | A | 6/1984 | Schanze | |
| 4,462,970 | A | 7/1984 | Pastor et al. | |
| 4,497,785 | A | 2/1985 | Tilley et al. | |
| 4,919,902 | A | 4/1990 | Bricker et al. | |
| 4,929,787 | A | 5/1990 | Cameron et al. | |
| 5,061,670 | A | 10/1991 | Forquy et al. | |
| 5,407,560 | A | 4/1995 | Miyawaki et al. | |
| 5,539,000 | A | 7/1996 | Leonard | |
| 5,683,953 | A | 11/1997 | Mills | |
| 5,782,792 | A | 7/1998 | Jones et al. | |
| 5,843,477 | A | 12/1998 | Alexander | |
| 5,968,976 | A | 10/1999 | Murrer et al. | |
| 6,146,539 | A | 11/2000 | Mills | |
| 6,197,201 | B1 | 3/2001 | Misra et al. | |
| 6,312,604 | B1 | 11/2001 | Denkewicz, Jr. et al. | |
| 6,322,895 | B1 | 11/2001 | Canham | |
| 6,338,800 | B1 | 1/2002 | Kulperger et al. | |
| 6,376,479 | B1 | 4/2002 | Knutson et al. | |
| 6,403,523 | B1 | 6/2002 | Cantrell et al. | |
| 6,521,647 | B2 | 2/2003 | Foster | |
| 6,849,609 | B2 | 2/2005 | Morrison | |
| 6,858,203 | B2 | 2/2005 | Holmes-Farley et al. | |
| 7,078,059 | B2 | 7/2006 | Atherton et al. | |
| 7,119,120 | B2 | 10/2006 | Jozefiak et al. | |
| 7,381,428 | B2 | 6/2008 | Ferdinando et al. | |
| 7,465,465 | B2 | 12/2008 | Haslam et al. | |
| 7,588,782 | B2 | 9/2009 | Moerck et al. | |
| 2002/0035151 | A1 | 3/2002 | DeLuca | |
| 2003/0133902 | A1 | 7/2003 | Holmes-Farley et al. | |
| 2003/0235616 | A1 | 12/2003 | Sowden et al. | |
| 2004/0161474 | A1 | 8/2004 | Moerck et al. | |
| 2005/0079135 | A1 | 4/2005 | Haslam et al. | |
| 2005/0131138 | A1 | 6/2005 | Connor et al. | |
| 2005/0247628 | A1 | 11/2005 | Moerck et al. | |
| 2006/0002837 | A1 | 1/2006 | Moerck et al. | |
| 2006/0003018 | A1* | 1/2006 | Moerck et al. | 424/617 |
| 2006/0083791 | A1 | 4/2006 | Moerck et al. | |
| 2006/0134225 | A1 | 6/2006 | Moerck et al. | |
| 2006/0153932 | A1 | 7/2006 | Ferdinando et al. | |
| 2006/0252907 | A1 | 11/2006 | Shigematsu et al. | |
| 2007/0149405 | A1 | 6/2007 | Spitler | |
| 2007/0259052 | A1 | 11/2007 | Hallenbeck et al. | |
| 2008/0058250 | A1 | 3/2008 | Wren et al. | |
| 2008/0069860 | A1 | 3/2008 | Wren et al. | |
| 2008/0089948 | A1* | 4/2008 | Hallenbeck et al. | 424/617 |
| 2008/0226735 | A1 | 9/2008 | Moerck et al. | |
| 2010/0196485 | A1 | 8/2010 | Moerck et al. | |
| 2011/0123628 | A1 | 5/2011 | Moerck et al. | |

FOREIGN PATENT DOCUMENTS

| | | | |
|---|---|---|---|
| CN | 1557982 | A | 12/2004 |
| CN | 1688511 | A | 10/2005 |
| CN | 101484798 | A | 7/2009 |
| EP | 0604919 | A1 | 7/1994 |
| EP | 1698233 | A1 | 9/2006 |
| JP | 60-206448 | A | 10/1985 |
| JP | 60-226414 | A | 11/1985 |
| JP | 61004529 | A | 1/1986 |
| JP | 08010610 | A | 1/1996 |
| JP | 9-315865 | A | 12/1997 |
| JP | 11-047765 | A | 2/1999 |
| JP | 2002-018421 | A | 1/2002 |
| WO | 9630029 | A1 | 10/1996 |
| WO | 9915189 | A1 | 4/1999 |
| WO | 0200227 | A2 | 1/2002 |
| WO | 02/22258 | | 3/2002 |
| WO | 0222258 | A2 | 3/2002 |
| WO | 02060818 | A1 | 8/2002 |
| WO | 03088976 | A1 | 10/2003 |
| WO | 03094933 | A2 | 11/2003 |
| WO | 2004016553 | A2 | 2/2004 |
| WO | 2004050558 | B1 | 9/2004 |
| WO | 2005018651 | A1 | 3/2005 |
| WO | 2005042617 | A1 | 5/2005 |
| WO | 2005049084 | A2 | 6/2005 |
| WO | 2006015055 | A1 | 2/2006 |
| WO | 2006044657 | A2 | 4/2006 |
| WO | 2006050314 | A2 | 5/2006 |
| WO | 2007022466 | A2 | 2/2007 |
| WO | 2007130721 | A2 | 11/2007 |

OTHER PUBLICATIONS

Office Action from Brazil Application No. PI313737-6 dated Jun. 21, 2011.

Office Action from Canada Application No. 2,494,992 dated Apr. 29, 2010.

Office Action from corresponding Canadian Application No. 2,494,992 dated Dec. 19, 2011.

Office Action from Israel Application No. 166803 dated Feb. 1, 2010.

Office Action from Israel Application No. 166803 dated May 23, 2011.

Office Action from Israel Application No. 166803 dated Sep. 19, 2012.

Office Action from U.S. Appl. No. 12/643,059 mailed Jun. 12, 2012.

Office Action from U.S. Appl. No. 13/229,157 mailed Jul. 31, 2012.

Canadian Office Action for Application No. 2,494,992 dated Nov. 21, 2012.

Office Action from U.S. Appl. No. 13/229,157 mailed Dec. 29, 2011.

Office Action from U.S. Appl. No. 13/018,894 mailed Jun. 13, 2011.

Office Action from U.S. Appl. No. 12/643,059 mailed Jun. 28, 2011.

Fiddler, G. et al. (Apr. 2003). Lanthanum Carbonate has a Good Safety Profile Following Concomifanf Adminisfrafion wifh Mefoprolol and has No Clinically Significanf Effecf on ifs Pharmacokinetics, Poster presented at the National Kidney Foundation Clinical Meeting, Dallas, Texas, Apr. 2-6, 2003, 1 page.

Fiddler, G. et al. (Apr. 2003). "Lanthanum Carbonate has No Effect on the Pharmacokientics of Digoxin and Can be Adminisfered Safely in Combinafion," Posfer presenfed of fhe Nafional Kidney Foundation Clinical Meeting, Dallas, Texas, Apr. 2-6, 2003, 1 page.

Finn, W. et al. (Apr. 2003). 'Efficacy and Safety of Long-Term Treatment with Lanthanum Carbonafe—A Novel Phosphafe-Binding Agenf,' Posfer presented af fhe National Kidney Foundation Clinical Meeting, Dallas, Texas, Apr. 2-6, 2003, 1 page.

Finn, W. F. et al. (Sep. 1999). Resulfs of a Randomized Dose-Ranging, Placebo Controlled Study of Lanthanum Carbonate for Reduction of Serum Phosphate in Chronic Renal Failure Pafienfs Receiving Hemodialysis, Journal of the American Society of Nephrology, 32nd Annual Meefing and 1999 Renal Week, Nov. 1-8, 1999, Miami Beach, Florida, 10:261A, Abstract No. A1317.

Graff, L. et al. (Sep. 1995). A Possible Non-Aluminum Oral Phosphafe Binder? A Comparative Study on Dietary Phosphorus Absorption, Research Communications in Molecular Pathology and Pharmacology 69(3)373-388.

Joy, M. S. et al. (Sep. 2002). FosrenolTM, a Novel, Non-Aluminum, Non-Calcium Phosphate Binder, has a Good Safety and Efficacy Profile in the Long-Term Treatment of Hyperphosphatemia in Hemodialysis Patients, Journal of the American Society of Nephrology, Oct. 30-Nov. 4, 2002, Philadelphia, Pennsylvania, 1 3:386A, Abstract No. SA-P0600.

Joy, M. S. et al., 'Results of a Randomized, Phase III, Dose-Titration, Parallel Croup Sfudy of Lanthanum Carbonafe for Reduction and Mainfenance of Serum Phosphafe in Chronic Hemodialysis Patients,' Journal of the American Society of Nephrology, 10; 2:388A (1999), Abstract No. A1996.

(56) References Cited

OTHER PUBLICATIONS

Larson, E. A. et al. (1986). Phosphate Binding Gels: Balancing Phosphate Adsorption and Aluminum Toxicity, Kidney International29:1 131-11350. (Abstracf only obtained from Medline, 86308884, 1 page).
Rudnic, E. R. et al. (1990). Oral Solid Dosage Forms, Chapter 89 in Remingfon: Pharmaceutical Sciences. 18th Edition, pp. 1633-1658.
Stewart, J. ef al. (Sep. 2002). Adminisfrafion of a Novel Phosphafe Binder, FosrenolJM, with Food is Associated with Good Tolerabilify and Low Systemic Absorption, Journal of the American Society of Nephrology, Oct. 30-Nov. 4, 2002, Philadelphia, Pennsylvania, 13:386A, Abstracf No. SA-P0601.
U.S. Office Action mailed May 12, 2008, for U.S. Appl. No. 11/181,650, filed Jul. 13, 2005, 1 0 pages.
U.S. Office Action mailed Dec. 4, 2007, for U.S. Appl. No. 10/444,774, filed May 23, 2003, 9 pages.
U.S. Office Acfion mailed Sep. 8, 2006, for U.S. Appl. No. 10/444,774, filed May 23, 2003, 8 pages.
Medline abstract 86308884 (1986).
Yamaguchi et al., Abstract for "Formation and Decomposition of Lanthanum Monoxocarbonate," Zeitschrift fuer Anorganiche und Allgemeine Chemie, 514, 1984, pp. 205-212, obtained from Chemabs "Online", Chemical Abstracts Service, Columbus OH; 1 pg.
Holsa et al., Abstract for "Preparation, Thermal Stability and Luminescence Properties of Selected Rare Earth Oxycarbonates," Thermochimica Acta, 190(2), pp. 335-343, 1991, Chemabs "Online", Chemical Abstracts Service, Columbus, OH; 1 pg.
Olafsen et al., Abstract for "Synthesis of Rare Earth Oxide Carbonates and Thermal Stability of Nd202C03 II," Journal of Materials Chemistry, 9(10), 1999, pp. 2697-2702, obtained from Database Chemabs "Online," Chemical Abstracts Service, Columbus,OH, 1 pg.
Behets et al., "An Assessment of the Effects of Lanthanum on Bone in a Chronic Renal Failure (CFR) Rat Model," Journal of the American Society of Nephrology, Miami, FL; Nov. 1999.
Behets et al., "Effects of the Phosphate Binder Renagel.RTM. (Sevelamer) on Biochemical Parameters and Bone Histology in a Chronic Renal Failure (CRF) Rat Model," Journal of the American Society of Nephrology, Miami, FL; Nov. 1999.
DeBroe et al., "Lanthanum Carbonate (Fosrenol.TM.), A New Agent in the Treatment of Hyperphosphatemia in End-State Renal Failure," University Hospital of Antwerp, Belgium, 2002.
Shire Pharmaceutical Development Ltd., Programme for "New Directions in the Treatment of Hyperphosphatemia," European Renal Association Conference, Jul. 14, 2002, Copenhagen, Denmark.
Damment et al., "Bone Mineralisation Defect with High Doses of Phosphate Binders in Uraemic Rats—An Artefact of Phosphate Depletion?," European Renal Association Conference, Jul. 14, 2002, Copenhagen, Denmark.
Sack et al., "Fosrenal.TM. (Lanthanum Carbonate) is Well Tolerated in Patients Requiring Hemodialysis: Results of a Phase I Clinical Trial," ASN 35.sup.th Annual Meeting & Scientific Exposition, Nov. 2002, Philadelphia, PA.
Hutchison, A.J., "The Novel, Non-Aluminum, Non-Calcium Phosphate Binder, Lanthanum Carbonate (Fosrenol.TM.), is an Effective Treatment for Hyperphosphatemia and has a Good Safety Profile," ASN 35.sup.th Annual Meeting & Scientific Exposition, Nov. 2002, Philadelphia, PA.
Finn et al., "Fosrenol.TM., a Novel, Non-Calcium, Non-Aluminum Phosphate Binder, Has a Good Safety and Efficacy Profile in the Long-Term Treatment of Hyperphosphatemia in Hemodialysis Patients," ASN 35.sup.th Annual Meeting & Scientific Exposition, Nov. 2002.
D'Haese et al., "The Effects of Lanthanum Carbonate (Fosrenol.TM.) and Calcium Carbonate on Renal Bone Disease in Dialysis Patients," National Kidney Foundation Clinical Meeting, Apr. 2003, Dallas, TX.
Hutchison et al., "Safety and Efficacy of Lanthanum Carbonate for Treatment of Hyperphosphatemia in Haemodialysis Patients over 12 months," National Kidney Foundation Clinical Meeting, Apr. 2003, Dallas, TX.
Fiddler et al., "Lanthanum Carbonate is Well Tolerated When Administered with Warfarin and Has No Effect on its Pharmacokinetics," National Kidney Foundation Clinical Meeting, Apr. 2003, Dallas, TX.
Hutchinson et al., "Safety, Tolerability and Efficacy of Lanthanum Carbonate in Haemodialysis Patients: a 12-Month Study," ERA-EDTA World Congress of Nephrology, Jun. 2003, Berlin, Germany.
Dictionary of Chemistry and Chemical Technology. (1999). p. 2240-2242. (English translation attached, 13 pages).
European Search Report mailed Aug. 16, 2006, for EP 06000002.3 filed Aug. 8, 2003, 10 pages.
International Preliminary Examination Report mailed Jan. 3, 2005, PCT Application No. PCT/US03/25192 filed Aug. 8, 2003, 7 pages.
International Search Report and Written Opinion mailed Jul. 20, 2007, for PCT Application No. PCT/US06/32415 filed Aug. 17, 2006, 8 pages.
International Search Report and Written Opinion mailed Jun. 3, 2008, for PCT Application No. PCT/US06/32492 filed Aug. 17, 2006, 8 pages.
International Search Report and Written Opinion mailed Mar. 21, 2008, for PCT Application No. PCT/US05/37015 filed Oct. 13, 2005, 16 pages.
International Search Report mailed Jun. 1, 2004, for PCT Application No. PCT/US03/38235 filed Dec. 2, 2003, 6 pages.
International Search Report mailed Jun. 7, 2004, for PCT Application No. PCT/US03/25192 filed Aug. 8, 2003, 11 pages.
International Written Opinion mailed Mar. 21, 2005, PCT Application No. PCT/US03/38235 filed Dec. 2, 2003, 5 pages.
Joy, M. S. et al. (2003). "Randomized, Double-Blind, Placebo-Controlled, Dose Titration, Phase III Study Assessing Efficacy and Tolerability of Lanthanum Carbonate: A New Phosphate Binder for the Treatment of Hyperphosphatemia," American Journal ofKidney Diseases 42:96-107. (Abstract only obtained from Chemical Abstracts HCAplus, 2003:602063, 1 page).
Nagashima, K. et al. (Jan. 1973). "The Synthesis of Crystalline Rare Earth Carbonates," Bulletin of the Chemical Society of Japan 46(1):152-156.
Olafsen, A. et al. (2001). "On the Crystal Structure of Ln.sub.2O.sub.2CO.sub.3 II (Ln=La and Nd)," Journal of Solid State Chemistry 158:14-24 (Abstract only obtained from Chemical Abstracts HCAplus, 2001:260955, 1 pages).
Partial European Search Report mailed Apr. 18, 2006, for EP 06000002.3 filed Aug. 8, 2003, 7 pages.
U.S. Office Action mailed Feb. 16, 2006, for U.S. Appl. No. 10/444,774, filed May 23, 2003, 7 pages.
U.S. Office Action mailed May 25, 2007, for U.S. Appl. No. 10/444,774, filed May 23, 2003, 10 pages.
U.S. Office Action mailed Sep. 17, 2008, for U.S. Appl. No. 11/181,609, filed Jul. 13, 2005, 6 pages.
U.S. Office Action mailed Sep. 8, 2006, for U.S. Appl. No. 10/444,774, filed May 23, 2003, 8 pages.
U.S. Appl. No. 11/576,785, filed Apr. 5, 2007 for Moerck et al.
U.S. Appl. No. 12/051,726, filed Mar. 19, 2008 for Moerck et al.
U.S. Appl. No. 12/197,157, filed Aug. 22, 2008 for Moerck et al.
Office Action from Corresponding Japanese Application No. 2005-502047, dated Oct. 19, 2009.
Supplementary European Search Report, EP 06801934, dated Jul. 4, 2009.
Cullel-Young M et al: "Lanthanum Carbonate Treatment of Hyperphosphatemia" Drugs of the Future, Prous Science, ES, vol. 28, No. 3, Mar. 1, 2003, pp. 224-228, XP009014864 ISSN: 0377-8282.
European Search Report, EP 05823302, dated Dec. 1, 2009.
Aldigier et al., Protection of Renal Function with ACE Inhibitors, 1998, Clinical Drug Investment, vol. 16(6), pp. 463-472.
Supplementary European Search Report, EP 06789875, dated Sep. 2, 2008.

(56) References Cited

OTHER PUBLICATIONS

Behets Geert J et al: Does the phosphate binder lanthanum carbonate affect bone in rats with chronic renal failure? Journal of the American Society of Nephrulogy vol. 15, No. 8, Aug. 2004, pp. 2219-2228, XP002492560.
Magill-Lewis J: Coping with chronic kidney disease Drug Topics 20040927 us, vol. 148, No. 18, Sep. 27, 2004, XP008095473.
Office Action from corresponding Canadian Application No. 2,494,992 dated Mar. 25, 2011.
European Search Report, EP 10151585 dated Sep. 3, 2010.
Guilhaume et al. "Oxygen storage capacity in Perovskite-related oxides: The role of overstoichiometric oxygen in three-way catalysis." Catalysis and Automotive Pollution Control IV, Studies in Surface Science and Catalysis, vol. 116, pp. 581-589, 1998.
Altair Nanotechnologies Press Release, "RenaZorb™, Phosphate Lowering Drug for Kidney Dialysis Patients, Shows Promising Laboratory Results" [retrieved on Jun. 3, 2011] Retrieved from Internet: http://www.altaimano.com/profi lesli nvestor/ResLibrary View .asp ?ResLibrary ID=2808&GoTopage=32&Category= 1951 &BzID=546 Published on Oct. 25, 2002.
International Search Report and Written Opinion, PCT/US2011/036317, dated Aug. 2, 2011.
Joy, M. S. et al., 'Safety Profile of Lanthanum Carbonate in Hemodialysis Patients: Results from a Phase III Study,' Journal of the American Society of Nephrology, 10;388A (1999), Abstract No. A1997.
Mzareulishvili et al.; Study of the Interaction of Lanthanum Nitrate with Alkali Metal and Ammonium Carbonates, Chemical Abstracts, Jun. 30, 1986, 81-84 (English Summary on p. 84).
Altair Nanotechnologies Press Release, "Altair Nanotechnologies Reports Results of Testing and Likely Patient Dosing for Phosphate Binding Dialysis Drug" [retrieved on Jun. 3, 2011], Retrieved from Internet: http://www.altairnano.com/profiles/investor/ResLibraryView.asp?ResLibraryID=7038& Topage=23&Category=1951&BzID=546.
Zhang, Youjin; Han, Kaidong; Cheng, Tao; Fang, Zhiyong. Department of Chemistry, University of Science and Technology of China, Hefei, Peop. Rep. China. Inorganic Chemistry (Washington, DC, United States) (2007), 46 (11), 4713-4717.
Li, Zhonghao; Zhang, Jianling; Du, Jimin; Gao, Haixiang; Gao, Yanan; Mu, Tiancheng; Han, Buxing. Center for Molecular Sciences, Institute of Chemistry, Key Lab of Photochemistry, Chinese Academy of Sciences, Beijing, Peop. Rep. China. Materials Letters (2005), 59(8-9), 963-965.
Han, Zhaohui; Xu, Pu; Ratinac, K. R.; Lu, G. Q. ARC Centre for Functional Nanomaterials, University of Queensland, Australia. Journal of Crystal Growth (2004), 273(1-2), 248-257.
Sun, J.; Kyotani, T.; Tomita, A. Chem. Res. Inst. Non-Aqueous Solut., Tohoku Univ., Sendai, Japan. Journal of Solid State Chemistry (1986), 65(1), 94-9.
Christensen, A. Norlund. Dep. Inorg. Chem., Univ. Aarhus, Aarhus, Den. Acta Chemica Scandinavica (1947-1973) (1973), 27(8), 2973-82.
Shirsat, A. N.; Ali, M.; Kaimal, K. N. G.; Bharadwaj, S. R.; Das, D. Chemical Thermodynamics Section, Applied Chemistry Division, Bhabha Atomic Research Centre, Mumbai, India. Thermochimica Acta (2003), 399(1-2), 167-170.
Attfield, J. Paul; Ferey, Gerard. Chem. Crystallogr. Lab., Univ. Oxford, Oxford, UK. Journal of Solid State Chemistry (1989), 82(1), 132-8.
Taiwanese Office Action and Search Report for Application No. 100116778 dated Oct. 14, 2013.
Canadian Office Action for Application No. 2,494,992 dated Aug. 26, 2013.
Brazilian Written Opinion and Examination Report for Application No. PI0313737-6 dated Aug. 23, 2013.
U.S. Office Action for U.S. Appl. No. 13/229,157 dated Oct. 18, 2013.
Olsbye et al. "A comparative study of coprecipitated BaC03/La20n(C03)m catalysts for the oxidative coupling of methane." Catalysis Today, 13 (1992) 603-608.
Australian Patent Report for Application No. 2011252983 dated Mar. 6, 2014.
U.S. Appl. No. 14/104,663, filed Dec. 12, 2013.
Israeli Office Action for Application No. 166803 dated Jan. 7, 2014.
Notice of Allowance for Canadian Application No. 2,494,992 dated Feb. 13, 2014.
U.S. Notice of Allowability for U.S. Appl. No. 12/643,059 dated Oct. 9, 2013.
U.S. Office Action for U.S. Appl. No. 13/229,157 dated Apr. 4, 2014.
International Preliminary Report on Patentability for Application No. PCT/US2011/036317 dated Nov. 13, 2012.
European Communication for Application No. 11721201.9 dated Jan. 31, 2013.
U.S. Notice of Allowability for U.S. Appl. No. 14/149,299 dated May 29, 2014.
Chinese Office Action for Application No. 201180023076.0 dated Nov. 11, 2013.
Office Action from U.S. Appl. No. 12/643,059 mailed Feb. 1, 2013.
Office Action from U.S. Appl. No. 13/229,157 mailed May 2, 2013.
Office Action from U.S. Appl. No. 13/229,157 mailed Nov. 27, 2012.
U.S. Appl. No. 12/051,726, filed Mar. 19, 2008.
U.S. Appl. No. 12/814,716, filed Jun. 14, 2010.
U.S. Office Action for U.S. Appl. No. 10/444,774 dated Dec. 15, 2010.
U.S. Office Action for U.S. Appl. No. 11/181,538 dated Oct. 30, 2009.
U.S. Office Action for U.S. Appl. No. 11/181,650 dated Dec. 29, 2008.
U.S. Office Action for U.S. Appl. No. 11/217,001 dated Jun. 23, 2009.
U.S. Office Action for U.S. Appl. No. 12/051,726 dated Sep. 29, 2011.
U.S. Office Action for U.S. Appl. No. 12/814,716 dated Oct. 27, 2010.
Chinese Office Action for Application No. 201180023076.0 dated Jun. 30, 2014.
Australian Notice of Acceptance for Application No. 2011252983 dated Jul. 10, 2014.

* cited by examiner

Batch 100808

Batch 100908

| | mg PO4/g cmpd | | | |
|---|---|---|---|---|
| Time(min) | RZB011 | RZB013 | RZB012 | RZB014 |
| 0 | 0 | 0 | 0 | 0 |
| 0.5 | 0 | 19 | 0 | 31 |
| 1 | 19 | 9 | 0 | 31 |
| 3 | 38 | 19 | 5 | 59 |
| 5 | 57 | 38 | 17 | 88 |
| 10 | 75 | 66 | 47 | 116 |
| 20 | 132 | 66 | 77 | 154 |
| 30 | 160 | 66 | 96 | 192 |
| 60 | 198 | 57 | 118 | 239 |
| BET m^2/g | 12.3 | 38.4 | 6 - 7 | 33.9 |

LANTHANUM CARBONATE HYDROXIDE, LANTHANUM OXYCARBONATE AND METHODS OF THEIR MANUFACTURE AND USE

CROSS-REFERENCE TO RELATED APPLICATIONS

This application claims the benefit of the filing date of U.S. Provisional Patent Application No. 61/333,887 filed May 12, 2010, the disclosure of which is hereby incorporated herein by reference in its entirety.

BACKGROUND OF THE INVENTION

Pharmaceutical products for use in the treatment of hyperphosphatemia are known in the art. These include those disclosed in U.S. Pat. No. 7,588,782, which describes certain lanthanide containing compounds including lanthanum dioxycarbonate (also referred to herein as LDOC) as well as U.S. Pat. Nos. 5,968,976; 7,381,428; and 7,465,465, describing various lanthanum carbonate hydrates including those of the formula La2(CO3)3.xH2O (also referred to herein as lanthanum tricarbonate). These compounds work by binding phosphate that a subject consumes. One such compound is marketed under the trademark FOSRENOL. Other products for treatment of hyperphosphatemia include RENAGEL, which is a polymeric phosphate binder also known as sevelamer HCl.

In particular, U.S. Pat. No. 7,588,782 describes the production of, inter alia, lanthanum dioxycarbonate from a reaction of lanthanum chloride with sodium carbonate to produce what is referred to therein as a lanthanum oxycarbonate ($La_2O(CO_3)_2.xH_2O$). This is then heated in a furnace at high temperatures to produce lanthanum dioxycarbonate. See generally the '782 patent, example 5. It has subsequently been learned that one compound characterized in the '782 patent as lanthanum oxycarbonate is in fact a lanthanum carbonate hydroxide ($LaCO_3OH$ or LCH) with or without further associated water. It is this compound which is heated to produce lanthanum oxycarbonate. The LDOC material finally produced is said to be crystalline in nature, made up of approximately round particles of about 100 nanometers in size and is noted as being anhydrous. FIG. 20 of the '782 patent shows improved phosphate binding kinetics for LDOC made in accordance with example 5 when compared to various hydrates of lanthanum tricarbonate. Specifically, at 10 minutes, lanthanum dioxycarbonate had bound somewhere between about 70 and 80 percent of the available phosphate where lanthanum tricarbonate tetrahydrate had bound only about 40 percent. This test was undertaken at pH 3.

It was discovered, however, the phosphate binding kinetics of lanthanum dioxycarbonate as described in the '782 patent was not consistent at all pHs. As pH tended to increase, as would happen in the digestive tract of a mammal, the binding kinetics slowed. The '782 patent describes a material of great value pharmacologically and great utility. But, as with most things, there is room for further development.

BRIEF SUMMARY OF THE INVENTION

In one aspect, the present invention relates to a method of producing a lanthanum compound comprising: reacting a soluble salt of a lanthanum (often a lanthanum halide) with a non-alkali metal carbonate in a solvent to produce a lanthanum carbonate hydroxide (LCH) which is then precipitated.

In one embodiment, the relative proportion of lanthanum halide to carbonate in the reaction is about 1:1. In another embodiment, the relative proportions of lanthanum halide to carbonate is about 1:2 or more. In another embodiment, the ratio is about 1:3 or more. In still another embodiment, the amount of lanthanum halide relative to the amount of carbonate in the reaction ranges from between about 1:0.8 and about 1:4. Generally, the LCH material of the present invention has a higher surface area (2-3 times the surface area of the LCH of the '782 Patent), higher bulk and tap density, different morphology (spherical primary particles versus needles and plates), and a different polymorph structure by powder x-ray diffraction (PXRD or PXD). The pattern of the material of the invention has a pattern matching ICDD file 26-815, while that of the corresponding material of the '782 Patent has a pattern matching ICDD file 49-981. The prior art contains some residual sodium (up to 1%) as a result of the sodium-containing precursors used in the synthesis of the compounds, while the material of the invention contains little (incidental traces) or no sodium as the methods of the present invention do not use reactants containing sodium or other alkalis.

In one embodiment, the reaction temperature ranges from between about 65 and about 110 degrees C. and the reaction pH is at least about 4.5.

The non-alkali metal carbonate used may include, without limitation, any water soluble, non-group 1A metal-containing carbonate or bicarbonate such as ammonium bicarbonate and ammonium carbonate.

In one further embodiment, the reaction temperature ranges from between about 75 and about 90 degrees C. and the pH is 6.0 or above.

In one aspect of any of the foregoing, the LCH precipitate exists in the solvent at a precipitate concentration that ranges from between about 20 and about 55 g/L.

In a particular embodiment, the invention relates to a method of producing a lanthanum carbonate compound comprising reacting a soluble salt of a lanthanum halide with a non-alkali metal carbonate in a solvent at a reaction temperature from between about 65 degrees C. to about 110 degrees C. at a pH of at least about 4.5 and precipitating the reaction product, wherein the reaction product is lanthanum carbonate hydroxide which includes about 0.5% by weight or less of an alkali-compound.

In further embodiments, the present invention relates to a method of producing a lanthanum carbonate compound comprising reacting a soluble salt of lanthanum chloride with ammonium carbonate in a solvent at a reaction temperature from between about 75 degrees C. to about 90 degrees C., at a pH of from about 6.0 to 7.5 and precipitating the reaction product, wherein the reaction product is lanthanum carbonate hydroxide which includes about 0.5% by weight or less of sodium. In various embodiments, the amount of lanthanum chloride relative to the amount of ammonium carbonate in the reaction ranges from between about 1:0.8 and about 1:4. In another embodiment, the lanthanum carbonate hydroxide produced has a pattern matching ICDD file 26-815.

Any of these methods can further comprise the step of calcining the LCH so that the powder temperature reaches between about 400 and about 700 degrees C. for at least two hours to produce a lanthanum oxycarbonate. In another embodiment, the calcining powder temperature ranges from about 440 to about 640 degrees C., in still another embodiment, the calcining powder temperature ranges from between about 500 and about 600 degrees C. Often the temperature used is about 550 degrees C. The resulting lanthanum oxycarbonate may be a lanthanum dioxycarbonate and, in particular, $La_2O_2CO_3$ which may be crystalline or amorphous and may be solvated or not.

In some embodiments, the resulting lanthanum dioxycarbonate includes no more than about 10% by weight of another polymorphic form of lanthanum dioxycarbonate referred to herein as $La_2CO_5$. In still another embodiment, the resulting lanthanum dioxycarbonate includes no more than about 5% by weight of $La_2CO_5$ and, in particular, no more than about 1% by weight of $La_2CO_5$.

In some embodiments of any of the foregoing methods, the LCH includes less than about 0.5% by weight (alkali-metal basis) of an alkali-compound and, in particular, sodium. In another embodiment, the total amount of any alkali compound present is 0.3% by weight or less (on an alkali-metal basis—weight of the alkali-compound on the wt % basis calculated based on the metal alone as determined by inductively coupled plasma (ICP)) and in still another embodiment, 0.1% or less.

In other embodiments of any of the foregoing methods, the resulting lanthanum oxycarbonate includes less than about 0.75% by weight (alkali-metal basis) of an alkali compound and, in particular, sodium and in other embodiments, 0.4% by weight or less. In still another embodiment, the lanthanum oxycarbonate of the invention includes 0.2% by weight or less.

Thus, in a particular embodiment, the present invention also relates to the method provided above for producing a lanthanum carbonate compound further comprising calcining the reaction product at a temperature between about 400 and about 700 degrees C. for at least two hours to produce lanthanum dioxycarbonate comprising one or more polymorphs of formulae $La_2O_2CO_3$ and $La_2CO_5$ and which includes about 0.75% by weight or less of sodium. In one embodiment, the calcination temperature is about 550 degrees C. In additional embodiments, the resulting lanthanum dioxycarbonate comprises no more than about 5% by weight of the polymorph of formula $La_2CO_5$. In another embodiment, the resulting lanthanum dioxycarbonate comprises no more than about 1% by weight of the polymorph of formula $La_2CO_5$.

The products produced by any of these processes as described above are also contemplated. Thus, in a particular aspect, the present invention relates to a lanthanum carbonate compound selected from the group consisting of a lanthanum carbonate hydroxide which includes about 0.5% by weight or less of sodium, and a lanthanum dioxycarbonate which comprises one or more polymorphs of formulae $La_2O_2CO_3$ and $La_2CO_5$, and which includes about 0.75% by weight or less of sodium. In a particular embodiment, the lanthanum carbonate hydroxide has a pattern matching ICDD file 26-815. In another embodiment the lanthanum dioxycarbonate comprises no more than about 5% by weight of the polymorph of formula $La_2CO_5$. In another embodiment the lanthanum dioxycarbonate comprises no more than about 1% by weight of the polymorph of formula $La_2CO_5$. In a particular embodiment, the lanthanum dioxycarbonate has either a pore volume of at least 0.015 $cm^3/g$ or includes about 0.75% by weight or less of sodium. In yet another embodiment, the lanthanum dioxycarbonate has either a pore volume of at least 0.020 $cm^3/g$ or includes about 0.75% by weight or less of sodium.

Another embodiment is an aqueous suspension comprising: lanthanum carbonate hydroxide and an ammonium halide in a water solvent.

Aspects of the invention also include lanthanum carbonate hydroxide (LCH) having at least one of: an average aggregate size ($D_{50}$ by volume of aggregates measured by laser based techniques) of between about 4 and about 80 microns; a relatively high porosity (greater than that achieved by use of the same process using a sodium carbonate reactant); a BET surface area of at least about 1 $m^2/g$ and often between about 1 and about 100 $m^2/g$; a bulk density of about 0.1 to about 1.1 and in another embodiment, between about 0.5 and about 0.8 g/cc; an alkali-metal content of about 0.5% by weight (alkali-metal basis) or less.

In another embodiment, the invention includes lanthanum oxycarbonate having at least one of: an average aggregate size (D50 by volume of aggregates measured by laser light based techniques) of between about 4 and about 80 microns; a relatively higher porosity; a pore volume of at least 0.015 $cm^3/g$, or at least 0.020 $cm^3/g$ (greater than that achieved by use of the same process using a sodium carbonate reactant); a BET surface area of at least about 20 $m^2/g$ and often between about 30 and about 40 $m^2/g$; a bulk density of about 0.1 to about 1.1 and in another embodiment, between about 0.5 and about 0.8 g/cc; an alkali-compound content of about 0.75% by weight (alkali-metal basis) or less. The LCH and lanthanum oxycarbonates of the invention often have a specific gravity of 5.15 g/cc±0.1 g/cc.

In some embodiments, the lanthanum oxycarbonate is a specific polymorph of lanthanum dioxycarbonate represented herein by the formula $La_2O_2CO_3$. In some embodiments, this polymorph is essentially pure, substantially pure, or pure with regard to other polymorphs.

A pharmaceutical composition comprising an effective amount of the lanthanum carbonate hydroxide and/or lanthanum dioxycarbonate and at least one pharmaceutically acceptable excipient is also contemplated.

Pharmaceutical compositions comprising an effective amount of an active pharmaceutical ingredient which is a lanthanum carbonate hydroxide or lanthanum oxycarbonates having at least one of the physical properties mentioned above and at least one pharmaceutically acceptable excipient are also contemplated. Thus, in one aspect, the present invention relates to a pharmaceutical composition comprising an effective amount of one or more lanthanum carbonate compounds selected from the group consisting of lanthanum carbonate hydroxide which includes about 0.5% by weight or less of sodium and lanthanum dioxycarbonate which includes about 0.75% by weight or less of sodium, and at least one pharmaceutically acceptable excipient, wherein said pharmaceutical composition is a dosage form selected from the group consisting of swallow tablets, swallow caplets, compressed dosage forms, swallow hard gelatin capsules, swallow soft gel capsules, orally dissolvable tablets, orally dissolvable caplets, orally dissolvable hard gelatin capsules, orally dissolvable soft gelatin capsules, chewable tablets, chewable caplets, chewable capsules, powders, sprinkles, orally disintegrable films, foods, confections, gums, syrups, suspensions, emulsions or dispersions. In a particular embodiment, the pharmaceutical composition comprises lanthanum dioxycarbonate which has either a pore volume of at least 0.015 $cm^3/g$ or includes about 0.75% by weight or less of sodium. In yet another embodiment, the pharmaceutical composition comprises lanthanum dioxycarbonate which has either a pore volume of at least 0.020 $cm^3/g$ or includes about 0.75% by weight or less of sodium.

As contemplated herein, in a particular embodiment the effective amount of one or more lanthanum carbonate compounds (active pharmaceutical ingredient) ranges from between about 125 to about 20,000 mg per dose. In another particular embodiment, the invention relates to a pharmaceutical composition as provided above wherein the effective amount of one or more of the lanthanum carbonate compounds in the dosage form ranges from between about 125 mg to about 20,000 mg and up to about 95% by weight of each dosage form. In yet another particular embodiment, the invention relates to a pharmaceutical composition as provided above wherein the effective amount of one or more lanthanum carbonate compounds ranges from between about 125 mg to about 20,000 mg and up to about 95% by weight of each dosage form and wherein said lanthanum carbonate compound comprises lanthanum dioxycarbonate of formula $La_2O_2CO_3$. In yet a further embodiment, the invention relates to a pharmaceutical composition wherein the effective amount of one or more lanthanum carbonate compounds ranges from between about 125 mg to about 20,000 mg and wherein said lanthanum carbonate compound comprises lanthanum dioxycarbonate of formula $La_2O_2CO_3$. In further embodiments, the invention relates to the pharmaceutical composition provided above wherein the effective amount of one or more lanthanum carbonate compounds is selected from the group consisting of from about 100, 125, 150, 250, 500, 750, or 1000 mg.

In other embodiments, any of the pharmaceutical compositions described herein further comprises a secondary phosphate binder in an amount of up to 150% of the amount of the active pharmaceutical ingredient. Thus the resulting composition could include, as actives, about 33% of the API (LCH and/or lanthanum oxycarbonate of the invention) and about 67% of some other phosphate binding active.

It is contemplated herein that the LCH and lanthanum oxycarbonates of the present invention, and pharmaceutical compositions comprising these compounds, may be used for binding phosphate in vivo, e.g., for the treatment of a condition characterized by an abnormally elevated level of phosphate in the blood, e.g. selected from the group consisting of hyperphosphatemia, chronic kidney disease, general kidney failure, end stage renal disease, and chronic renal insufficiency.

Thus, in another aspect, the invention relates to a method for treating a condition characterized by an abnormally elevated level of phosphate in the blood comprising administering to a subject in need thereof an effective amount of a pharmaceutical composition described herein. In various embodiments, the condition to be treated is selected from the group consisting of hyperphosphatemia, chronic kidney disease, general kidney failure, end stage renal disease, and chronic renal insufficiency.

In additional embodiments, the effective amount of pharmaceutical composition administered to the subject ranges from between about 200 to about 12,000 mg per day or from between about 500 to about 8000 mg/day. The effective amount of pharmaceutical composition administered to the subject may also range from between about 300 to about 4000 mg/day.

In a particular additional embodiment, the invention relates to a method of treating hyperphosphatemia in a subject in need of such treatment comprising administering to the subject an effective amount of LCH or lanthanum oxycarbonate produced by the processes of the present invention or having a total sodium content of about 0.5% or less (alkali-metal basis) or an increased phosphate binding kinetic or greater porosity, relative to that obtained from another LCH or lanthanum oxycarbonate, at a pH of 6.5.

In additional embodiments, the invention relates to methods of treating conditions associated with an abnormally elevated level of phosphate in the blood, e.g., hyperphosphatemia, in a subject in need of such treatment comprising administering to the subject an effective amount of an active pharmaceutical ingredient which is a lanthanum carbonate hydroxide and/or lanthanum dioxycarbonate having at least one of the physical properties noted above. Thus, as contemplated herein, the present invention includes methods of treatment which comprise administering an effective amount of a pharmaceutical composition which comprises a lanthanum dioxycarbonate made according to the methods of the present invention and which exhibits relatively greater BET surface area, pore volume and/or phosphate binding kinetics than a lanthanum dioxycarbonate made according to the process provided in U.S. Pat. No. 7,588,782 utilizing a sodium carbonate reactant, i.e., a LDOC which comprises greater than 0.75% by weight of sodium. To this end, in additional embodiments, the instant invention relates to pharmaceutical compositions wherein the lanthanum dioxycarbonate has relatively greater BET surface area than a lanthanum dioxycarbonate which comprises greater than 0.75% by weight of sodium. In a particular embodiment, the BET surface area is greater than 20 $m^2/g$. In another embodiment, the BET surface area is greater than 30 $m^2/g$. The invention also relates to pharmaceutical compositions wherein the lanthanum dioxycarbonate has relatively greater pore volume than a lanthanum dioxycarbonate which comprises greater than 0.75% by weight of sodium. In a particular embodiment, the pore volume is at least 0.015 $cm^3/g$. In another embodiment, the pore volume is at least 0.020 $cm^3/g$.

In various embodiments of these formulations and methods, other ingredients such as a second API, or one or more excipients, may include alkali metals including sodium such that the total content of alkali metals in the dosage form may be greater than 0.75% by weight. But alkali metals added after calcining of the LCH to form a lanthanum oxycarbonate of the invention are not counted in determining alkali-metal content as described herein.

These methods may further comprise administering simultaneously (at the same time), sequentially (one after another separated by less than about half an hour) or concomitantly (more than half an hour apart) a secondary phosphate binder in an amount of up to 150% of the amount of the active pharmaceutical ingredient (the LCH and/or LDOC).

In some embodiments of these methods, the effective amount of active pharmaceutical ingredient administered to the subject ranges from between about 200 and about 12000 mg per day.

The methods and pharmaceutical compositions of the invention may further comprise administering to the subject a secondary phosphate binder which is bioavailable in the intestine but not in the stomach. A method of binding phosphate is also contemplated which comprises reacting a phosphate source with a lanthanum carbonate hydroxide and/or lanthanum oxycarbonate produced by one of the processes of the invention described herein and/or one of the physical properties described herein is also contemplated. Thus, in another aspect, the invention relates to a method of binding phosphate comprising reacting a phosphate source with a lanthanum dioxycarbonate, and optionally a lanthanum carbonate hydroxide, as provided herein.

DETAILED DESCRIPTION

Figure 1A:
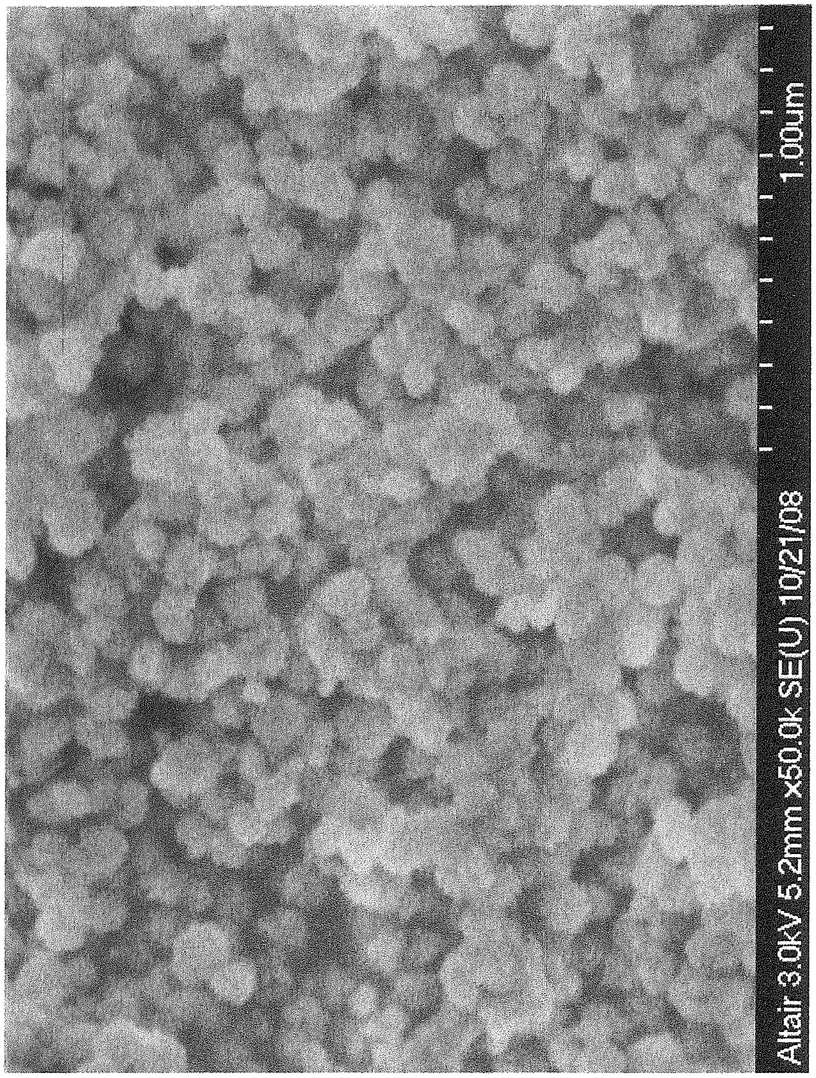
FIG. 1 illustrates the morphology and powder X-ray diffraction patterns for two polymorphs of LCH: high surface area ICDD card file no. 26-815 on the left and lower surface area ICDD card file no. 49-981 on the right.

While the specification concludes with the claims particularly pointing and distinctly claiming the invention, it is believed that the present invention will be better understood from the following description. All percentages and ratios used herein are by weight of the total composition and all measurements made are at 25° C. and normal pressure unless otherwise designated. All temperatures are in Degrees Celsius unless specified otherwise. The present invention can comprise (open ended) or consist essentially of the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention. Preferably, such additives will not be present at all or only in trace amounts. However, it may be possible to include up to about 10% by weight of materials that could materially alter the basic and novel characteristics of the invention as long as the utility of the compounds (as opposed to the degree of utility) is maintained. All ranges recited herein include the endpoints, including those that recite a range "between" two values. Terms such as "about," "generally," "substantially," and the like are to be construed as modifying a term or value such that it is not an absolute, but does not read on the prior art, unless otherwise defined herein. Such terms will be defined by the circumstances and the terms that they modify as those terms are understood by those of skill in the art. This includes, at very least, the degree of expected experimental error, technique error and instrument error for a given technique used to measure a value. The entire teachings of any patents, patent applications or other publications referred to herein are incorporated by reference herein as if fully set forth herein.

Note that while the specification and claims may refer to a final product such as, for example, a tablet or other dosage form of the invention as, for example, containing particles having a certain particle size or distribution, or a certain type of, for example, a specific form of a filler, it may be difficult to tell from the final dosage form that the recitation is satisfied. However, such a recitation may be satisfied if the materials used prior to final production (in the case of a tablet for example, blending and tablet formulation), for example, meet that recitation. Indeed, as to any property or characteristic of a final product which cannot be ascertained from the dosage form directly, it is sufficient if that property resides in the components recited just prior to final production steps.

Where this document refers to a material, such as in this instance, LCH and LDOC, by reference to patterns, spectra or other graphical data, it may do so by qualifying that they are "substantially" as shown or depicted in a figure, or by one or more data points. By "substantially" used in such a context, it will be appreciated that patterns, spectra and other graphical data can be shifted in their positions, relative intensities, or other values due to a number of factors known to those of skill in the art. For example, in the crystallographic and powder X-ray diffraction arts, shifts in peak positions or the relative intensities of one or more peaks of a pattern can occur because of, without limitation: the equipment used, the sample preparation protocol, preferred packing and orientations, the radiation source, operator error, method and length of data collection, and the like. However, those of ordinary skill in the art should be able to compare the figures herein with a pattern generated of an unknown and confirm its identity as one of the forms disclosed and claimed herein. The same holds true for other techniques which may be reported herein.

In addition, where a reference is made to a figure, it is permissible to, and this document includes and contemplates, the selection of any number of data points illustrated in the figure which uniquely define that crystalline form, salt, solvate, and/or optical isomer, within any associated and recited margin of error, for purposes of identification.

A reference to a molecule such as, in this case, LCH and LDOC, unless otherwise specified or inconsistent with the disclosure in general, refers to any salt, crystalline or amorphous form, optical isomer and/or solvate form thereof.

When a molecule or other material is identified herein as "pure," it generally means, unless specified otherwise, that the material is about 99% pure or more. In general, this refers to purity with regard to unwanted residual solvents, reaction byproducts, impurities and unreacted starting materials. In the case of polymorphs, "pure" also means 99% of one polymer relative to others, as appropriate. "Substantially" pure means the same as "pure" except that the lower limit is about 95% pure or more and likewise, "essentially" pure means the same as "pure" except that the lower limit is about 90% pure.

In one aspect, the present invention provides a method of producing a lanthanum compound and in particular a lanthanum carbonate hydroxide with or without associated water (bound water of crystallization). Lanthanum carbonate hydroxide and its properties have been found to have an impact on the phase purity, polymorphic state, morphology, and performance of a resulting lanthanum oxycarbonate made therefrom. In this process a lanthanum halide (bromide, iodide, fluoride, chloride, etc.) in an aqueous solvent is reacted with a stoichiometric excess of a non-alkali metal carbonate, also generally in water. In a particular embodiment, the reaction is performed with at least three times the stoichiometric amount of a non-alkali metal carbonate. A stoichiometric excess assists in maintenance of a desired pH during the reaction and also ensures that all lanthanum reactant has been converted to lanthanum carbonate hydroxide. Other solvents which may be used include low molecular weight alcohols and other aqueous solvents.

Without wishing to be bound by any particular theory of application, the resulting reaction can be illustrated by the following equation:

$$2LaCl_3(aq)+3(NH_4)2CO_3(aq)+H_2O\rightarrow 2LaCO_3OH(s)+6NH_4Cl(aq)+CO_2(g)$$

where (aq)=aqueous, (s)=solid, and (g)=gas. Other non-alkali metal carbonates may also be used in place of ammonium carbonate. Ammonium Bicarbonate ($NH_4HCO_3$) may be used with similar results. The amounts of reactants may need to be adjusted accordingly. It is also harder to maintain high pH using bicarbonate during the reaction. Other sources of carbonate and bicarbonate may be used, so long as they are soluble.

In particular, it has been found that sodium containing carbonate and bicarbonate materials are less advantageous. Without wishing to be bound by any particular theory of operation, even when sodium is washed from the resulting lanthanum carbonate hydroxide, it is believed to influence the properties of the resulting lanthanum oxycarbonate. While both the processes of the present invention and those of the '782 patent can result in relatively high surface areas and small particle sizes, it is believed that the overall effective surface area of the lanthanum carbonate hydroxides and lanthanum oxycarbonates in accordance with the present invention are relatively greater.

By "relatively greater" it is meant that if the processes of the '782 patent and those of the present invention were run under generally identical conditions but with, for example, ammonium carbonate or bicarbonate used instead of sodium carbonate, the surface area, as measured by BET or otherwise, of the LCH or lanthanum oxycarbonates of the present invention would be even higher than that resulting from the practice of the '782 patent. The ammonium carbonate process of the present invention should yield BET surface areas (SA) in the 1 to 100 $m^2/g$ range for LCH. The SA of LDOC in accordance with the invention is expected to be in the range of about 20 to about 40 $m^2/g$ while LDOC from the process of the '782 Patent would often be significantly less. To this end, as used herein "relatively greater BET surface area" refers to the greater BET surface area of the LDOC compound of the present invention when compared to the respective compound in U.S. Pat. No. 7,588,782 when made using similar ingredients, and under similar conditions but using the process described in that patent. As noted above, both processes are capable of producing very fine particles/high surface area. Again without wishing to be bound by any particular theory of operation, it may be that the greater porosity of the materials resulting from the present invention may effectively increase the overall surface area (or more reactive surfaces) allowing for, inter alia, improved binding kinetics. This is predicated on the porosity of individual or primary particles, not aggregates. Thus, it is believed that the primary particles of the invention provide relatively greater porosity than would be measured for particles made in accordance with the '782 Patent. As used herein, "relatively greater porosity", refers to the observation that the overall porosity of a material made according to the methods of the present invention is greater than that of a comparable product made in accordance with U.S. Pat. No. 7,588,782 all other factors being equal. Furthermore, "porosity" as used herein means cumulative adsorption pore volume determined using a static pressure surface area analyzer with nitrogen as the adsorbate and calculating the pore size by The Barrett, Joyner, and Halenda (BJH) method (Barrett E. P., Loyner L. G. and Halenda P. P., The determination of pore volume and area distributions in porous substances. I. Computations from nitrogen isotherms, *J. Am. Chem. Soc.* 73 (1951) pp. 373-380).

Similarly, as used herein, "relatively greater pore volume" refers to the observation that the overall pore volume of a material made according to the methods of the present invention is greater than that of a comparable product made in accordance with U.S. Pat. No. 7,588,782 all other factors being equal. "Pore volume" as used herein refers to the cumulative adsorption pore volume. In one embodiment, the cumulative adsorption pore volume of the LDOC of the present invention is at least 0.015 $cm^3/g$. In another embodiment, it is at least 0.020 $cm^3/g$.

No matter where the explanation may eventually lie, however, it has been observed that materials produced in accordance with the present invention have different properties than those produced in accordance with the '782 patent.

For example, in addition to differences such as in relative pore volume, the LCH and LDOC compounds of the present invention generally demonstrate improved phosphate binding kinetics compared to their respective compounds made in accordance with U.S. Pat. No. 7,588,782. As provided above, by "improved phosphate binding kinetics" it is meant that if the phosphate binding kinetics of the LDOC compounds of the '782 patent and those of the present invention were run under generally similar conditions, (e.g., measured using ICP or ion chromatography assays), the phosphate binding capabilities of the lanthanum oxycarbonates of the present invention would be even higher than the phosphate binding capabilities characteristic of the compounds of the '782 patent when measured at 30 minutes or less and at a pH of 4.5 or above.

There are a number of parameters which influence the production of lanthanum carbonate hydroxide including reaction temperature, reaction pH, precipitate concentration, mixing, feed rates, the purity of the starting materials, and the like. And variations in these reaction parameters can have a significant impact on processability and/or on the nature and characteristics of a lanthanum oxycarbonate ultimately produced from the LCH.

In one process, lanthanum carbonate hydroxide (LCH) is produced by reacting lanthanum chloride and ammonium carbonate in a continuous drip-fed reaction. The amount of lanthanum chloride is provided at a fixed rate and the amount of ammonium carbonate is variably fed. These solutions are fed into a volume of temperature controlled and mixing-controlled water. The pH can be kept close to constant during the reaction and the concentration of the resulting precipitate is controlled by adjusting the weight ratio of the lanthanum chloride provided to the reactor water volume. Once a precipitate is formed, it is washed and filtered to remove the reaction salt which, in this particular case, should be ammonium chloride. This can be accomplished using any traditional process including using a standard laboratory Buchner (vacuum) filtration apparatus. The LCH can be filtered and resuspended in water and refiltered as many times as desirable until a desired suspension conductivity (indicating salt content) is reached. The LCH is then filtered a final time to increase the solids loading for drying. Drying, in which the LCH filter cake (typically 40 to 60 percent solids by weight) can be loaded into pyrex trays and heated in a natural convection drying oven, e.g., a stainless-steel lined convection drying oven, for 16 hours or more at 110 Degrees C., can be used. Other traditional drying techniques may be used. Thereafter, the material can be dry milled and screened through, for example, a 0.6 millimeter mesh screen.

The pH of this reaction can vary, but should be greater than about pH 4.5. However, depending on, in particular, the temperatures used and the concentration of the resulting precipitate, a pH of below 5 and even below 6 may reduce overall surface area. The resulting materials also may suffer in terms of bulk density. The trend, in the testing done so far seems to indicate that at a pH of 6.0 or above (up to about pH 8.0) the average BET-surface area (BET-SA) is generally higher. The surface area and bulk density are believed to be improved as pH increases.

TABLE 1

Effects of pH within the constraint of 85 Degrees C. reaction temperature and 36-45 g/L concentration.

| pH | Average LDOC BET-SA (m^2/g) | Average Bulk Density (g/cc) | Number of samples with BET-SA below 20 m^2/g | Number of Samples |
|---|---|---|---|---|
| 5.5 | 9.8 | 0.41 | 3 | 3 |
| 6 | 22.0 | 0.66 | 2* | 8 |
| 6.5 | 20.9 | 0.77 | 2 | 3 |
| 7 | 23.9 | 0.90 | 0 | 4 |

*One batch from this group saw an instrumentation malfunction accompanied by a drop in pH to ~4.5 momentarily, which may have caused the low BET-SA. The other batch saw an unusual drop in BET-SA from 41 m^2/g as LCH to 16 m^2/g as LDOC.

The samples identified in Table 1 were synthesized at an 85 Degrees C. reaction temperature, and 36-45 g/L LCH concentration.

The data in Table 1 suggests that a low pH of 5.5 precipitates a low-SA LCH which in turn produces the low LDOC BET-SA (BET surface area) observed. A low bulk density at this pH is also observed, which has been observed to mildly correlate with BET-SA and thus is not surprising. At a pH of 6.0 or above, the average BET-SA is higher. The BET-SA appears slightly better still at a pH of 7.0.

Figure 4:
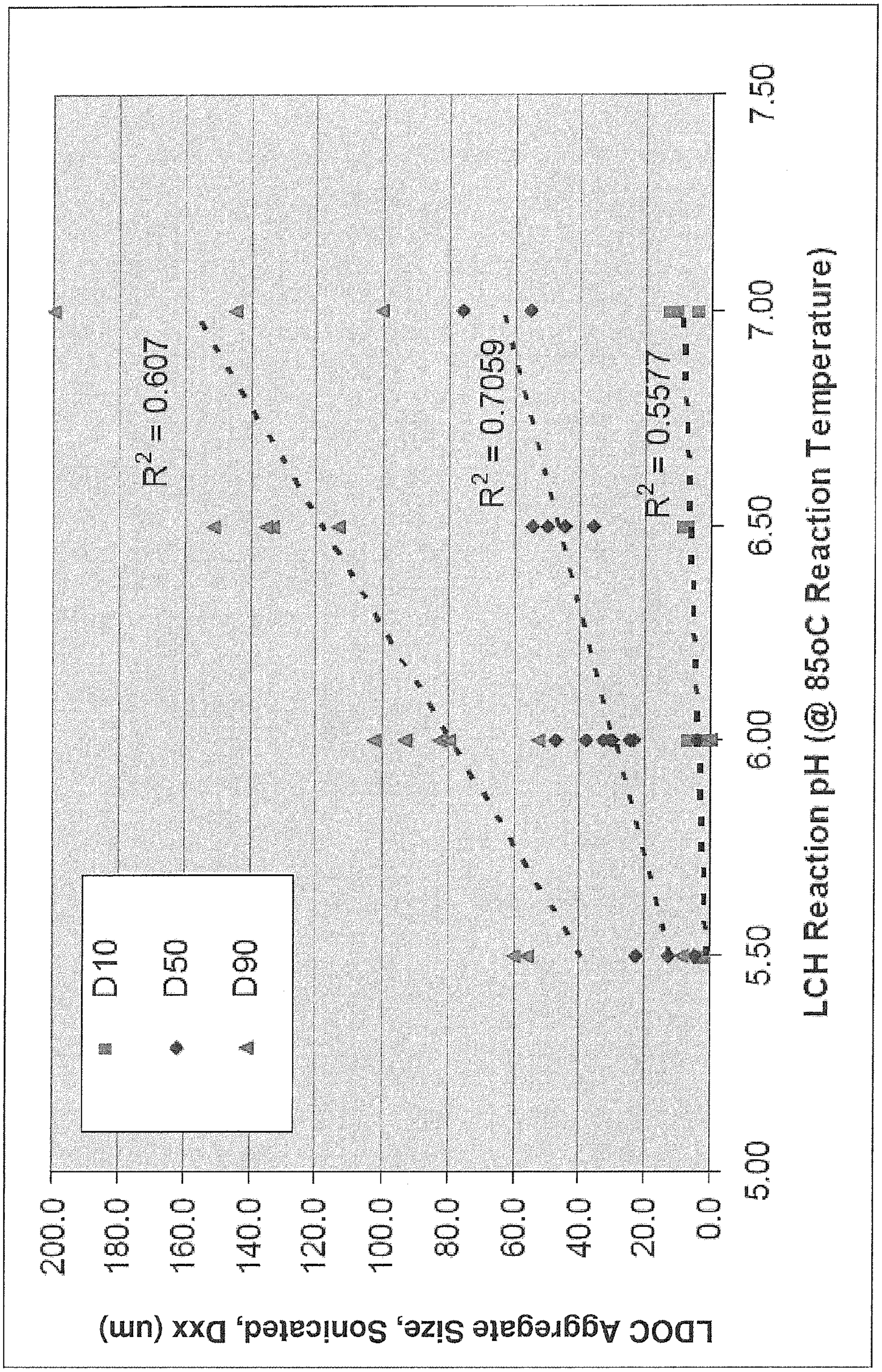
FIG. 4 illustrates the relationship between LCH reaction pH and LDOC aggregate (particle) size at a given temperature.
Figure 5:
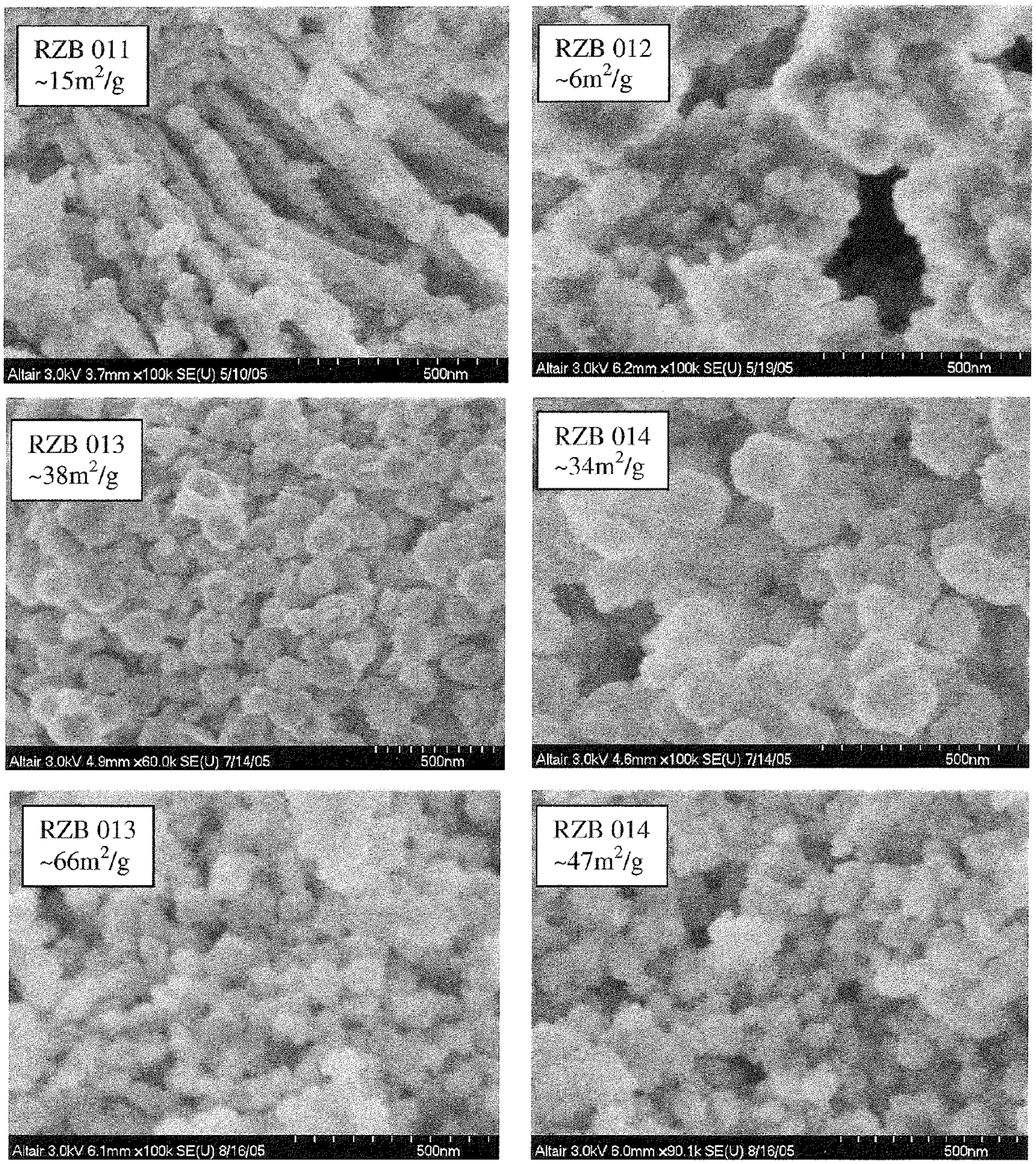
FIG. 5 illustrates scanning electron microscope images of LCH and LDOC produced in accordance with the invention (RZB013 and RZB014 respectively) in comparison to the materials produced before and after calcining in accordance with the '782 Patent (RZB011 and RZB012 respectively). Note the difference between RZB-012 and RZB-014, which have very different morphologies.
Figure 6:
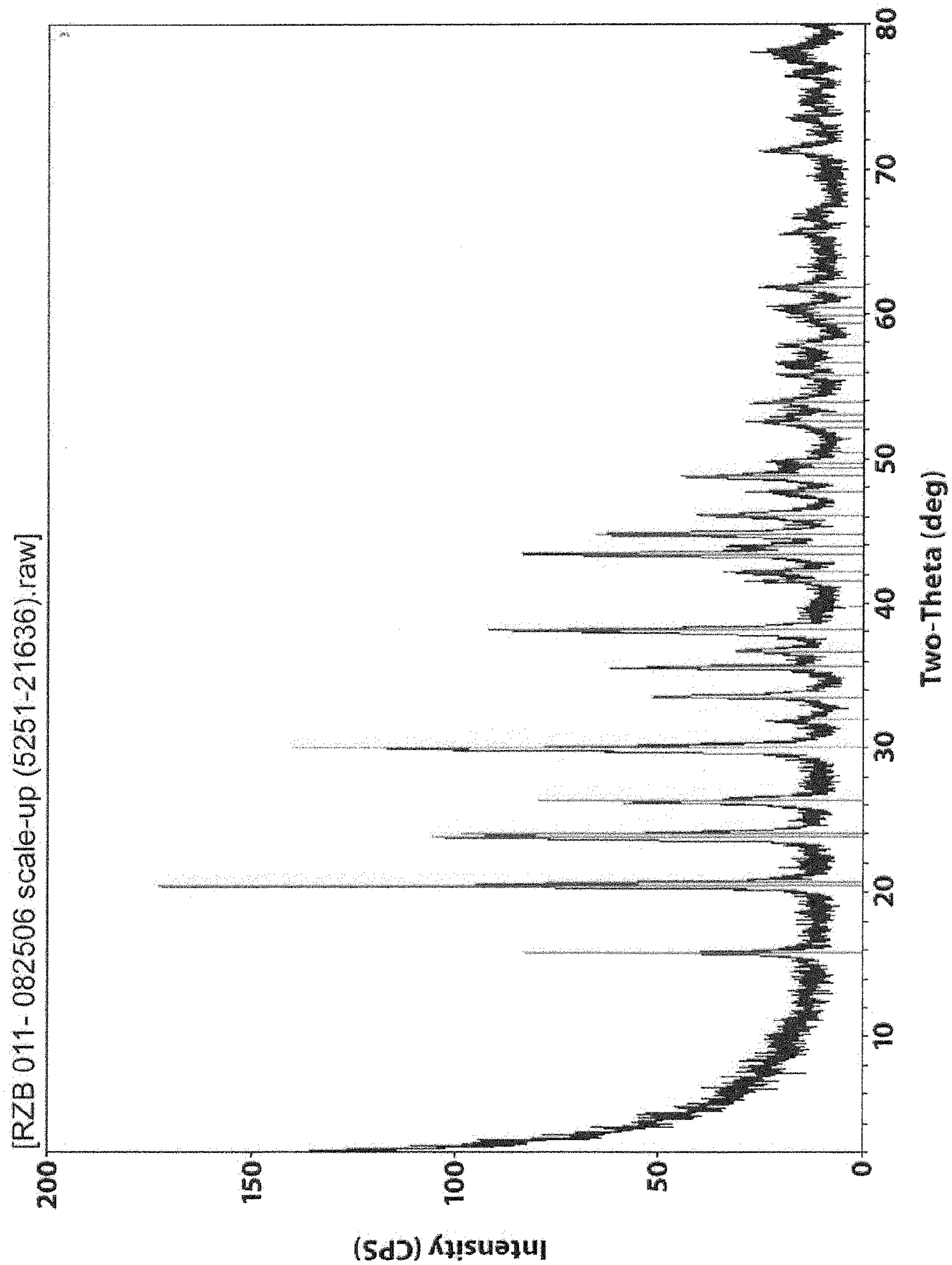
FIG. 6 is the PXRD pattern for RZB-011 produced in accordance with the '782 Patent.
Figure 7:
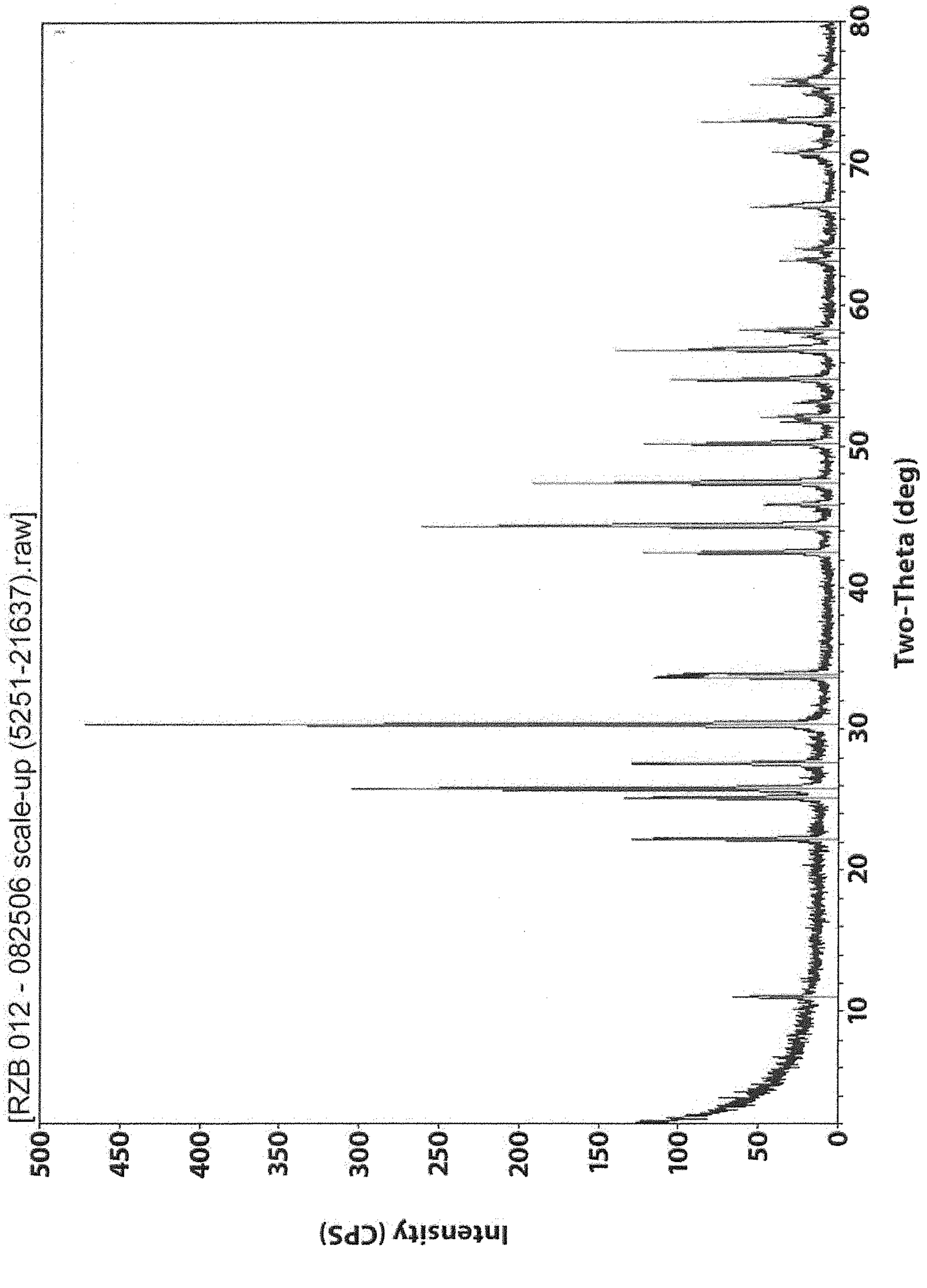
FIG. 7 is the PXRD pattern for RZB-012 produced in accordance with the '782 Patent.
Figure 8:
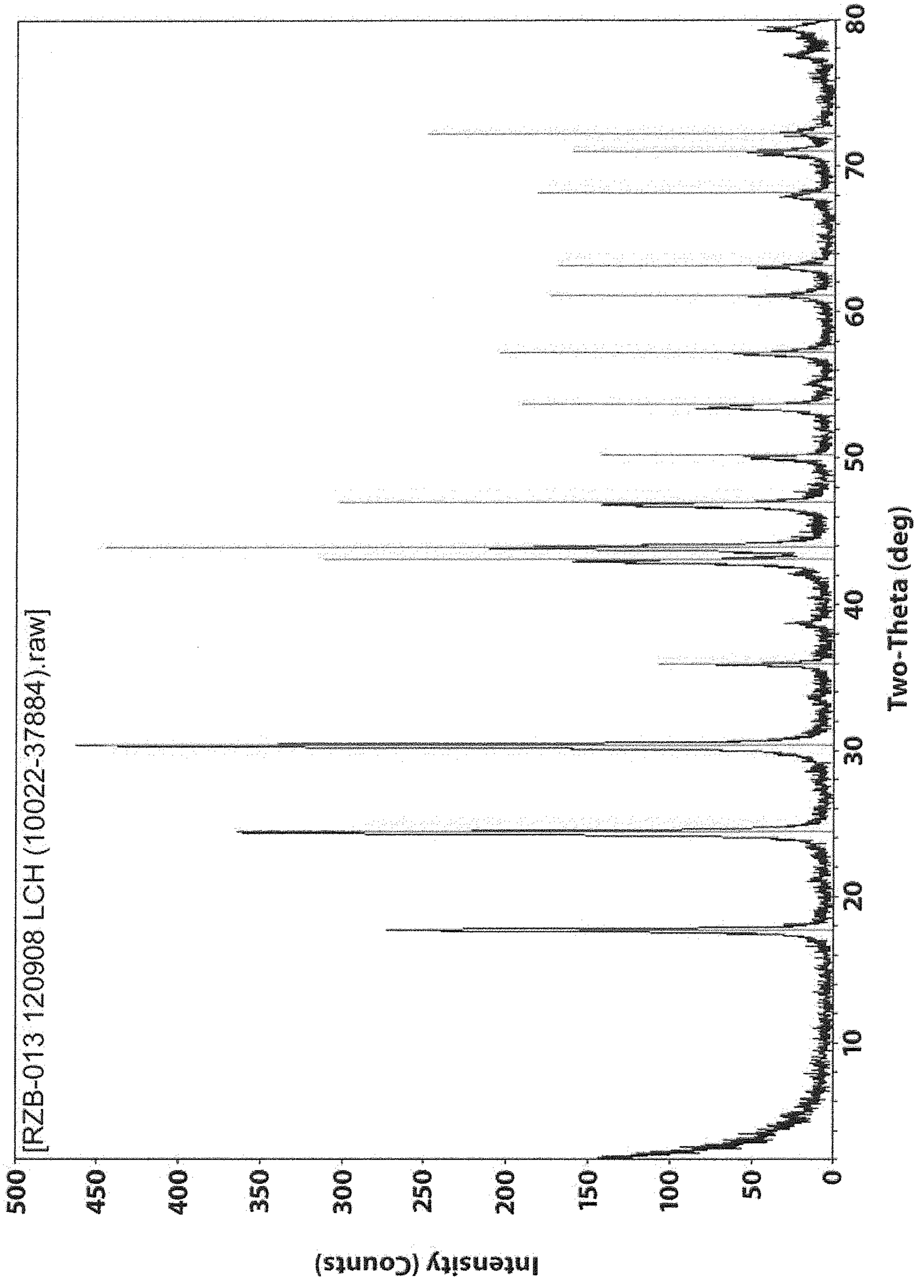
FIG. 8 is the PXRD pattern for RZB-013 produced in accordance with the present invention.
Figure 9:
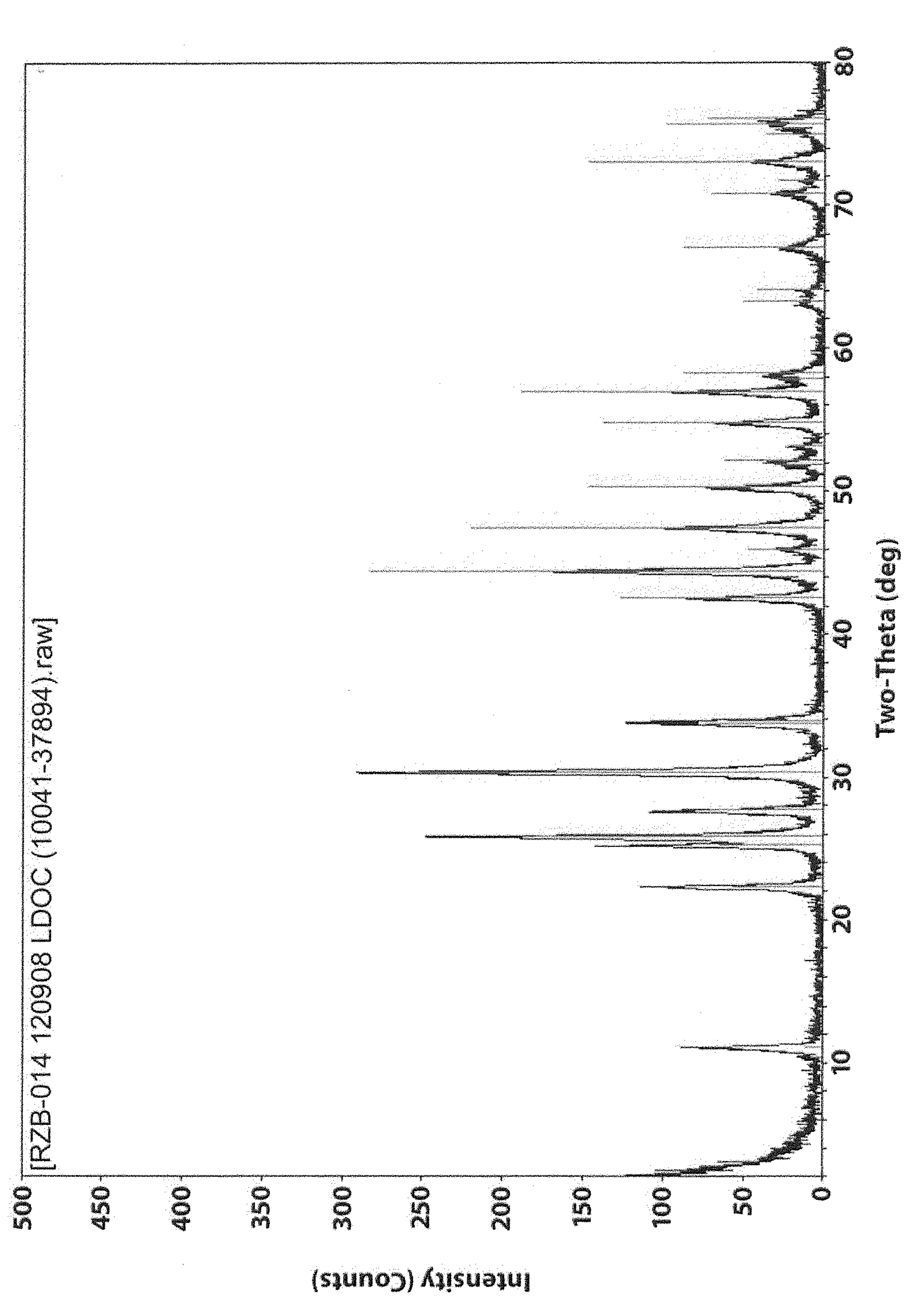
FIG. 9 is the PXRD pattern for RZB-014 produced in accordance with the present invention.

As shown in FIG. 4, the pH at which LCH was produced may also play a role in determining the aggregate size of the LDOC produced therefrom. As the pH increased, so too did aggregate size. But the initial data for BET-SA did not match this trend. Thus, pH may be impacting the relative agglomeration strength of the aggregates and not the actual size and surface area.

Reaction temperature also plays a role. It has been found that at temperatures of 75 Degrees C. or below or 90 Degrees C. or above, the overall surface area of the resulting LCH may in fact be suboptimal. While it may be possible, depending upon other conditions, to obtain a suitable product with desirable surface area at temperatures below 75 and above Degrees C., processes being run between these two temperatures may be optimum. Accordingly, in one embodiment, the reaction temperature may be between about 65 and 110 Degrees C., in another embodiment the reaction temperature will range from between about 70 and 100 Degrees C. and in still another embodiment between 75 and 90 Degrees C. In one particular embodiment, the reaction temperature will range from between about 80 to about 85 Degrees C. Table 2 below illustrates the effect of temperature on BET-SA, and some effects on processability.

TABLE 2

Effects of Temperature on BET-SA and processability

| Temperature (° C.) | Average BET-SA (m^2/g) | Percentage of Batches which "gelled" | Average Filter Cake Moisture (%) | Number of Samples |
|---|---|---|---|---|
| 75 | 16.9 | 71% | 76 | 7 |
| 80 | 23.2 | 100%* | 64 | 3 |
| 85 | 20.2 | 20% | 56 | 20 |
| 90 | 8.0 | 0% | 43 | 3 |

*All the samples in this group were also produced at a high LCH concentration, which confounds the effect of temperature alone on gelling, i.e. the gelling is more likely due to the high concentration rather than the 80 Degrees C. process temperature.

The data indicates that both at 75° C. and 90° C., the BET-SA is reduced. The BET-SA average is maximum at 80° C. and 85° C. Additionally, at 75° C., the majority of the batches gelled during the reaction, indicating a consistent problem with processability. In addition, at this temperature the filter cakes retained a very high moisture content, making removal of the reaction salt via washing quite difficult. It should be noted that although 100% of the materials gelled at an 80° C. reaction temperature, all three samples of this group were also processed at a concentration of 55-60 g/L, which as will be noted shortly also presents problems of gelling and filtration. Higher temperatures may be more useful at lower concentrations.

The concentration of the precipitate also can play a role particularly in terms of processability. If the concentration is too high, viscosity becomes too great and the material seems to "gel" as noted briefly above. This makes further processing difficult. Filtering becomes complicated, drying times may increase, and there may be an impact on the overall performance of the resulting material. Of course, depending upon the other conditions used, such as, for example, pH and temperature, a wider range of precipitate concentrations are possible. However, the precipitate concentration should generally range from between about 20 to about 90 grams/Liter and in another embodiment from about 30 to about 60 grams/Liter. In still another embodiment, the precipitate concentration should be between about 35 and about grams/Liter. Table 3 summarizes the effects of LCH concentration on the ability to process LCH during the reaction and filtration and washing.

TABLE 3

Effects of LCH concentration on processability of materials.

| LCH Concentration (g/L) | Percentage of Batches which "gelled" | Percentage of Samples with Cake Moisture above 70% | Number of Samples |
|---|---|---|---|
| 36-45 | 12% | 20% | 25 |
| >55 | 88% | 67% | 8 |

This suggests that a rise in concentration reduces the ability to process LCH during the reaction. 100% of runs using a concentration of greater than 55 g/L, under these conditions, gelled, and many resulted in high cake moistures about 70%. It appears that the concentration should, under these conditions, be kept below 55 g/L to allow for control in processing under these conditions.

Depending upon the process variables used, various polymorphic phases of LCH may be produced. In one desirable embodiment, the process is practiced such that the resulting material has a highly spherical morphology and a powder X-ray diffraction pattern similar to that of known ICDD card 26-815 (International Centre for Diffraction Data, 12 Campus Blvd., Newton Square, Pa. 19073-3273) See FIGS. 1A and 1C. When practiced suboptimally, the process can result in a generally lower surface area material which also can include a relatively high percentage of a different polymorph whose PXRD pattern most closely matched ICDD card file no. 49-981. The morphology also generally takes on a needle and plate-like structure. See FIGS. 1B and 1D. Using the processes described herein to produce a higher percentage of a polymorph having a powder X-ray diffraction pattern of 26-815 is desired. Thus, in one aspect of the present invention, the LCH produced and used in further processing steps will be more than 50% polymorph 26-815, and in one embodiment, at least about 90% 26-815 of this polymorph relative to other polymorphs. In still another embodiment, the percentage of polymorph 26-815 is 95% or more and in still another embodiment, 99% or more.

In another aspect of the invention, the LCH produced using a non-alkali metal carbonate is further processed by being heated or calcined at generally high temperatures to produce a lanthanum oxycarbonate and in particular LDOC. The temperature and times used for calcining can have an impact on the resulting properties of the LDOC such as, for example, crystallinity, polymorphic form, porosity, surface area and bulk density. However, the influences of calcining conditions are believed to play a less important role than the conditions used to produce the LCH starting material and the nature of that starting material in terms of these same properties.

The calcining temperature (which means the temperature of the LCH powder during calcining) generally can range from between about 400 to about 700 and more often about 440 and about 640 degrees C. But more often still calcining is accomplished at a temperature of between about 500 and 600 Degrees C. (such as 550 degrees C.). The minimum amount of time that these temperatures are applied depends upon a number of factors including, for example, the amount of material and the temperature being used. However, generally, these temperatures will be applied for a minimum of about two hours and in another embodiment, three hours or more. While there is no upper limit on the amount of time that can be used, exposure times that these temperatures certainly do reach a point of diminishing return. Accordingly, generally, the material will not be subjected to these temperatures for greater than about a day.

Various cooling techniques may be used in accordance with the present invention but preferably, the calcined material is gradually cooled over a period of a number of hours such as, for example, over a period of about eight hours.

When the process of the present invention is performed, it has been found that the resulting materials can have a range of properties. Generally, the LCH in accordance with the process of the present invention will have an average aggregate size ($D_{50}$ by volume of aggregates measured by laser light based techniques) of between about 4 and about 80 microns (often 4-30 microns), a relatively higher porosity, a BET surface area of at least about 1 meter squared per gram, often between about 1 and about 100 $m^2/g$, a bulk density of about 0.1 to about 1.1 and in another embodiment between about 0.5 and about 0.8 g/cc and/or alkali-metal content of about 5% or less by weight (alkali-metal basis by ICP). The alkali metal content may also be 0.3% or less or 0.1% by weight or less (alkali-metal basis by ICP).

Similarly, the lanthanum oxycarbonate and in particular the LDOC of the present invention will have an average particle size ($D_{50}$ by volume of aggregates measured by laser light based techniques) of between about 4 and about 80 microns, a relatively higher porosity, a BET surface area of at least about 20 meters squared per gram, and often between about 30 and about 40 $m^2/g$, a bulk density of about 0.1 to about 1.1 and in another embodiment, between about 0.5 and about 0.8 g/cc and/or an alkali-metal content of about 0.75% or less by weight. In some embodiments, the amount of alkali-metal present is 0.4% by weight or less and in still other embodiments, 0.2% by weight or less (all calculated on an alkali-metal basis determined by ICP). In some embodiments the pore volume is at least 0.015 $cm^3/g$, and in other embodiments the pore volume is at least 0.020 $cm^3/g$.

Note that the average particle size measurements reported here are $D_{50}$ by volume of aggregates. These aggregates are made up of individual particles having a particle size (often called a primary particle size) which is far lower. Primary particle size can be judged somewhat empirically from SEM images or may be estimated based on PXRD data using the Scherrer Equation. Particle size may also be estimated by solving the following equation: Average Estimated Particle Size=6000/BET/specific gravity. For an $La_2O_2CO_3$ material with a BET surface area of 25 $m^2/g$ and a specific gravity of 5.15, this means that the average estimated particle size (for the primary particles) is about 47 nanometers, compared to an average estimated agglomerate size measured by a laser light technique of about 7 microns. The average primary particle size may range from about 50 to about 300 nm.

An interesting phenomena has been observed from the practice of the present invention which was not observed by the practice of the processes described in the '782 patent. In both processes some form of LCH is produced and calcined to form LDOC. Polymorphically, the resulting LDOC from both processes can be the same. In some embodiments, the LDOC exhibits a powder X-ray diffraction pattern found in ICDD card file 037-0804 or 023-0322 although 037-0804 is preferred. (In the '782 patent, ICDD card file XRD pattern 023-0322 was designated as $La_2CO_5$ whereas ICDD card file pattern 037-0804 was identified as $La_2O_2CO_3$ and that nomenclature is maintained herein.) Characteristic peaks for LCH produced in accordance with the '782 Patent are found at 15.88, 20.44, 23.76, 29.94, 38.18, and 43.46 degrees two theta±0.1 degree two theta. The characteristic peaks for LCH produced in accordance with the present invention are found at 17.76, 24.44, 30.39, 42.96, and 43.94 degrees two theta±0.1 degree two theta. The $La_2O_2CO_3$ material produced in accordance with the present invention has characteristic peaks at 11.10, 25.86, 30.40, 33.84, and 44.39 degrees two theta±0.1 degree two theta. Interestingly, however, the morphology of the LDOC produced from these different processes—from LCH produced differently—are different from each other. Some of their respective properties such as bulk density and surface area tend to stay reasonably consistent between LCH and LDOC when those materials are produced in accordance with the present invention. However, the same cannot be said for the practice of the '782 patent surface area and morphology, which were noted as changing significantly. Note in Table 1 of the '782 patent, for example, that LCH (identified therein as $La_2O(CO_3)_2.xH_2O$) had a consistently higher BET surface area than either lanthanum oxycarbonate.

Figure 2:
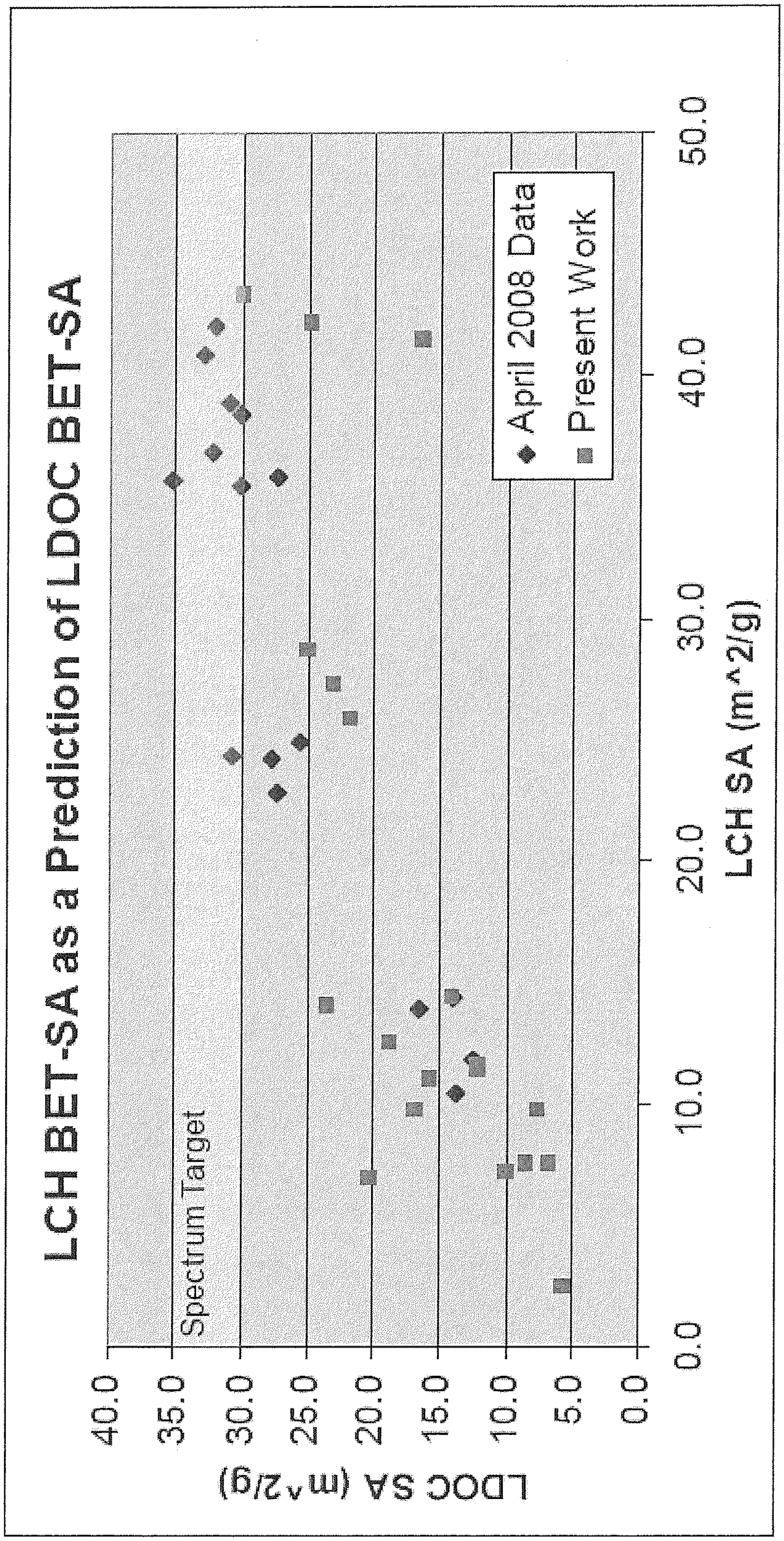
FIG. 2 illustrates the interdependence of BET surface area of LDOC and the BET surface area of LCH produced in accordance with the invention.
Figure 3:
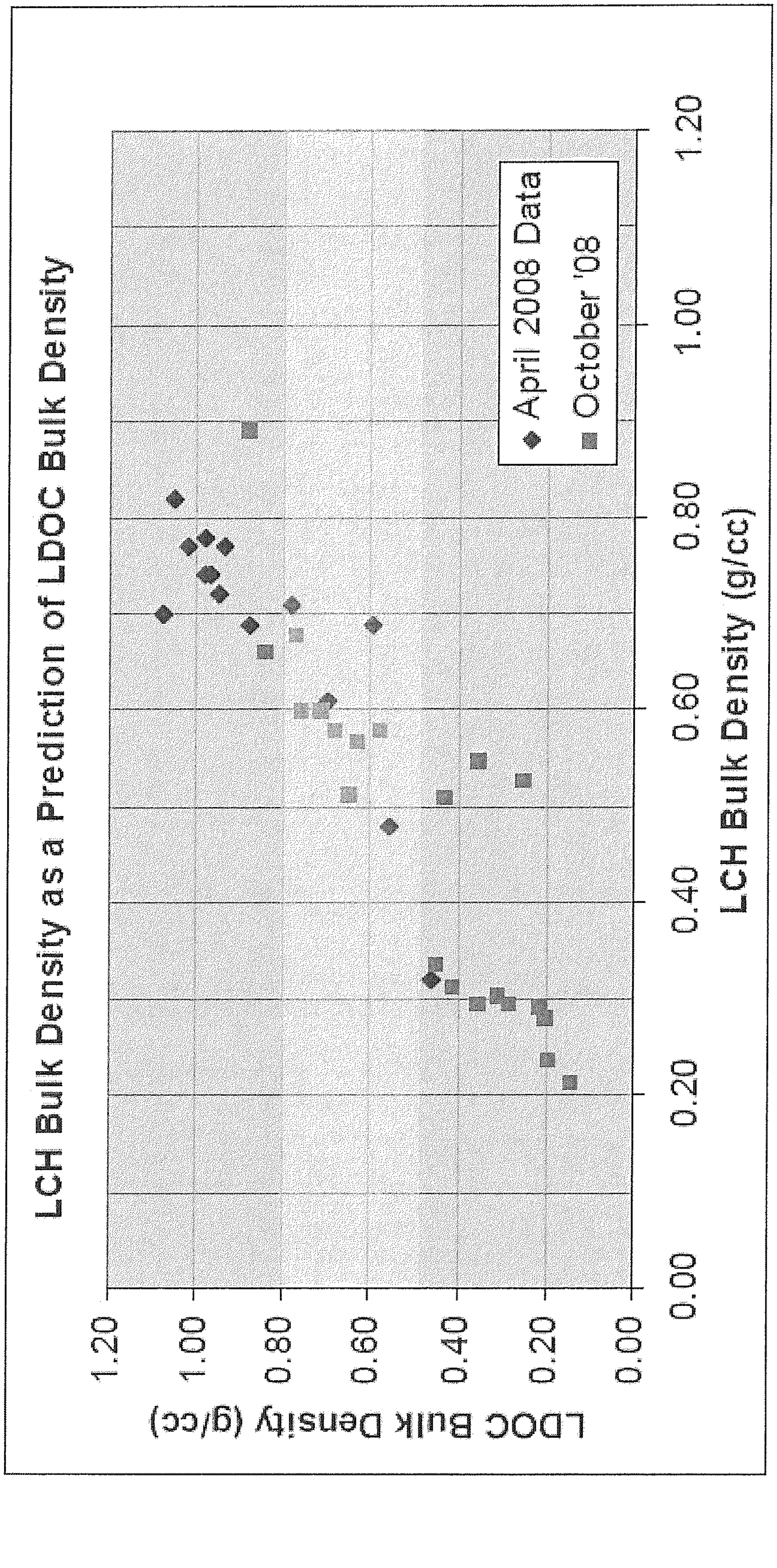
FIG. 3 illustrates the interdependence of the bulk density of LDOC and the bulk density of LCH produced in accordance with the invention.

As shown in FIG. 2, a fairly consistent relationship has been observed between the LCH and the LDOC produced using the process of the invention. The fact that the BET surface area did not change dramatically upon calcining also helps demonstrate the importance of the process used to make LCH and the importance of the LCH made in accordance with the invention. FIG. 3 makes a similar point illustrating the fact that bulk density tends to stay similar as well.

Figure 10:
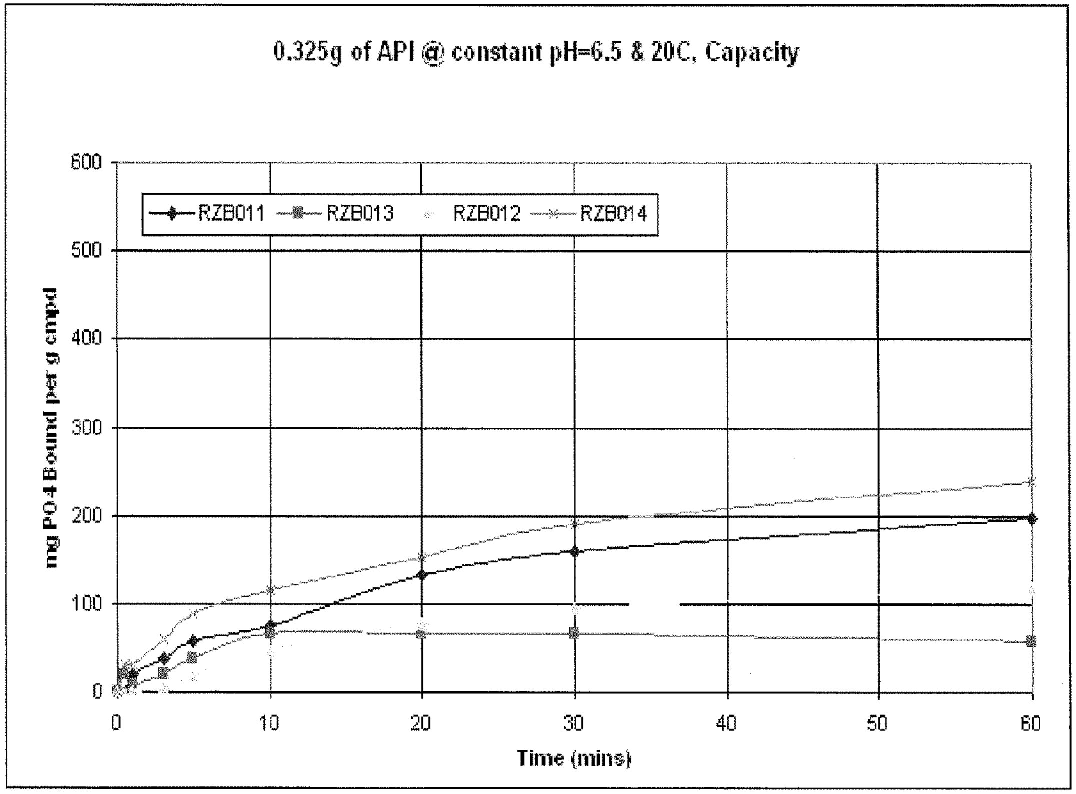
FIG. 10 provides a graphical representation of the binding kinetics of LCH and a lanthanum oxycarbonate in accordance with the '782 Patent (RZB-011, RZB-012), and LCH/$La_2O_2CO_3$ produced in accordance with the present invention (RZB-013 and RZB-014) at 10, 20, 30, 40, 50 and 60 minutes at a constant pH of 6.5 at 20 degrees C. measured as provided herein.
Figure 11:
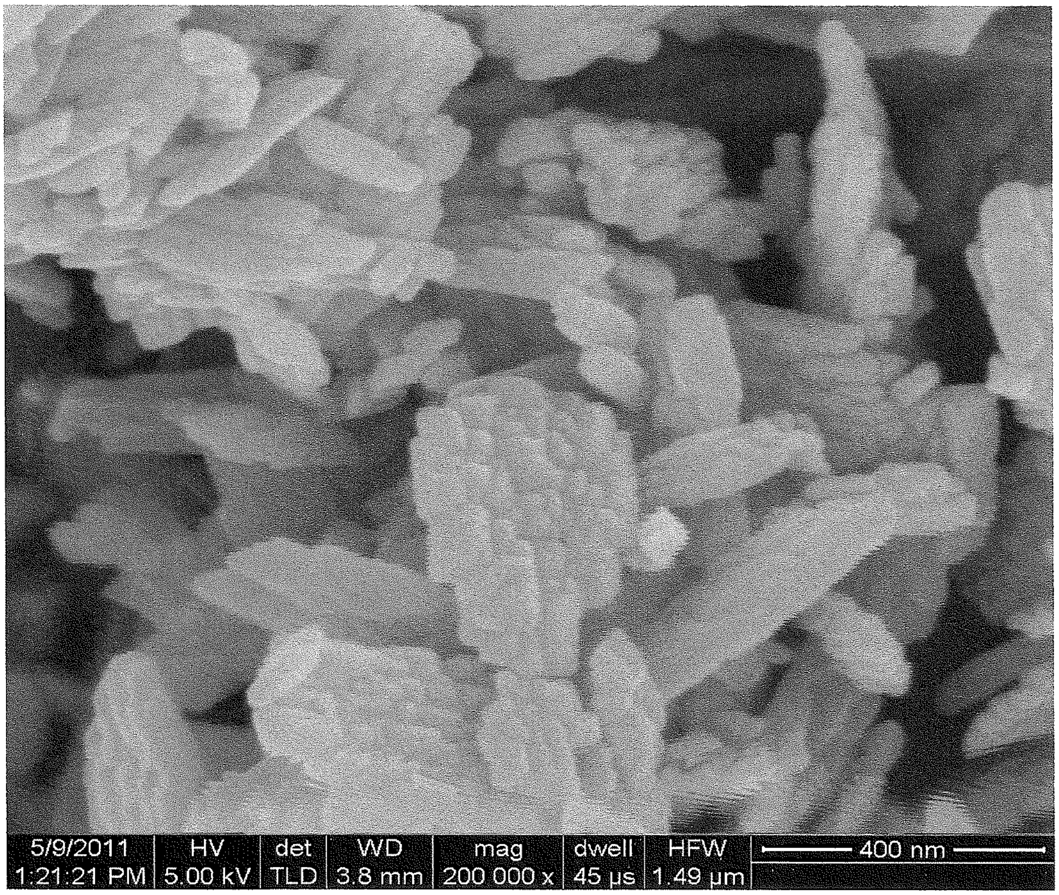
FIGS. 11-20 illustrate scanning electron microscope images (200,000 magnification) of LCH (FIGS. 11-13) and LDOC (FIGS. 14-15) produced in accordance with the methods of U.S. Pat. No. 7,588,782, and LDOC produced according to the methods of the present invention (FIGS. 16-20).
Figure 12:
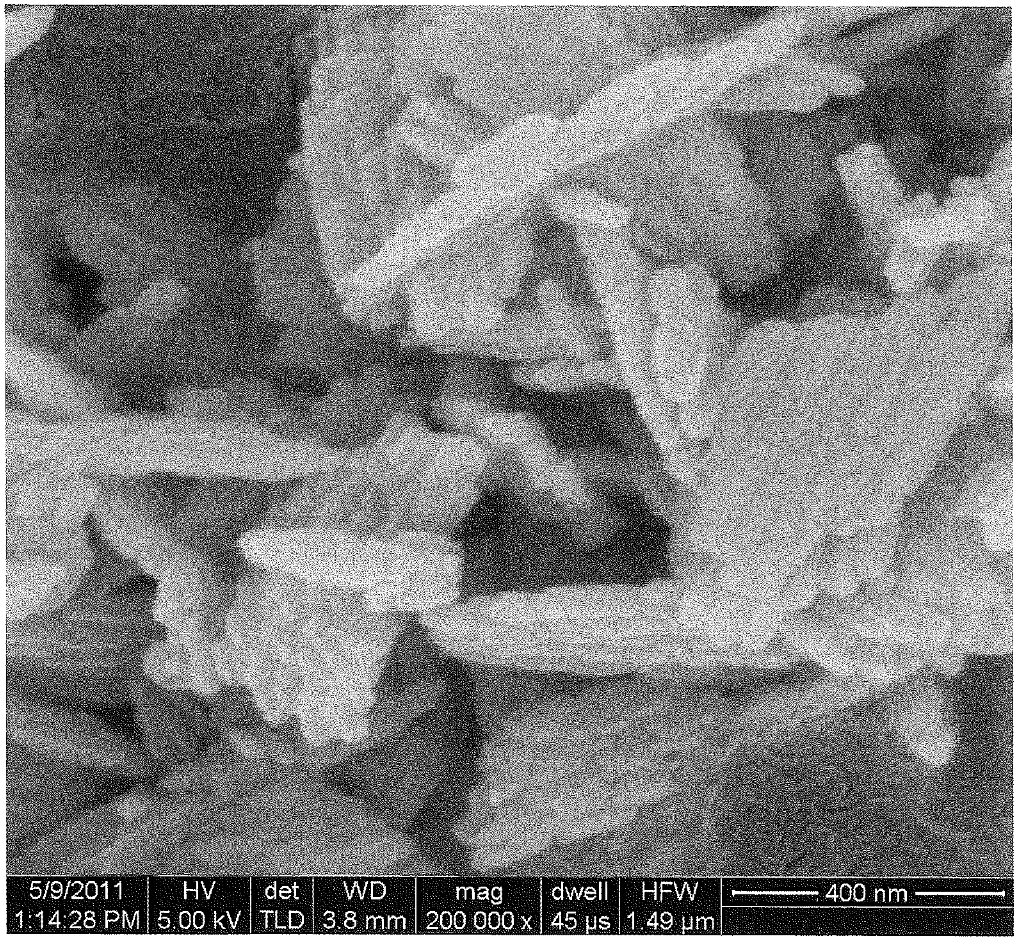
Figure 13:
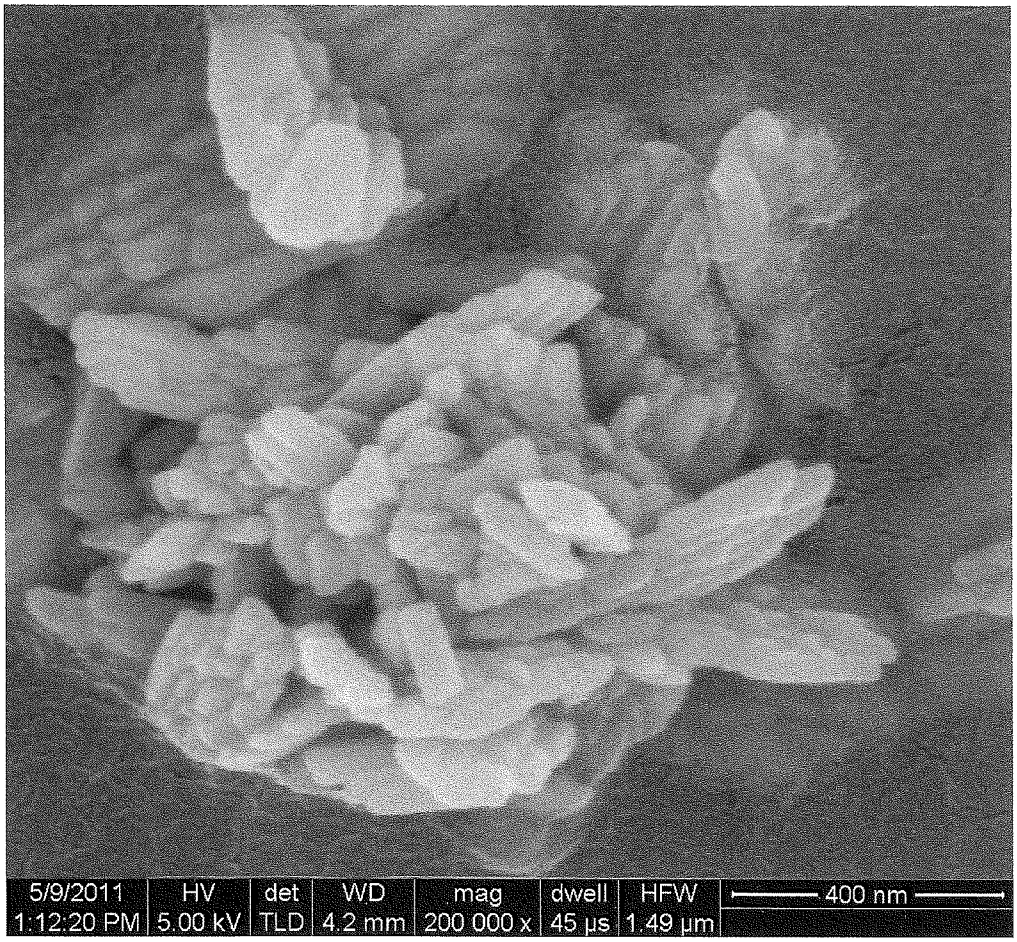
Figure 14:
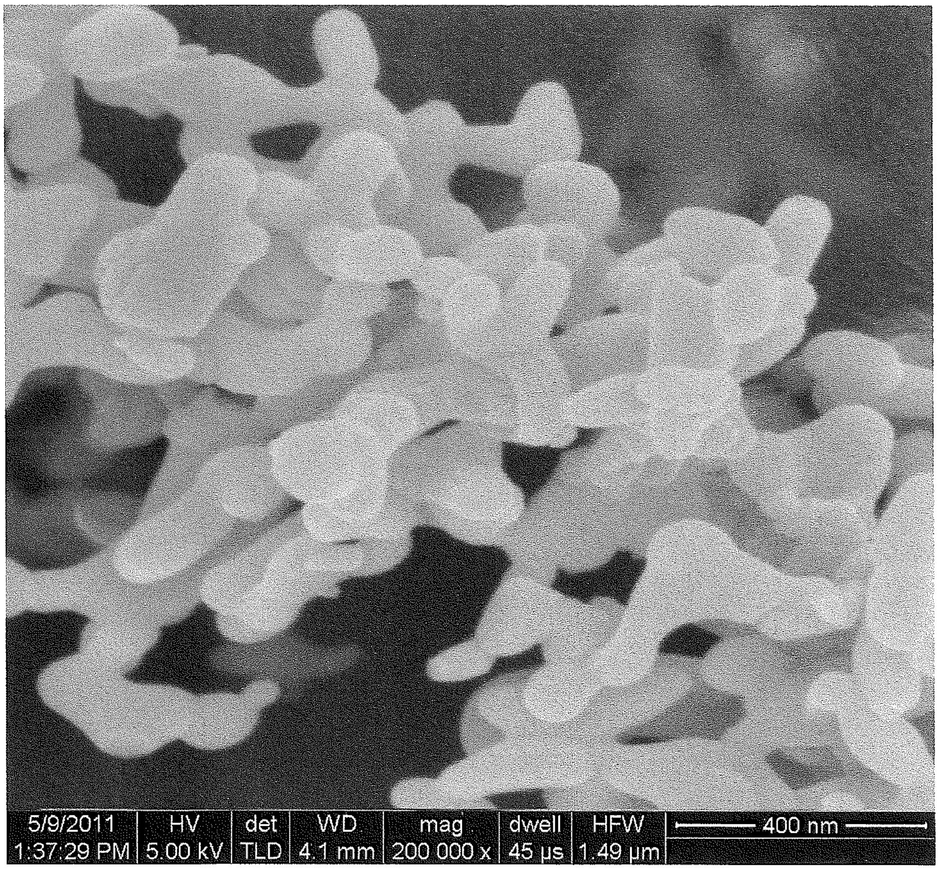
Figure 15:
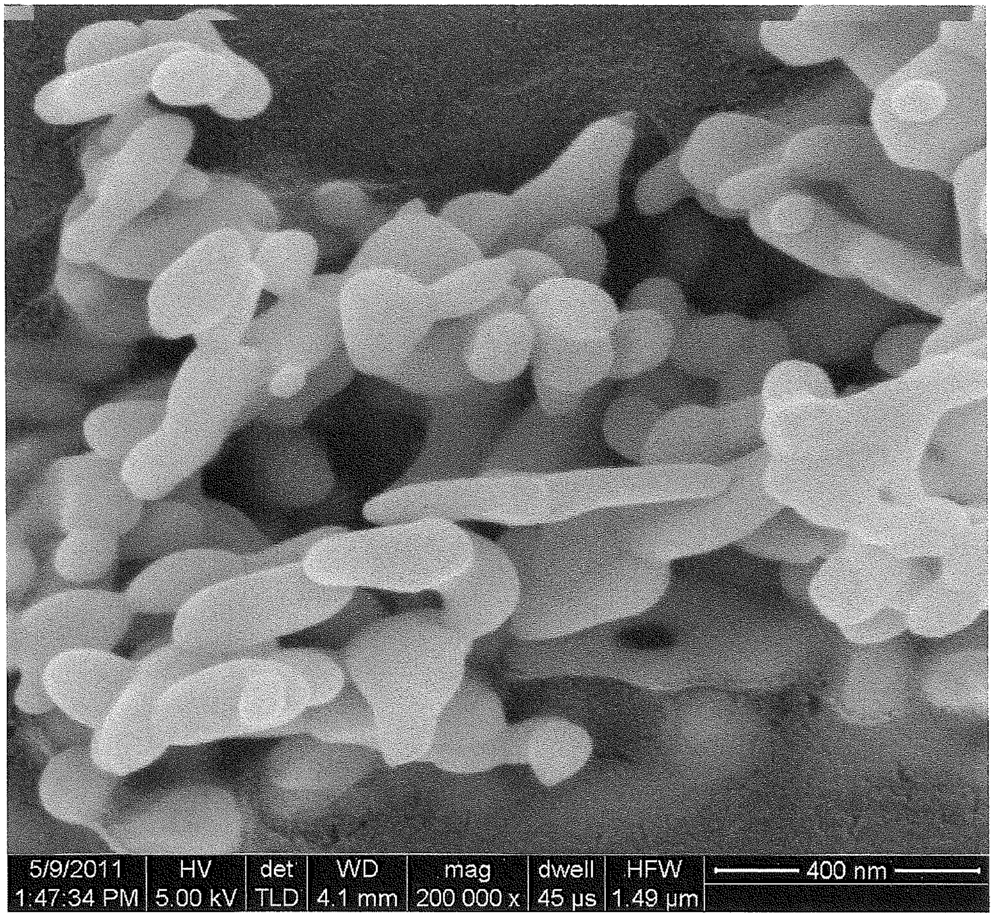
Figure 16:
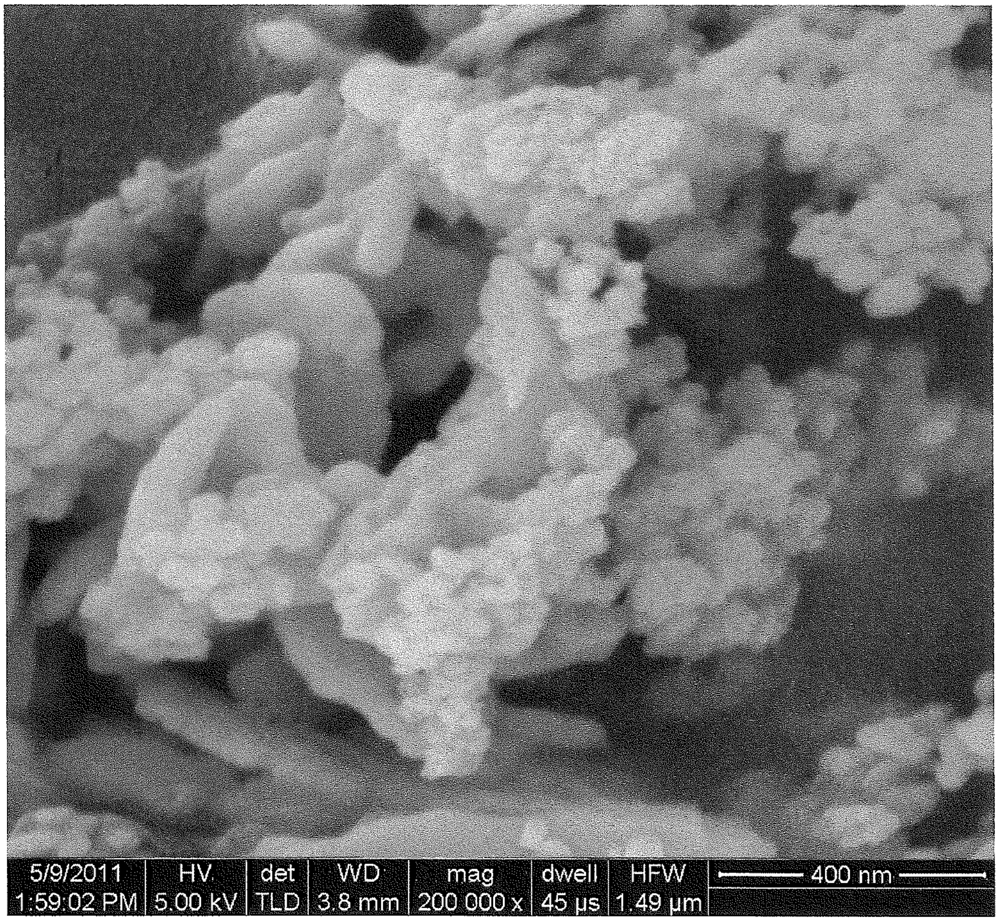
Figure 17:
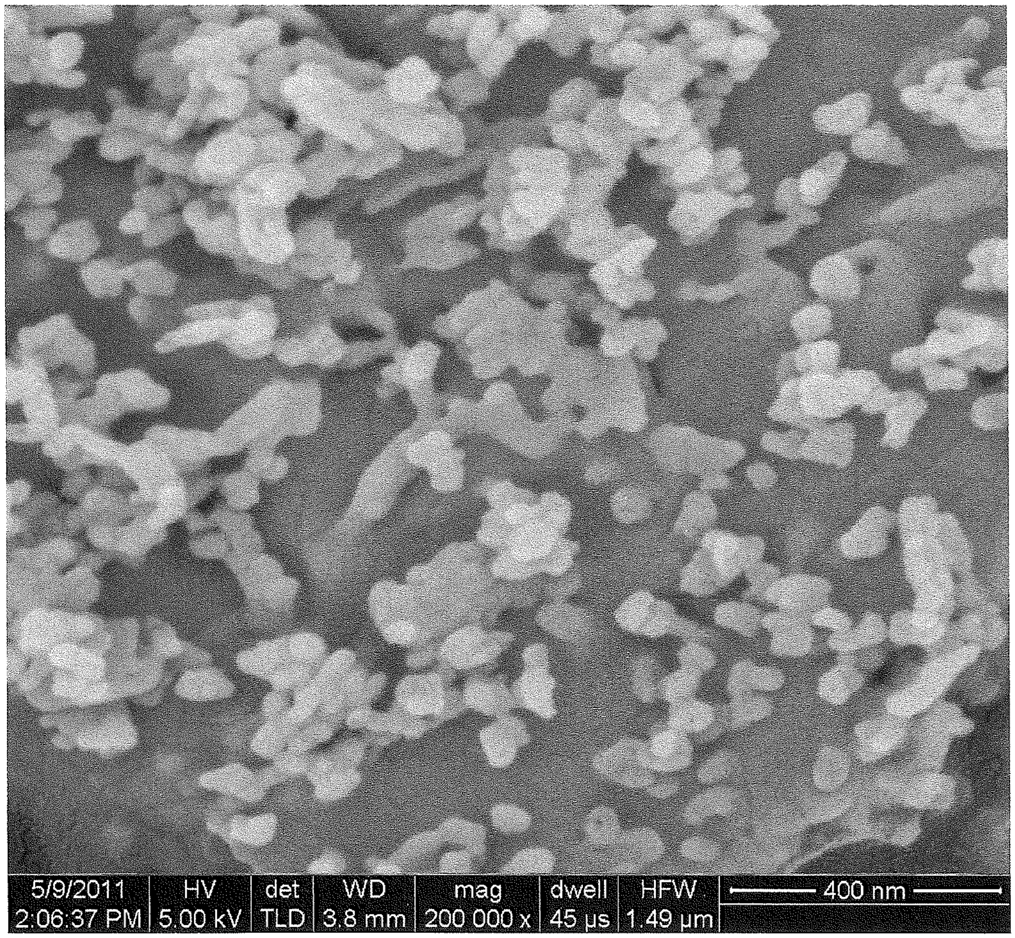
Figure 18:
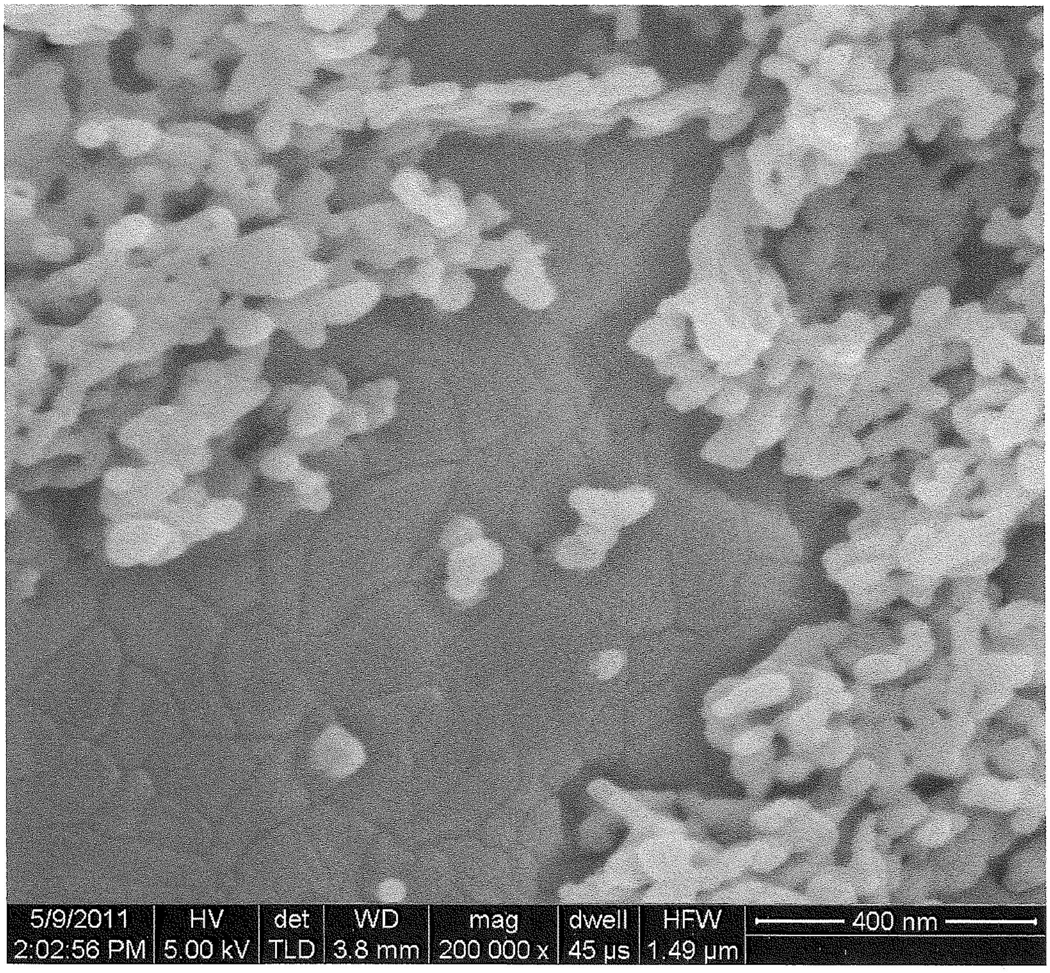
Figure 19:
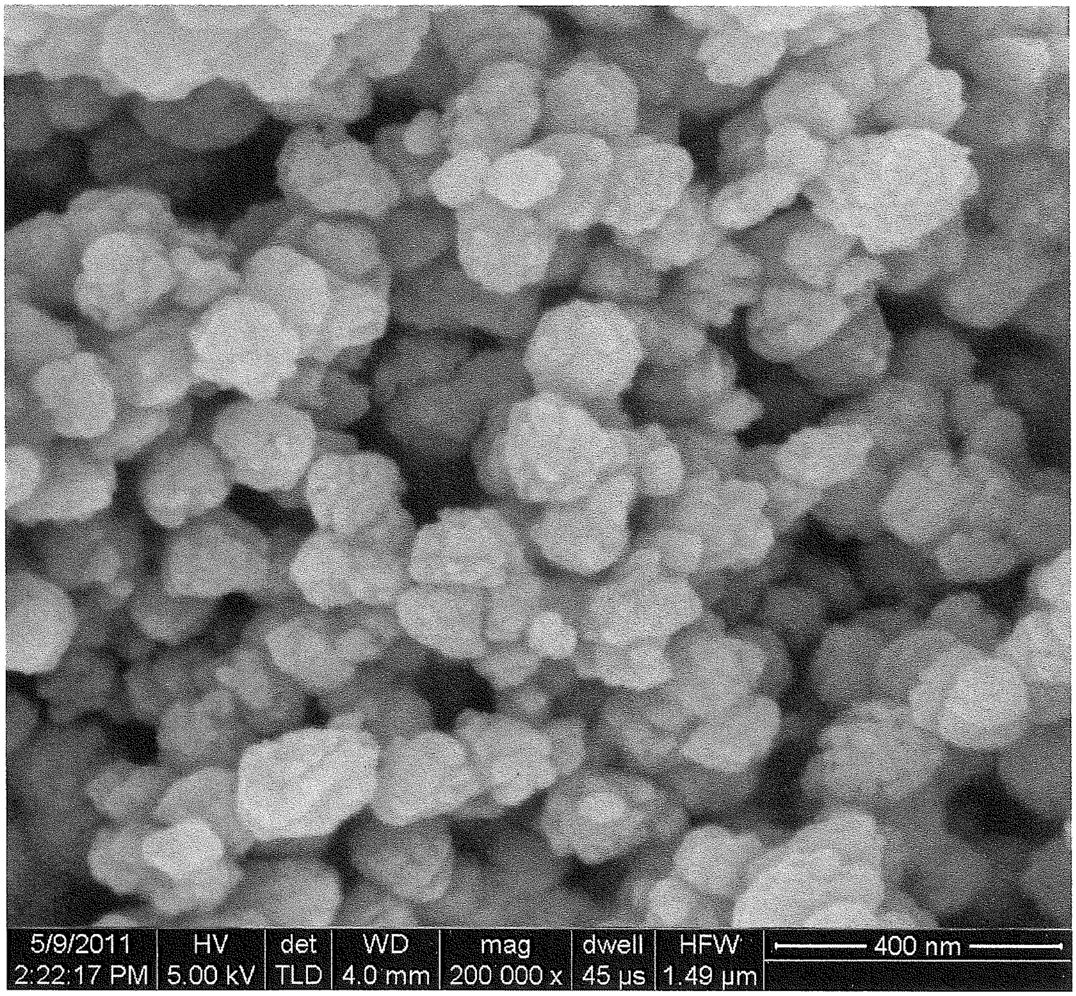
Figure 20:
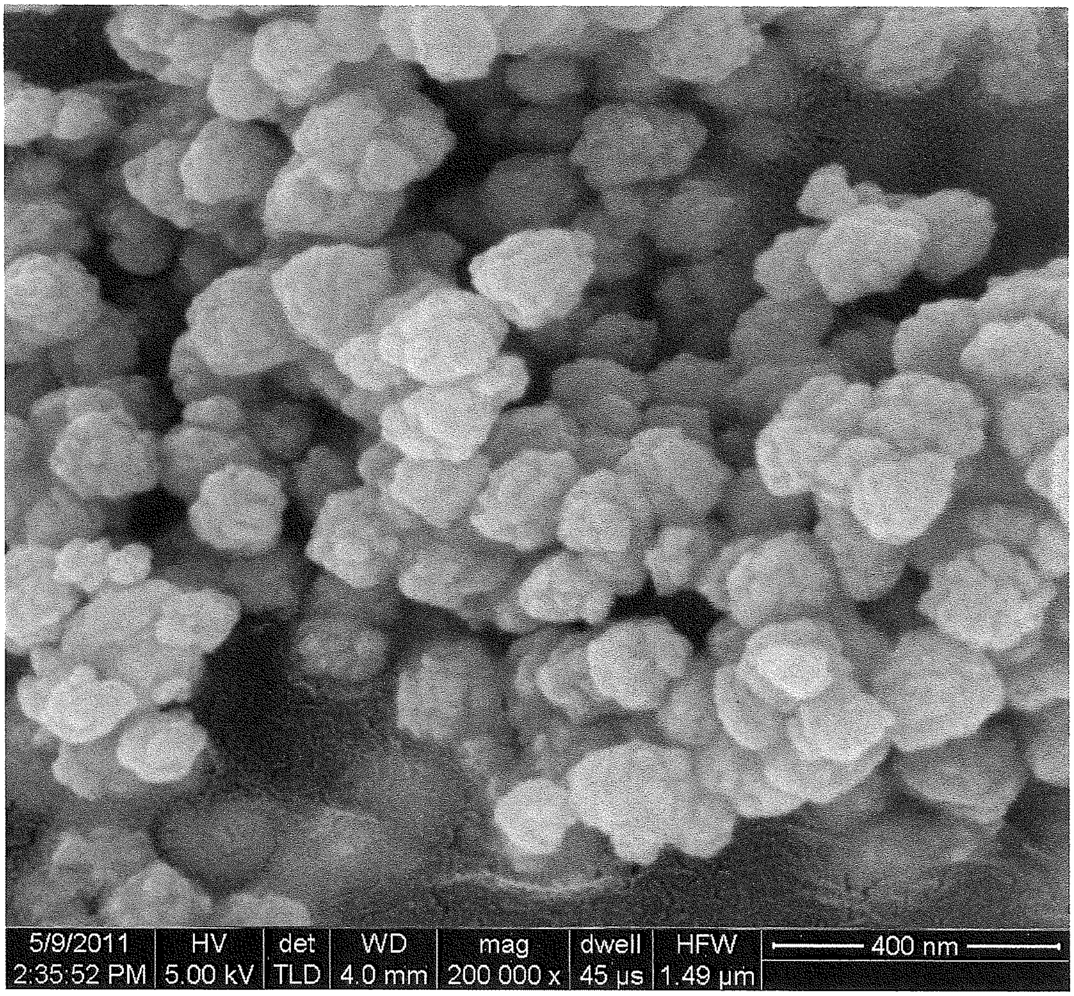

It is preferred that the amount of polymorph 037-0804 exceeds that of any other polymorph by weight. In one embodiment, the amount of polymorph 037-0804 is more than 50% of all polymorphs present and, in another embodiment, at least 90% of the polymorphs present of LDOC is $La_2O_2CO_3$. In another embodiment, polymorph 037-0804 ($La_2O_2CO_3$) is present in an amount of at least 95% by weight relative to other polymorphs and in still another embodiment, at least 99% by weight. It has also been determined that the phosphate binding kinetic of LDOC resulting from the present invention versus LDOC resulting from the process of the '782 patent are different as well. At a pH of 3 or below, phosphate binding for both materials was about the same. However, as shown in FIG. 10, at a pH of about 6.5 (a pH generally found in the intestines), the amount of phosphate bound in 60 minutes by the LDOC of the present invention was approximately 240 mg $PO_4$ bound per gram of compound where as that bound by LDOC produced in accordance with the '782 patent was only about 118 mg $PO_4$ bound per gram of compound. In one embodiment, therefore, the lanthanum oxycarbonate and, in another embodiment, the LDOC of the inventions have a binding kinetic at pH 6.5 at 60 minutes, of at least 150 mg $PO_4$ per gram of lanthanum oxycarbonate/LDOC. In another embodiment, the lanthanum oxycarbonate and LDOC of the invention have a binding kinetic of at least about 180 mg $PO_4$ per gram compound and in still a further embodiment, at least about 200 mg $PO_4$ per gram compound. The BET surface area of the material tested was 6-7 $m^2/g$ for RZB012 (lanthanum oxycarbonate in accordance with the '782 Patent) and was about 33.9 for $La_2O_2CO_3$ in accordance with the invention. Moreover, it is believed that the porosity, bulk density and flow characteristics of LDOC made in accordance with the present invention surpassed those made in accordance with the teachings of the '782 patent.

Figure 1B:
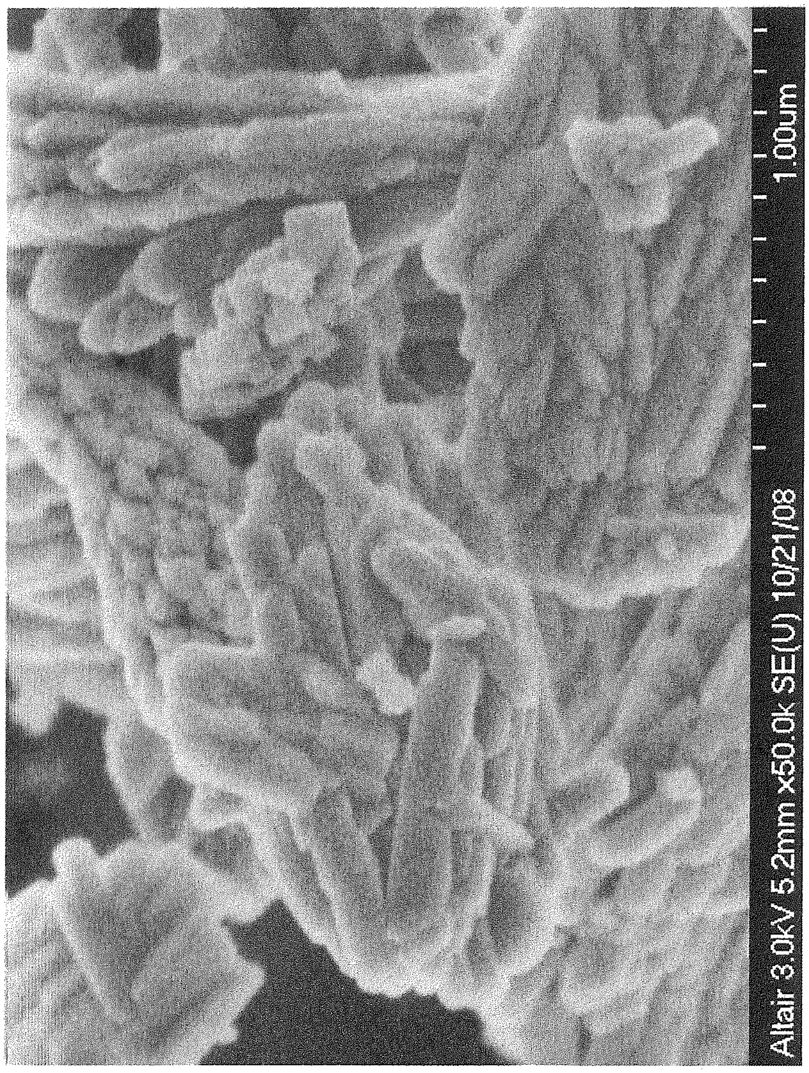
Figure 1C:
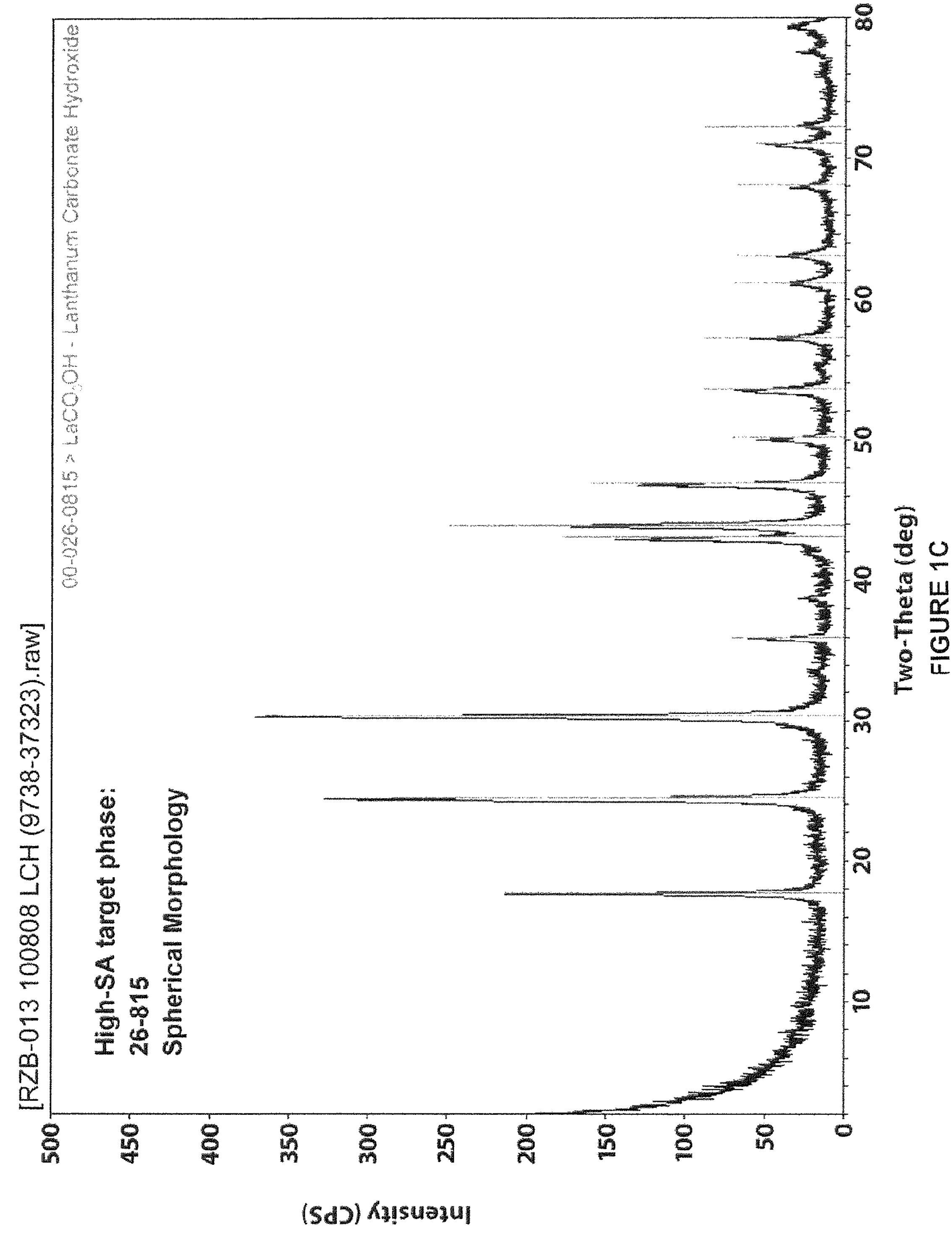
Figure 1D:
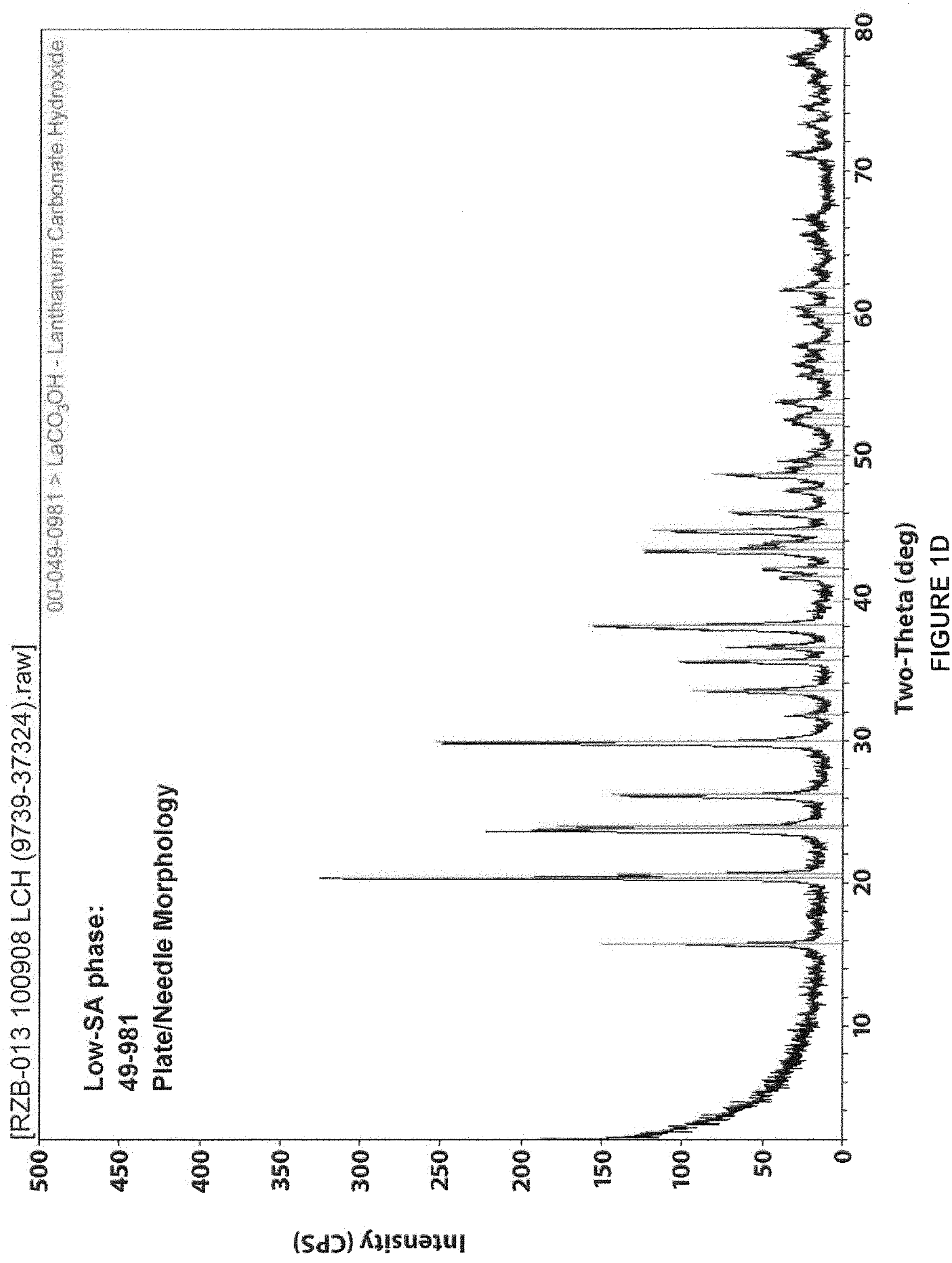

Aggregate size as described herein is either determined by scanning electron microscopy (SEM) or laser diffraction on a Coulter LS230. As can be seen in FIG. 1A, batch 100808 appears to have a fairly even 100-200 nm (0.1-0.2 μM) spherical appearance while the rod and plates of batch 100908 in FIG. 1B seem to be an order of magnitude higher. But these appear more aggregated.

However, the $D_{10}$, $D_{50}$ and $D_{90}$ by volume of the aggregates of batch 100808 each was 6.8, 47.0, and 114.0 μM, respectively. This is at odds with the visual images from SEM and again suggests aggregation.

The LCH and LDOC in accordance with the present invention are administered by oral delivery. Any oral delivery device or dosage form which is known may be used as long as it is consistent with the appropriate guidelines for pharmaceuticals. These include swallow tablets (tablets which are not meant to dissolve in the mouth but rather to be swallowed), swallow caplets, generally capsule shaped, compressed dosage forms, swallow hard gelatin capsules, swallow soft gel capsules, orally dissolvable tablets, orally dissolvable caplets, orally dissolvable hard gelatin capsules, orally dissolvable soft gelatin capsules, chewable tablets, chewable caplets, chewable capsules, powders, sprinkles, orally disintegrable films, foods, confections, gums, syrups, suspensions, emulsions or dispersions. Frequently, due to their renal problems, subjects with hyperphosphatemia need to limit their liquid intake. Therefore, formulations that can be taken with no or limited amounts of liquid are desirable. To this end, for example, a formulation in the form of, e.g., beads, chewed or crushed tablets, powder, or sieved granules that may be sprinkled on food are contemplated herein.

Methods of formulating the various dosage forms described herein are familiar to one of skill in the art, and may be produced employing conventional methods.

In addition to the active pharmaceutical ingredient or "API" (LCH or LDOC), dosage forms in accordance with the present invention may include other or secondary APIs as well. These may include other types of phosphate binders such as sevelamer hydrochloride sold under the trademark RENAGEL and lanthanum carbonate sold under the trademark FOSRENOL. These may be mixed with the LCH and/or LDOC or can be separated into layers or otherwise. In another embodiment, one or more dosage forms of the present invention can be taken with one or more dosage forms of RENAGEL, FOSRENOL or some other additional API (other than LCD or LDOC). These dosage forms can be taken together, such as with or after meals, or they can be taken even hours apart.

Other APIs that can be administered in addition to LCH and/or LDOC include, without limitation, systematically distributable pharmaceutical ingredients, vitamins, minerals, dietary supplements, as well as non-systemically distributable drugs. A combination or mixture of any of the foregoing is also contemplated by the present invention. Pharmaceutical ingredients may include, without limitation, antacids, analgesics, stimulants, sleep aids, hypnotics, antipyretics, antimicrobials, anxiolytics, laxatives, antidepressants, antidiuretics, antiflatuants, antispasmodics, anti-inflammatory, antibiotics, diuretics, anorexics, antihistamines, antiasthmatics, antidiuretics, antiflatuents, antimigraine agents, antispasmodics, sedatives, antihyperactives, antihypertensives, tranquilizers, decongestants, immunosuppressants, anticancers, antivirals, antiparasitics, antifungals, antiemetics, antidepressants, antiepileptics, local anesthetics, vasoactive agents, antiasthmatics, skeletal muscle relaxants, drugs for parkinsonism, antipsychotics, hematopoietic growth factors, antihyperlipidemics, anticoagulants, fibrinolytics, antithrombotics, hormones, therapeutic proteins and peptides, antiarrhythmia, antiangina, beta blockers and combinations thereof. Also included as API's in accordance with the present invention are the drugs and pharmaceutically active ingredients described in Mantelle, U.S. Pat. No. 5,234,957, in columns 18 through 21. That text of Mantelle is hereby incorporated by reference. In one embodiment in accordance with the present invention, the APIs are preferably pharmaceutical agents having a high likelihood of abuse by people. In another preferred embodiment of the present invention, the API is a pain medication such as an a narcotic or non-narcotic analgesic as listed on pages THER-2 and THER-3 of the Merck Index, 13th Ed., Published by Merck & Co., Inc., of Whitehouse Station, N.J., copyright 2001, which is hereby incorporated by reference. The narcotic analgesics include, but are not limited to, analgesics, pain relievers, opioids such as oxycodone, codeine, hydrocodone, morphine, hydromorphone, oxymorphone, methadone, propoxyphene, meperidine, fentanyl, buprenorphine, butorphanol, dezocine, levomethadyl acetate, levorphanol, nalbuphine, pentazocine, remifentanil, sufentanil, tramadol; Stimulants like amphetamine, methamphetamine, dexamphetamine, methylphenidate, dexmethylphenidate, pemoline; Sedative and hypnotics including barbiturates as amobarbital, aprobarbital, butabarbital, mephobarbital, phenobarbital, secobarbital; benzodiazepines such as alprazolam, clonazepam, diazepam, estazolam, flurazepam, halazepam, lorazepam, midazolam, quazepam, temazepam, triazolam, prazepam, oxazepam, other drug classes include modafinil and armodafinil. These will all be given in the amounts customarily administered.

As used in this disclosure, the term "vitamin" refers to trace organic substances that are required in the diet. For the purposes of the present invention, vitamin(s) include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K.

Also included within the term vitamin are the coenzymes thereof. Coenzymes are specific chemical forms of vitamins. Coenzymes that may be useful in the present invention include thiamine pyrophosphates (TPP), flavin mononucleotide (FMM), flavin adenine dinucleotive (FAD), Nicotinamide adenine dinucleotide (AND), Nicotinamide adenine dinucleotide phosphate (NADP), Coenzyme A (CoA), pyridoxal phosphate, biocytin, tetrahydrofolic acid, coenzyme $B_{12}$, lipoyllysine, 11-cis-retinal, and 1,25-dihydroxycholecalciferol. The term vitamin(s) also includes choline, carnitine, and alpha, beta, and gamma carotenes. As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA.

It is contemplated that the dosage forms in accordance with the present invention may also include at least one other ingredient or pharmaceutically acceptable excipient. This excipient may include, but is not limited to, taste masking agents, coatings, mass diluting agents, binders, fillers, sugars, sweetners, including artificial sweeteners, polymers, flavoring agents, coloring agents, lubricants, glidants, bio- or muco-adhesives, viscosity modifiers, surfactants, buffers, disintegrants, compression/encapsulation aids, plasticizers, slip/anti-electrostatic agents, etc. The amount of any one or more of these excipients will vary with, inter alia, the amount and type of API, API particle size, and shape of the dosage form, form of the dosage form, desired speed of release of active (e.g., within seconds or minutes after ingestion), desired location of release of active in the body, how many ingredients are used, which ingredients are used, the number of dosage forms that will make-up a dose, the amount of API(s) per dose and the like.

Taste masking agent(s) in accordance with the present invention include anything known to be used as a taste masking agents in this art. Preferred taste masking agents in accordance with the present invention may include Eudragit E-100, ethylcellulose, hydroxypropylmethylcellulose, hydroxypropyl cellulose, methylcellulose, Hydroxyethylcellulose, carboxymethylcellulose, shellac, zein, carbomers, and fats. Taste masking agents can be used in conventional amounts and preferably in an amount of about 1 to about 5% by weight of the total dosage form, and more preferably in an amount of about 2% to about 5% by weight of the total dosage form, and most preferably in an amount of about 2% to about 3% by weight of the total dosage form.

Binders can be anything known to be used as binders. These materials are used to add cohesiveness to powders and provide the necessary bonding to form granules that can be compressed into hard tablets that have acceptable mechanical strength to withstand subsequent processing or shipping and handling. Some binders that may be useful in the present invention include acacia, tragacanth, gelatin, starch (both modified or unmodified), cellulose materials such as methylcellulose, ethylcellulose, hydroxypropylmethylcellulose, hydroxypropyl cellulose, hydroxyethylcellulose and sodium carboxy methylcellulose, alginic acids and salts thereof, e.g., sodium alginate, magnesium aluminum silicate, polyethylene glycol, guar gum, xanthan gum, polysaccharide acids, bentonites, sugars, invert sugars, and the like, fats, waxes, carbopol, povidone, polyvinylpyrrolidone, polymethacrylate and other acrylic and vinyl-based polymers. Binders can be used in conventional amounts and preferably in an amount of about 0 by weight to about 50 and more preferably about 2 to about 10 percent by weight of the total dosage form.

Coating agents, where included, are typically present in a trace amount by weight. Nonlimiting examples of coating agents include cellulose phthalate, cellulose acetate phthalate, ethylcellulose, gellan gum, maltodextrin, methacrylates, methylcellulose, microcrystalline cellulose and carrageenan, shellac, sucrose and polyvinyl derivatives. Where a coating is used, it may be added, for example, to slow the disintegration of the tablet after administration (e.g., polymer coating) or to extend shelf life by shielding the tablet from picking up moisture.

Fillers can be anything known to be used as fillers. Some fillers that may be useful in the present invention include mannitol, dextrose, sorbitol, lactose, sucrose, and calcium carbonate. Fillers can be used in conventional amounts and preferably in an amount of about 0 to about 90, and more preferably about 10 to about 50.

A particularly preferred type of filler which may be used is sugars. Sugars that may be used in the present invention include sugar, sugar alcohols, ketoses, saccharides, polysaccharides, oligosaccharides and the like, as well as celluloses and modified celluloses.

Sugars may also include direct compression and/or nondirect compression sugars. Particularly preferred nondirect compression sugars include, without limitation, dextrose, mannitol, sorbitol, trehalose, lactose and sucrose. Of course, these sugars generally exist as either a direct compression sugar, i.e., a sugar which has been modified to increase its compressibility and/or flow, or a nondirect compression sugar which does not have sufficient flowability and/or compressibility to allow it to be used in high speed processing and multi-tablet presses without some sort of augmentation such as, without limitation, a glidant to increase flow, granulation to increase flow and/or compressibility and the like. Of course, techniques like granulation can also be used to convert something which initially has sufficient flow and compressibility to be considered a direct compression sugar before processing into a nondirect compression sugar as well. This can be measured by directly compressing tablets made only from a sugar and comparing the flow and compressibility both before and after processing. If flow and/or compressibility are reduced after processing the material is likely to have become a nondirect compression sugar. It will be appreciated however, that whether or not the reduction in properties are sufficient to require augmentation or further processing before the sugar is used in a commercial process will depend on a number of factors including the amount used, the type of processing equipment used, and the overall formulation. Generally, however, some further processing or augmentation is required. While not definitive, sometimes a nondirect compression sugar will have at least about 90% of its particles smaller than about 200 microns, and more preferably 80% smaller than about 150 microns.

The amount of total sugar can range from about 0 to about 90%. More preferably, the amount of sugar will range from about 5% to about 75%, and even more preferably between about 10% and 50%. Other non-carbohydrate diluents and fillers which may be used in accordance with the present invention include for example dihydrated or anhydrous calcium carbonate, anhydrous or hydrated calcium sulphate, and calcium lactate trihydrate. When used these are present in an amount of ranging from 0 to about 90%, more preferably from about 5% to about 75% and most preferably from about 10% to about 50% by weight of the dosage form.

Sweeteners for use with the formulations of the present invention include, e.g., fructose DC; honey DC; maltodextrin; maltose DC; mannitol DC; molasses DC; sorbitol, crystalline; sorbitol, special solution; and, sucrose DC. These may be used in conventional amounts.

Artificial sweeteners may also be used and can be anything known to be used as artificial sweeteners. Some artificial sweeteners that may be useful in the present invention without limitation include saccharin, aspartame, aspartame and lactose, aspartame dextrose, sucralose, neotame, and acesulfame potassium. Artificial sweeteners may be used in conventional amounts, and preferably in an amount ranging from about 0.1% to about 2%.

Flavoring agents can be anything known to be used as flavoring agents. Flavoring agents that may be useful in the present invention may include synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavoring agents are vanilla, citrus oil, including lemon, orange, banana, grape, lime and grapefruit, and fruit essences, including apple, pear, peach, strawberry, raspberry, cherry, plum, pineapple, apricot and so forth.

Flavoring agents may be used in conventional amounts, and preferably in an amount ranging from about 0.01% to about 3% by weight of the dosage form, and more preferably from about 0.1% to about 2.5% by weight of the dosage form, and most preferably from about 0.25% to about 2% by weight of the dosage form.

Coloring agents can be anything known to be used as a coloring agent. Coloring agents useful in the present invention may include titanium dioxide, and dyes suitable for food such as those known as F.D.& C. dyes and natural coloring agents such as grape skin extract, beet red powder, beta-carotene, annatto, carmine, turmeric, paprika, etc. Coloring agents may be used in conventional amounts, and preferably in an amount ranging from about 0.001% to about 1% by weight of the dosage form.

Lubricants can be anything known to be used as a lubricant and include, for example, glycerol palmitostearate, magnesium stearate; stearic acid; calcium stearate; alkaline stearate; talc; and, sodium stearyl fumarate. Lubricants that may be useful in the present invention may include intrinsic or extrinsic lubricants. Intrinsic lubricants may include magnesium, calcium, zinc salts of stearic acid, hydrogenated and partially hydrogenated vegetable oils, animal fats, polyethylene glycol, polyoxyethylene monostearate, talc, light mineral oils, sodium benzoate, sodium lauryl sulphate, magnesium oxide and the like. Powder lubricants may also be used; nonlimiting examples of powder lubricants include glyceryl behenate. Lubricants may be used in conventional amounts, and preferably in an amount from about 0.1% to about 5% by weight of the dosage form, from about 0.1% to about 3.0% by weight, more preferably from about 0.25% to about 2.5% and most preferably from 0.5% to 2%.

Viscosity modifiers can be anything known to used as a viscosity modifier. Some viscosity modifiers that may be useful in the present invention include, without limitation, sodium alginate, hydroxypropyl methylcellulose (HPMC), hydroxyethylcellulose (HEC), sodium carboxymethycellulose (sodium CMC), polyvinylpyrrolidone (PVP), Konjac flour, carrageenan, xanthan gum, other hydrophilic polymers, or mixtures thereof. Viscosity modifiers can be used in conventional amounts and preferably in an amount of about 1% to about 40%, and more preferably in an amount of about 2% to about 20% by weight of the dosage form.

Surfactants can be anything known to be used as surfactants. Some surfactants that may be useful in the present invention include, without limitation, various grades of the following commercial products: Arlacel®, Tween®, Capmul®, Centrophase®, Cremophor®, Labrafac®, Labrafil®, Labrasol®, Myverol®, Tagat®, and any non-toxic short and medium chain alcohols. Surfactants can be used in conventional amounts and preferably in an amount of about 0.01% to about 5%, and more preferably in an amount of about 0.1% to about 2% by weight of the dosage form.

Buffers can be anything known to be used as a buffer. Some buffers that may be useful in the present invention include any weak acid or weak base or, preferably, any buffer system that is not harmful to the gastrointestinal mucosa. These include, but are not limited to, sodium carbonate, potassium carbonate, disodium hydrogen phosphate, sodium dihydrogen phosphate, and the equivalent potassium salts. Buffers can be used in conventional amounts and preferably in an amount of about 0.1% to about 10%, and more preferably in an amount of about 1% to about 5% by weight of the dosage form.

Disintegrants which may be used include starch, cellulose, modified starch, microcrystalline cellulose, alginic acid, clays, veegum and super disintegrants including, without limitation, cross-linked PVP, croscaramellose salts such as croscaramellose sodium, starch derivatives like sodium starch glycolate, Where such super disintegrants are used, they are traditionally found in an amount of between about 1% and about 20%, more preferably between about 2% and about 10%, and most preferably between about 2% and about 5% by weight of the finished dosage form. In addition to, instead of any portion of, or instead of any super disintegrant, the dosage forms in accordance with the present invention may include at least one effervescent couple or disintegrant. These disintegrants may comprise up to about 20 weight percent and preferably between about 2% and about 10% of the total weight of the dosage form.

Specific disintegrants which may be used include, e.g., crosslinked vinylpyrrolidones (e.g., POLYCLAR AT®), crosslinked carboxymethylcelluloses, crosslinked croscarmelloses (e.g., ADDISOL®), carboxymethylamidons (e.g., AMIGEL®); crospovidone; gellan gum; L-HPC; sodium starch glycolate; and starch DC. These disintegrants, where included, are typically present in an amount between about 0.5 and about 15 percent by weight.

If desired, the dosage form may also contain minor amounts of nontoxic substances such as wetting or emulsifying agents, pH buffering agents and the like, for example, sodium acetate, sorbitan monolaurate, triethanolamine, sodium acetate, triethanolamine oleate, sodium lauryl sulfate, dioctyl sodium sulfosuccinate, polyoxyethylene sorbitan fatty acid esters.

Compression agents/encapsulation aids, where included, are typically present in an amount between 2 and 20% by weight. Nonlimiting examples of compression agents/encapsulation aids include, for example, microcrystalline cellulose (e.g., AVICEL®); PVP of molecular weight 10,000 to 30,000; calcium carbonate; dextrose; fructose; fructose DC; honey DC; lactose anhydrate; lactose monohydrate; lactose and aspartame; lactose and cellulose; lactose and microcrystalline cellulose; maltodextrin; maltose DC; mannitol; microcrystalline cellulose and guar gum; microcrystalline cellulose and lactose; molasses DC; sorbitol, crystalline; starch DC; and, sucrose.

Nonlimiting examples of plasticizers include: dibutyl sebacate; and, polyvinylacetate phthalate.

Slip/anti-electrostatic agents, where included, are typically present in an amount between 0.1 and 2.0 percent by weight.

Non-limiting examples of slip/anti-electrostatic agents include, for example, colloidal silicas (e.g., AEROSIL® 100/200).

In addition to the methods of treatment of a subject comprising the use of pharmaceutical formulations of lanthanum compounds disclosed herein, in further embodiments, it is also contemplated herein that LCH and/or LDOC in accordance with the present invention may be therapeutically provided to a subject as part of a food or a dietary supplement. This can be a food, confection or beverage to be consumed by a human or animal, and may be formulated in a nutritional bar or into a drink, e.g., as many fiber source products are, to aid with ingestion. In such an instance, food may be considered an excipient herewith.

For example, LCH and/or LDOC can be formulated in a dry cat food (or that of any other domesticated mammal) in a defined ratio. Animal food products including LCH and/or LDOC can be produced as described in U.S. Patent Appln. Publication No. 2009/0317352, the entire text of which is hereby incorporated by reference.

Typical dog foods contain a protein source, such as chicken, beef, lamb, chicken meal or lamb meal. Preservatives, e.g., tocopherols, BHT and BHA, are also usual ingredients. Other ingredients may include corn, rice and bone meal. Typical cat foods may include, for example, fish meal, fish, egg product, beef, chicken, rice, corn gluten meal, poultry by-product meal, wheat flour, beef tallow, and corn. Horse food often contains ingredients such as maple syrup, honey, apple, flaxseed, flaxseed meal, rice bran and germ, oats, barley, corn, and wheat bran.

Thus, compositions of the present invention include compositions which may typically include a phosphate binder in combination with domestic animal food. The combination may take any suitable form. For instance, it may be in the form of particles, grains, pellets, etc. that contain the phosphate binder and the domestic animal food. Alternatively, it may be in the form of a simple physical admixture of the components, e.g., mixing the phosphate binder with the domestic animal food. Another form would involve sprinkling a composition including the phosphate binder onto domestic animal food. One could then mix it before serving it to the animal.

In view of the above, the following are contemplated as included among the exemplary compositions of the present invention include a particle, grain or pellet including a lanthanum oxycarbonate or lanthanum carbonate hydroxide and domestic animal food including at least one of the following ingredients: chicken, beef, lamb, chicken meal or lamb meal, tocopherols, BHT and BHA, corn, rice, bone meal, fish meal, fish, egg product, beef, beef meal, corn gluten meal, poultry by-product meal, wheat flour, beef tallow, maple syrup, honey, apple, flaxseed, flaxseed meal, rice bran and germ, oats, barley, and wheat bran.

In one embodiment, when lanthanum oxycarbonate or lanthanum carbonate hydroxide is administered as a phosphate binder, the amount administered to the domestic animal during a single administration typically ranges from about 1.0 to about 100 mg/kg body weight. Oftentimes the amount ranges from about 30.0 to about 80 mg/kg body weight. In certain cases the amount of administered lanthanum oxycarbonate ranges from about 40.0 to about 75.0 mg/kg body weight. Suitable ranges may vary depending on the subject and nature of condition to be treated, and are easily discerned by one of skill in the art.

Thus, in view of the above, the methods of the present invention also include a method comprising at least the step of providing a domestic animal with a composition of the present invention in an ingestible form. The invention also relates to a method which comprises at least the following steps: 1) mixing a lanthanum binding compound with domestic animal food; and, 2) providing the mixture to a domestic animal in an ingestible form.

LCH and LDOC-containing dosage forms for human or animal use may be produced by conventional technology using the API and the various excipients described herein. Examples of lanthanum containing oral dosage forms, for example, may be found in Murrer et al., U.S. Pat. No. 5,968,976, which issued Oct. 19, 1999, and specifically column 5, line 8 through column 6, line 6 thereof, which is hereby incorporated by reference; U.S. Pat. No. 7,381,428 to Ferdinando et al., entitled Stabilized Lanthanum Carbonate Compositions, which issued on Jun. 3, 2008, and specifically the examples at column 11, line 54 through column 13, line 59, which is hereby incorporated by reference; and Haslam et al., U.S. Pat. No. 7,465,465 entitled Pharmaceutical Formulation Comprising Lanthanum Compounds, issued Dec. 16, 2008, and specifically column 1, line 35 through column 3, line 35; and column 5, line 5 through column 7, line 2; and column 8, line 53 through column 9, line 44, the text of which is also incorporated by reference herein. The foregoing all describe various dosage forms and methods of producing same and are specific to lanthanum compounds, although not the lanthanum compounds in accordance with the present invention. Nonetheless, they would make suitable vehicles.

Because of the discovery that the LDOC of the present invention provides superior performance, even over LDOC produced through other methodology, in terms of phosphate binding kinetics at relatively higher pH, it may be desirable to ensure release of LDOC in accordance with the present invention once a dosage form (or what remains after it has been swallowed and processed in the stomach) clears the stomach and enters the intestinal tract. In the intestinal tract, the pH generally begins to increase and can range from around 4 to around 8 in healthy patients. By controlling release of at least some LDOC in accordance with the present invention such that it occurs in the intestinal tract, there is a greater chance that phosphates released while food is being digested in the intestine is efficiently bound. Thus, it is contemplated that the present invention includes controlled release dosage forms of the lanthanum compositions disclosed herein.

Controlled release dosage forms, including but not limited to, delayed, extended or sustained release dosage forms, are well known to those of skill in the art and may be made according to conventional methods employing, e.g., tablet-coating compositions, plasticizers, semipermeable membranes, pH independent and/or pH independent coating layers, film-forming polymers, etc. Typically, release modification may be successfully achieved through the use of enteric coatings. A number of different types of compounds suitable for use as enteric coatings are known in the art and include, for example, EUDRAGIT polymers (Evonik Röhm GmbH, Darmstadt, Germany). See generally Remington's Pharmaceutical Sciences, $18^{th}$ Edition, 1990; U.S. Pat. No. 7,883,722; U.S. Pat. No. 7,790,755; U.S. Pat. No. 7,879,362 and references cited therein, the contents of all of which are fully incorporated by reference herein. In one embodiment, the release of at least a portion of the compounds of the present invention is delayed until it reaches a location in the digestive tract where the pH is 4.5 or above.

The lanthanum-based compounds of the invention can be formulated to provide for a reduced pill burden relative to other phosphate binders. The formulation is typically characterized in that in may be swallowed without chewing or by being chewed. Formulations of the present invention may include the following: diluting agents; binders; coatings;

compression/encapsulation aids; disintegrants; lubricants; plasticizers; slip/anti-electrostatic agents; powder lubricants; and, sweeteners such as described hereinabove.

Where the formulation is in the form of a tablet, it typically has a volume between about 0.3 $cm^3$ and about 1.2 $cm^3$, preferably between about 0.35 $cm^3$ and about 0.50 $cm^3$. Each tablet typically includes enough phosphate binder such that only 3 or less tablets need to be ingested each day for a patient suffering from a condition associated with an abnormally elevated level of phosphate in the blood, e.g., chronic kidney disease (CKD) and various stages thereof; more particularly chronic renal insufficiency (CRI), or End Stage Renal Disease (ESRD) or general kidney failure.

As contemplated herein, the tablet for use according to the methods of the present invention may typically provide for rapid disintegration in the stomach after ingestion. For example, desired disintegration time in the stomach may be less than 30 seconds. In certain cases, the disintegration time may be 20 seconds or less. However, transit of the dosage forms of the present invention through the stomach for delivery to the small intestine is also contemplated. As understood by one of skill in the art, delivery in this manner may be achieved by formulating a controlled release dosage form according to conventional methods and as described herein.

Ideally, a dosage form of the present invention (e.g., a tablet) exhibits a substantially longer shelf-life than other phosphate binding formulations. For instance, even after a period of 2 years, the tablet typically should not increase in volume more than 5 percent, preferably 2.5 percent, more preferably 1 percent.

As described herein, one of the known indications for lanthanum compounds is to treat subjects having an abnormally elevated level of phosphate in the blood. As used herein, an abnormally elevated level of phosphate in the blood" refers to above about 4.5 mg phosphate/dL; a normal level may range from about 2.4-4.5 mg phosphate/dL. Thus, one of the known indications for lanthanum compounds is hyperphosphatemia, which as used herein, refers to a condition of a patient having blood phosphate levels of above about 4.5 mg/dL.

Subjects susceptible to or suffering from hyperphosphatemia, suffering from or at risk for chronic kidney disease (CKD), susceptible to or suffering from soft tissue calcification associated with chronic kidney disease, susceptible to or suffering from secondary hyperparathyroidism, or susceptible to or suffering from other yet undiscovered conditions requiring control of phosphate absorption or otherwise associated with or resulting from an abnormally elevated level of phosphate in the blood can be treated by the administration of a therapeutically effective amount of the LCH or LDOC in accordance with the present invention.

Hyperphosphatemia in such subjects has several secondary effects. When a subject suffers from hyperphosphatemia, excess serum phosphate precipitates serum calcium causing widespread ectopic extraskeletal calcification. Unwanted calcium deposits can occur in cardiovascular tissue, resulting in an increased risk of cardiovascular complications that often lead to death. Additionally, increased serum phosphate decreases intestinal calcium absorption. These two mechanisms work concurrently to reduce serum calcium levels.

A reduction in serum calcium levels can contribute to an increase in the production of parathyroid hormone (PTH) and to the development of secondary hyperparathyroidism. Furthermore, recent studies show that high phosphate levels can stimulate PTH production directly and lead to secondary hyperparathyroidism. Continual stimulation of PTH secretion induces hyperplasia of the parathyroid gland and may lead to a parathyroidectomy becoming necessary.

It is believed that the method of the present invention involving the administration of a stabilized LCH and/or LDOC formulations not only reduces plasma phosphate levels, but ameliorates the effects of CKD in subjects susceptible to or having this condition, including, e.g., hyperphosphatemia, ectopic extraskeletal calcification, serum hypocalcemia, and secondary hyperparathyroidism. It should however, be understood that this invention is not limited to any particular biochemical or physiological mechanism.

Subjects susceptible to or suffering from hyperphosphatemia can be treated by administering a therapeutically effective amount of a stabilized lanthanum carbonate formulation of the invention.

As indicated above, the subject treated according to the methods of the present invention may be at risk for CKD, or have any of stages one to five of CKD, the clinical characteristics of such stages being familiar to one of skill in the art. To that end, similar pathological conditions are also known in the art as chronic renal insufficiency, end stage kidney disease and general kidney failure and treatment of such conditions are contemplated herein.

Subjects at risk for CKD or who have any of stages one to five of CKD who may be treated may have one or more of the following symptoms: a blood phosphate level of above about 4.5 mg/dL, a plasma creatinine concentration of above about 1.6 mg/dL, a BUN of above about 20 mg/dL, any detectable amount of blood in the urine, a urine protein concentration above about 100 mg/dL, a urine albumin concentration above about 100 mg/dL, an intact parathyroid hormone concentration in the blood above about 150 pg/mL, an abnormal GFR, or combination thereof.

In addition, the present methods and lanthanum compounds may be utilized to prevent the progression of renal pathology, e.g., by treating a subject displaying one or more symptoms of stage one CKD to prevent the development of CKD in the subject or by treating a subject having stage one CKD to prevent progression of the disease to stage two CKD, and so on.

A subject having a symptom or symptoms of CKD may also be treated for calcification of soft tissue associated with CKD by administering to the subject a therapeutically effective amount of an LCH and/or LDOC formulation of the present invention. Calcification can occur in any soft tissue. Soft tissue can include arterial tissue, cardiac muscle, heart valves, joints, skin and breast tissue.

A subject suffering from or having one or more symptoms of secondary hyperparathyroidism can be treated by administering to the subject a therapeutically effective amount of an LCH and/or LDOC of the present application.

Hyperparathyroidism is defined as a disease in a subject having an intact PTH level of about 150 pg/mL or greater. The symptoms of hyperparathyroidism include hypocalcaemia (i.e., a blood calcium level below about 8.5 mg/dL), hyperphosphatemia (i.e., a blood phosphate level of above about 4.5 mg/dL), and bone disorders (e.g., bone fractures or bone pain).

As used herein, an effective amount of the lanthanum carbonate compounds of the present invention refers to an amount that can reduce the phosphate level in a subject to a clinically significant degree as determined by a medical professional. As understood herein, the desired target blood phosphate level for a particular subject administered a pharmaceutical composition of the present invention may be determined and monitored over time by a person of skill in the medical arts such that hyperphosphatemia as well as hypophosphatemia (e.g., blood levels of about 2.4 mg/dL or less) or other undesirable side effects are avoided.

The LCH and/or LDOC formulations of the invention can be orally administered to subjects in accordance with this invention in dosage forms varying from about 125 to about 20,000 mg of API calculated based on the weight of elemental lanthanum. These can be administered with every meal (or immediately before or after a meal), e.g., up to four times a day, depending on the subject's needs and the type of dosage form. If delayed or other controlled release strategies are used, only a single dose may be required once a day or two doses 12 hours apart. A typical effective dosage amount for an adult can be, e.g., from between about 200 to about 12,000 mg per day, or from between about 500 mg to about 8000 mg daily. The dosage may also be from between about 300 to 4000 mg/day.

The dose can thus be divided and administered with each meal, for, example, in the form of a pharmaceutical composition wherein the effective amount of one or more of the lanthanum carbonate compounds is selected from the group consisting of from about 100, 125, 150, 250, 500, 750, or 1000 mg, e.g., administered three times per day. Serum plasma levels can be monitored weekly and dosages can be modified until an optimal serum phosphate level is reached, e.g., as determined by the subject's clinician. Administration may be conducted in an uninterrupted regimen; such a regimen may be a long term regimen, e.g., a permanent regimen, for treating chronic conditions.

In view of the likelihood that a pharmaceutical formulation of the present invention may need to be administered for an extended amount of time, e.g., to treat a chronic kidney condition, kits comprising the lanthanum compounds of the present invention designed to facilitate and/or enhance patient compliance are contemplated herein. For example, such kits may comprise one or more conveniently prepackaged and/or pre-dispensed pharmaceutical dosage forms comprising the lanthanum compounds disclosed herein, conveniently set aside in the kit or otherwise identified therein in the proper quantity for administration at a particular time of day, e.g. meal times, so as to provide an increased level of convenience for the patient and thus enhance patient compliance. Prescribing information or other instructions for use may also be provided therein.

As contemplated herein, BET surface area of the lanthanum compounds disclosed herein may be determined as provided in U.S. Pat. No. 7,588,782.

Laser particle size data can be produced using, for example, a LS230 Laser Particle Size Analyzer manufactured by Coulter.

Average the runs using the LS230 software and have the software calculate the desired volume D results (i.e. for D1, D10, D50, D90, and D99).

The Refractive Index (RI) of a solid is required to perform an accurate laser PSD analysis for particles under 1 μm. The RI of the test materials were not listed in literature at the time this method was developed. Testing has shown that adjusting the RI from 1.9 to 2.3 did not visibly affect the PSD. Therefore an RI of 2.1 was chosen.

Phosphate binding kinetics and binding capacity as illustrated in FIG. 10 as described herein (particularly with regard to RZB-012) can be measured as follows:

Apparatus:

Four-place analytical balance pH meter w/temperature compensation and appropriate probes Stirrer w/impeller Hot plate w/temperature control Thermometer (capable of reading 37° C.)

Magnetic stir plate

Magnetic stir bars (1½" to 3" long)

Pyrex beakers (250 to 1500 ml)

Glass volumetric flask (100 to 1000 ml)

Graduated cylinders (100 to 1000 ml)

Digital timer

Tachometer 10 ml sample tube rack 10 ml plastic sample tubes w/caps

Automatic diluter 10 ml plastic syringes w/plunger 0.2 μm syringe filter (20 to 25 mm diameter)

Pipettes (0.1 to 1 ml auto)

ICP-OES

Reagents

De-ionized water (at least 16 MΩ)

pH buffers (1, 3, 7)—Follow the manufacturers' calibration instructions. Bracket the anticipated pH range using the appropriate buffers. Do this daily before doing any part of the procedure below.

Concentrated Hydrochloric Acid

Stock ~0.15M HCl

1. Add 12.5 ml of concentrated Hydrochloric Acid to 987.5 ml of D.I. Store for up to 1 year in a sealed plastic container Sodium Hydroxide Stock ~0.15M NaOH 1. Add 6 g of Sodium Hydroxide to a 1.0 L glass volumetric flask
2. Add 500 ml D.I. and shake to dissolve salts
3. Fill with D.I. to 1.0 L mark and mix thoroughly
4. Store for up to 1 year in a sealed plastic container Sodium Chloride (NaCl)

Anhydrous Sodium Phosphate Dibasic ($Na_2HPO_4$)

Stock phosphate solution (0.00527 mol PO43—per Liter—500 mg PO43—per Liter)

1. Place a 3" magnetic stir bar in the bottom of a 4.5 L Pyrex beaker and add 3.8 L of D.I.
2. Place on a magnetic stir plate
3. Into a clean weighing vessel weigh 2.99 g of Anhydrous Sodium Phosphate Dibasic
4. Into a different clean weighing vessel weigh 0.462 g of Sodium Chloride
5. Quantitatively transfer the $Na_2HPO_4$ and NaCl to the stirred 4.5 L Pyrex beaker
6. Use a properly calibrated pH meter to monitor the pH of the solution
7. Drop wise add either the stock 0.15M HCl or stock 0.15M NaOH and adjust to the pH required for the test. It is OK to overshoot the pH but add more stock 0.15M HCl or stock 0.15M NaOH to readjust.
8. pH is stable if there is no more than 0.01 pH unit drift in 5 minutes.
9. Dilute to 4.0 L using D.I. and mix thoroughly
10. Store for up to 1 month in a sealed glass container Phosphate calibration standard (10,000 mg/L)

Multi-element check standard containing phosphorus OR independent Phosphate calibration standard (1,000 mg/L)

Lanthanum compound

Procedure:

Bench Top Preparation:

1. Determine the number of grab samples for the test and label an appropriate number of plastic sample tubes
2. Place the plastic sample tubes in a rack and set aside
3. Using a graduated cylinder measure out 1.0 L of the stock phosphate solution 4. Add the phosphate solution to a 1.5 L Pyrex beaker. The beaker should be sufficiently large to contain the phosphate solution and allow for a 30% volume increase
5. Run at ambient-20° C. or 37° C. as indicated in the analytical request. If 37° C. is requested place the 1.5 L beaker containing the 1.0 L of test solution on a temperature controlled hot plate. Set temperature to 37° C. Do not begin testing until the temperature has been achieved.
6. Stir the solution constantly using an electric stirrer equipped with an impeller. Stir rate should be ~180 rpm (verify with tachometer).
7. Using a 10 ml syringe remove 5 mls of solution and dispense it into a labeled sample tube. This is the T=0 sample
8. Simultaneously add the slug to the stirring beaker and start the digital timer.
9. Begin taking grab samples at the pre-described time intervals using the following protocol:

a. Rinse a 10 ml syringe with slurry from the stirring beaker and add washings back into the beaker
b. Suck up 5 ml of slurry using this same 10 ml syringe
c. Place a 0.2 μm syringe filter firmly on the tip and dispense 2 ml back into the stirring beaker
d. Dispense the remaining 3 ml into a labeled sample tube
e. Cap the tube and prepare for the next sample 10. If constant pH is required:

a. Between grab samples adjust pH using a 0.5 ml auto pipette
b. Adjust using appropriate titrant, 0.15M NaOH or 0.15M HCl, to maintain pH
c. Add as many 0.5 ml aliquots as it takes to maintain a constant pH. Take note of the number of aliquots
d. Record total volume added for each period of time between grab samples 11. Continue taking samples and maintain pH throughout duration of test
12. When test is completed clean all glass ware thoroughly and rinse with D.I.

Sample Preparation and Standard Curves and QC Sample:

13. Dilute samples 1:10 in a 10% HCl matrix a. Dilute to mark with D.I. and mix thoroughly. Store for up to 2 months in a sealed plastic container 14. Dilute an independent check standard so that the phosphorus concentration is bracketed by the standard curve values
15. Include a matrix blank with the submittal Sample Analysis Using an ICP-OES:

16. Allow for instrument warm-up as per manufacturers' instructions
17. Prepare a Standard Curve of 0, 5, 10, 20 mg/L:

a. 0 mg/L—is the matrix blank for 10% HCl
b. 5 mg/L—Aliquot 0.5 ml of a 1,000 mg/L certified aqueous standard into a 100 ml glass volumetric flask containing 10 mls of concentrated HCl and 50 ml of D.I. Dilute to mark with D.I. and mix thoroughly. Store for up to 2 months in a sealed plastic container
c. 10 mg/L—Aliquot 1.0 ml of a 1,000 mg/L certified aqueous standard into a 100 ml glass volumetric flask containing 10 mls of concentrated HCl and 50 ml of D.I. Dilute to mark with D.I. and mix thoroughly. Store for up to 2 months in a sealed plastic container
d. 20 mg/L—Aliquot 2.0 ml of a 1,000 mg/L certified aqueous standard into a 100 ml glass volumetric flask containing 10 mls of concentrated HCl and 50 ml of D.I.

18. Analyze samples, qc controls, and blank for phosphorus using the 214 nm wavelength. The standard curve of 0, 5, 10, 20 mg/L is linear for ICP at the 214 nm wavelength. RSD should be greater than 0.9995

Calculations:

$$R(\text{mg/L})=[A-B]\times C/D \text{ where: } R=\text{Result (mg/L)}$$

A=ICP reading (mg/L)
B=ICP reading (mg/L) for matrix blank
C=Dilution (ml)
D=Aliquot (ml)

Graph R (mg/L) vs Time (min). This graph can be compared to other graphs prepared using the same protocol. The surface of certain lanthanum compounds as well as lanthanum ions bind phosphate in solution. For the best comparison of relative binding efficiencies for different lanthanum compounds the amount of lanthanum added to the test should be the same. The calibration curve should be prepared using a National Institute of Standards and Technology (NIST) certified aqueous AAS standard. The quality control check can be either an independent AAS standard or a NIST certified mixed anion standard containing phosphorus. ICP spectra for the mixed anion standard should be checked to verify that none of the additional anions present interfere with the 214 nm phosphorus line.

Environment: All acidic solutions should be disposed of in an environmentally responsible manner. Neutralize and verify that metals concentrations are below city discharge limits.

Notes: Lanthanum carbonate is soluble in acid. Clean residue from glassware using acid.

References: This test is a variation of the test cited in the US patent by Anormed. U.S. Pat. No. 5,968,976—"Pharmaceutical composition containing selected lanthanum carbonate hydrates" hereby incorporated by reference for its teachings of these analytical methods.

Bulk density in accordance with the invention can be determined by standard methods.

Hypothetical Example:

Graduated Cylinder Tare Weight was determined to be 225 g. 75 grams of sample was sieved into the graduated cylinder. The Gross Weight was determined to be 299.4 g. The volume of this sample was measured to be 141 mL. Thus, the Bulk Density of the powder is:

$$\text{Bulk Density (g/cc)}=(299.4-225)/141=74.4/141=0.5277 \text{ g/cc}$$

Rounding this value to two decimal places gives a final reported value of 0.53 g/cc.

9.2 RSD=(R1−R2)×100/R1
where: RSD=Relative Standard Deviation (%)
R1 & R2=Result of individual repeat (g/cc)
9.3 SR=R×100/V
where:
SR=Standard Recovery (%)
R=Result for Reference Standard (g/cc)
V=Historical average for standard (g/cc)

EXAMPLES

Example 1

A number of batches of LCH and LDOC were produced as generally described herein. Specifically, lanthanum carbonate hydroxide (LCH) was produced by reacting lanthanum chloride and ammonium carbonate in a continuous drip-fed reaction. The amount of lanthanum chloride was provided at a fixed rate and the amount of ammonium carbonate was variably fed. These solutions were fed into a volume of temperature controlled and mixing controlled water. The pH was kept close to constant during the reaction and the concentration of the resulting precipitate was controlled by adjusting the weight ratio of the lanthanum chloride provided to the reactor water volume. The total reactant volumes were fed over a four hour period and the temperature was controlled manually. The working volume was about 15 liters. pH automatically controls the flow of ammonium carbonate and kept close to constant during the reaction. Once a precipitate is formed, it was washed and filtered to remove the reaction salt which, in this case, should be ammonium chloride. This was accomplished using a laboratory Buchner (vacuum) filtration apparatus. The LCH was filtered and resuspended in water and refiltered until a desired suspension conductivity (indicating salt content) was reached. The LCH was then filtered a final time to increase the solid loading for drying. Drying was achieved according to a method in which the LCH filter cake (typically 40 to 60 percent solids by weight) was loaded into pyrex trays and heated in a natural convection drying oven for a minimum of 16 hours at 110 Degrees C. Thereafter, the material was dry milled and pulverized in a cone-mill (Fritz Mill) through a 0.6 millimeter mesh screen. The course powder was designated as Renazorb 013 (RZB-013).

Thermal treatment occurred by placing Renazorb-013 in alumina ($Al_2O_3$, 99.8%, high density) open-top trays and treating in an alumina-lined muffle furnace under a 3 hour ramp to 550 degrees C., a 2.5 hour soak at that temperature and a minimum 8 hour cool back to room temperature. The furnace discharge is LDOC and is designated below as Renazorb-014 (RZB-014).

Two blocks of experiments were run testing different reaction conditions. The first block of experiments used similar pH, temperature, and concentration conditions found favorable to produce Renazorb-011. Specifically these conditions targeted a pH of 6.0, a temperature of 85 Degrees C., and a final precipitate concentration of 43.5 g/L. These conditions were held constant and several batches were produced to determine the repeatability of the resulting RZB-013 and RZB-014 compounds. The second block of experiments examined the effects of varying the reaction pH, temperature, and precipitate concentration on the RZB-013 and RZB-014 compounds according to the design shown in Table 4.

TABLE 4

| Experimental Design | | | |
|---|---|---|---|
| Batch ID | Average Reaction Temp. (° C.) | Average Reaction pH | Product Concentration (g/L), Theoretical |
| Modified Experimental Design | | | |
| 101008 | 75.0 | 5.50 | 36.0 |
| 102308 | 75.0 | 5.50 | 36 0 |
| 101408 | 75.0 | 5.50 | 73.0 |
| 102208 | 75.0 | 5.50 | 73.0 |
| 102108 | 75.0 | 6.50 | 36.0 |
| 102708 | 75.0 | 6.50 | 36.0 |
| 101608 | 75.0 | 6.50 | 73.0 |
| 100108 | 80.0 | 6.00 | 60.0 |
| 110608 | 80.0 | 6.00 | 55.0 |
| 110708 | 80.0 | 6.00 | 55.0 |
| 102408 | 85.0 | 5.50 | 36.0 |
| 100908 | 85.0 | 5.50 | 36.0 |
| 101708 | 85.0 | 5.50 | 73.0 |
| 112608 | 85.0 | 6.00 | 20.0 |
| 100208 | 85.0 | 6.50 | 36.0 |
| 100808 | 85.0 | 6.50 | 36.0 |
| 110508 | 85.0 | 6.50 | 36.0 |
| 101308 | 85.0 | 6.50 | 73.0 |
| 112408 | 85.0 | 7.00 | 36.0 |
| 120908 | 85.0 | 7.00 | 43.5 |
| 121508 | 85.0 | 7.00 | 43.5 |
| 121608 | 85.0 | 7.00 | 43.5 |
| 110408 | 90.0 | 5.50 | 36.0 |
| 103108 | 90.0 | 6.00 | 36.0 |
| 110308 | 90.0 | 6.50 | 36.0 |
| Additional April "Repeat" Batches | | | |
| 112008 | 85.0 | 6.00 | 43.5 |
| 112108 | 85.0 | 6.00 | 43.5 |
| 120208 | 85.0 | 6.00 | 43.5 |
| 120308 | 85.0 | 6.00 | 43.5 |
| 120408 | 85.0 | 6.00 | 43.5 |
| 120508 | 85.0 | 6.00 | 43.5 |
| 120808 | 85.0 | 6.00 | 43.5 |
| 121108 | 85.0 | 6.00 | 43.5 |

For each run, both the Renazorb-013 (LCH) and the Renazorb-014 (LDOC) were characterized. Renazorb-013 is important to characterize because its features (particularly physical features such as BET-Surface-Area, Particle Size Distribution, crystalline phase by XRD, bulk density) strongly impact the same critical features of Renazorb-014. The typical characterization suite of Renazorb-013 and Renazorb-014 includes BET-Surface-Area (BET-SA), Particle Size Distribution (PSD), crystalline phase by XRD, bulk density, chloride content, lanthanum content, carbon content. On top of this Renazorb-014 is tested for phosphate binding performance (4.5 pH @30 min). Assays such as La, C, Cl are typically fairly consistent and not under scrutiny. The results of the first block of experiments, in terms of certain physical properties of LCH and LDOC, are presented in Table 5 below.

TABLE 5

| Results of First Block of Experiments Production Parameters/Observations | | | |
|---|---|---|---|
| Batch # | Average Reaction Temp. (° C.) | Average Reaction pH | Product Concentration (g/L), Theoretical |
| 040308 | 85.8 | 6.13 | 43.5 |
| 040408 | 85.6 | 6.26 | 43.5 |
| 040708 | 85.0 | 6.39 | 43.5 |
| 040808 | 85.2 | 6.27 | 43.5 |
| 040908 | 85.5 | 5.57 | 43.5 |
| 041008 | 85.3 | 6.24 | 43.5 |
| 041108 | 85.3 | 6.27 | 43.5 |
| 041408 | 87.0 | 6.12 | 43.5 |
| 041508 | 86.3 | 6.11 | 43.5 |
| 041608 | 86.4 | 5.93 | 43.5 |
| 041708 | 87.0 | 6.12 | 43.5 |

TABLE 5-continued

Results of First Block of Experiments
Production Parameters/Observations

| | | | |
|---|---|---|---|
| 041808A | 84.7 | 5.55 | 43.5 |
| 041808B | 86.2 | 6.03 | 43.5 |
| 042108 | 86.4 | 6.03 | 43.5 |
| 042208A | 86.9 | 5.10 | 43.5 |
| 042208B | 86.4 | 5.91 | 43.5 |

| Batch # | Does LCH gel during reaction? | Total Filtering Time (min) | Filter Cake Moisture (%) |
|---|---|---|---|
| 040308 | N | 160 | 42.6 |
| 040408 | N | | 42.8 |
| 040708 | N | | 43.4 |
| 040808 | N | 295.0 | 43.4 |
| 040908 | N | 140.0 | 44.1 |
| 041008 | N | 200.0 | 46.0 |
| 041108 | N | 370.0 | 42.8 |
| 041408 | N | 160.0 | 41.2 |
| 041508 | N | 235.0 | 40.3 |
| 041608 | N | 180.0 | 43.6 |
| 041708 | N | 165.0 | 44.1 |
| 041808A | N | 65.0 | 64.0 |
| 041808B | N | 150.0 | 41.4 |
| 042108 | N | 250.0 | 66.2 |
| 042208A | N | | 44.3 |
| 042208B | N | | 44.9 |

Condensed Renazorb 013 Analytical Data

| Batch # | Surface Area (m^2 g) | Bulk Density g/cc)^ | XRD Phase 1 ID | XRD Phase 2 ID |
|---|---|---|---|---|
| 040308 | 15.5 | 0.75 | 26-815 | 49-981 |
| 040408 | 49.9 | 0.78 | 26-815 | |
| 040708 | 38.9 | 0.72 | 26-815 | |
| 040808 | 24.3 | 0.49 | 26-815 | 29-512 |
| 040908 | 35.9 | 0.61 | 26-815 | |
| 041008 | 42.0 | 0.74 | 26-815 | |
| 041108 | 40.9 | 0.77 | 26-815 | |
| 041408 | 36.9 | 0.82 | 26-815 | |
| 041508 | 35.4 | 0.77 | 26-815 | |
| 041608 | 24.3 | 0.71 | 26-815 | |
| 041708 | 25.0 | 0.78 | 26-815 | |
| 041808A | 11.8 | 0.32 | 26-815 | 49-981 |
| 041808B | 35.8 | 0.74 | 26-815 | |
| 042108 | 38.4 | 0.69 | 26-815 | 49-981 |
| 042208A | 10.4 | 0.69 | 26-815 | 49-981 |
| 042208B | 22.9 | 0.70 | 26-815 | 49-981 |

Production Parameters/Observations

| Batch # | Average Reaction Temp. (° C.) | Average Reaction pH | Product Concentration (g/L), Theoretical | Does LCH gel during reaction? | Total Filtering Time (min) | Filter Cake Moisture (%) |
|---|---|---|---|---|---|---|
| 040308 | 85.8 | 6.13 | 43.5 | N | 160 | 42.6 |
| 040408 | 85.6 | 6.26 | 43.5 | N | | 42.8 |
| 040708 | 85.0 | 6.39 | 43.5 | N | | 43.4 |
| 040808 | 85.2 | 6.27 | 43.5 | N | 295.0 | 43.4 |
| 040908 | 85.5 | 5.57 | 43.5 | N | 140.0 | 44.1 |
| 041008 | 85.3 | 6.24 | 43.5 | N | 200.0 | 46.0 |
| 041108 | 85.3 | 6.27 | 43.5 | N | 370.0 | 42.8 |
| 041408 | 87.0 | 6.12 | 43.5 | N | 160.0 | 41.2 |
| 041508 | 86.3 | 6.11 | 43.5 | N | 235.0 | 40.3 |
| 041608 | 86.4 | 5.93 | 43.5 | N | 180.0 | 43.6 |
| 041708 | 87.0 | 6.12 | 43.5 | N | 165.0 | 44.1 |
| 041808A | 84.7 | 5.55 | 43.5 | N | 65.0 | 64.0 |
| 041808B | 86.2 | 6.03 | 43.5 | N | 150.0 | 41.4 |
| 042108 | 86.4 | 6.03 | 43.5 | N | 250.0 | 66.2 |
| 042208A | 86.9 | 5.10 | 43.5 | N | | 44.3 |
| 042208B | 86.4 | 5.91 | 43.5 | N | | 44.9 |

TABLE 5-continued

| Results of First Block of Experiments Production Parameters/Observations | | | | | | |
|---|---|---|---|---|---|---|
| Condensed Renazorb 014 Analytical Data | | | | | | |
| Batch # | Surface Area (m^2 g) | D5O (um) Sonicated SOP-QC-GMP-2402 | D9D(um)) Sonicated SCP-QC GMP-2402 | Bulk Density g/cc) | P04 Binding @4.5pH (rxn Comp. %) | XRD Phase 1 ID |
| 040308 | 16.8 | 28 | 79 | 0.97 | 88 | 37-804 |
| 040408 | 35.2 | 30 | 83 | 0.85 | 96 | 37-804 |
| 040708 | 31.1 | 44 | 135 | 0.95 | 88 | 37-804 |
| 040808 | 30.7 | 8 | 56 | 0.56 | 91 | 37-804 |
| 040908 | 27.4 | 15 | 62 | 0.70 | 95 | 37-804 |
| 041008 | 32.0 | 40 | 121 | 0.98 | 97 | 37-804 |
| 041108 | 33.0 | 33 | 91 | 1.02 | 79 | 37-804 |
| 041408 | 32.3 | 32 | 83 | 1.05 | 74 | 37-804 |
| 041508 | 30.2 | 42 | 128 | 0.94 | 67 | 37-804 |
| 041608 | 27.6 | 9 | 31 | 0.78 | 100 | 37-804 |
| 041708 | 25.6 | 41 | 107 | 0.98 | 81 | 37-804 |
| 041808A | 12.5 | 25 | 99 | 0.46 | 88 | 37-804 |
| 041808B | 35.3 | 35 | 95 | 0.97 | 90 | 37-804 |
| 042108 | 30.0 | 27 | 77 | 0.88 | 101 | 37-804 |
| 042208A | 13.8 | 25 | 74 | 0.60 | 89 | 37-804 |
| 042208B | 27.8 | 48 | 169 | 1.08 | 79 | 37-804 |

The majority of batches produced yielded high SA Renazorb-013 and correspondingly high SA Renazorb-014. Three of the batches from this group yielded a lower SA. Note two batches, 042208A and 042208B, were synthesized using ammonium bicarbonate base instead of ammonium carbonate, and contribute one of the low-SA materials. Two of the low SA materials have a relatively low average reaction pH, but one has a pH well within the spread of high-SA materials. It was initially thought that because of this observation, pH may have an impact on the resulting SA and thus improved pH control should be implemented, as done in the present work. The results of the second block of experiments are presented in Table 6 below.

TABLE 6

| Results of Second Block of Experiments Processing Data and Observations | | | | | |
|---|---|---|---|---|---|
| Batch # | Average Reaction Temp (° C.) | Average Reaction pH | Product Concentration (g/L) Theoretical | Does LCH Gel during Reaction? | Filter Cake Moisture (%) |
| 101008 | 75.0 | 5.50 | 36.0 | N | 85.1 |
| 102308 | 75.0 | 5.50 | 36.0 | Y | 51.0 |
| 101408 | 75.0 | 5.50 | 73.0 | Y | 81.9 |
| 102208 | 75.0 | 5.50 | 73.0 | Y | 88.3 |
| 102108 | 75.0 | 6.50 | 36.0 | Y | 83.6 |
| 102708 | 75.0 | 6.50 | 36.0 | Y | 62 4 |
| 101608 | 75.0 | 6.50 | 73.0 | N | 82.7 |
| 100108 | 80.0 | 6.00 | 60.0 | Y | 88.0 |
| 110608 | 80.0 | 6.00 | 55.0 | Y | 55.1 |
| 110708 | 80.0 | 6.00 | 55.0 | Y | 47.7 |
| 102408 | 85.0 | 5.50 | 36.0 | N | 50.8 |
| 100908 | 85.0 | 5.50 | 36 0 | N | 47.2 |
| 101708 | 85.0 | 5.50 | 73.0 | Y | 52.5 |
| 112608 | 85.0 | 6.00 | 20.0 | N | 46.9 |
| 100208 | 85.0 | 6.50 | 36.0 | N | 52.1 |
| 100808 | 85.0 | 6.50 | 36.0 | Y | 42.2 |
| 110508 | 85.0 | 6.50 | 36.0 | N | 57.4 |
| 101308 | 85.0 | 6.50 | 73.0 | Y | 47.0 |
| 112408 | 85.0 | 7.00 | 36.0 | N | 49.1 |
| 120908 | 85.0 | 7.00 | 43.5 | N | 42.0 |
| 121508 | 85.0 | 7.00 | 43.5 | N | 41.5 |
| 121608 | 85.0 | 7.00 | 43.5 | N | 74.5 |
| 110408 | 90.0 | 5.50 | 36.0 | N | 19.1 |
| 103108 | 90.0 | 6.00 | 36.0 | N | 55.7 |
| 110308 | 90.0 | 6.50 | 36.0 | N | 53.4 |
| 112008 | 85.0 | 6.00 | 43.5 | N | 85.1 |
| 112108 | 85.0 | 6.00 | 43.5 | N | 58.8 |
| 120208 | 85.0 | 6.00 | 43.5 | N | 58.1 |
| 120308 | 85.0 | 6.00 | 43.5 | N | 58.0 |
| 120408 | 85.0 | 6.00 | 43.5 | N | 69.8 |

TABLE 6-continued

Results of Second Block of Experiments
Processing Data and Observations

| | | | | | |
|---|---|---|---|---|---|
| 120508 | 85.0 | 6.00 | 43.5 | Y | 47.9 |
| 120808 | 85.0 | 6.00 | 43.5 | N | 76.2 |
| 121108 | 85.0 | 6.00 | 43.5 | N | 56.9 |
| 120108 | 85.0 | n/a | 43 5 | N | 60.8 |

Renazorb-013 Analytical Data

| Batch # | Surface Area (m^2/g) | Bulk Density (g/cc)* | XRD phase 1 ID (major phase) | XRD phase 2 |
|---|---|---|---|---|
| 101008 | 14.3 | 0.15 | 049-0981 | 026-0815 |
| 102308 | 11.7 | 0.31 | 049-0981 | 026-0815 |
| 101408 | 7.0 | 0.28 | 026-0815 | Unidentified |
| 102208 | 12.7 | 0.52 | 026-0815 | — |
| 102108 | 26.0 | 0.24 | 026-0815 | 049-0981/A |
| 102708 | 11.1 | 0.29 | 026-0815 | — |
| 101608 | — | 0.21 | — | — |
| 100108 | 14 2 | 0.60 | 026-0815 | — |
| 110608 | 34.8 | 0.58 | 026-0815 | — |
| 110708 | 17.8 | 0.68 | 026-0815 | 049-0981 |
| 102408 | 11.4 | 0.34 | 049-0981 | 026-0815 |
| 100908 | 9.8 | 0.51 | 049-0981 | — |
| 101708 | 9.9 | 0.30 | 049-0981 | 026-0815 |
| 112608 | 7.6 | 0.55 | 049-0981 | — |
| 100208 | 14.5 | 0.60 | 026-0815 | 049-0981 |
| 100808 | 43.4 | 0.74 | 026-0815 | — |
| 110508 | — | — | — | — |
| 101308 | 27.4 | 0.66 | 026-0815 | — |
| 112408 | 42.2 | 0.76 | 026-0815 | — |
| 120908 | 34.7 | 0.71 | 026-0815 | — |
| 121508 | 38.3 | 0.81 | 026-0815 | — |
| 121608 | 34.4 | 0.61 | 026-0815 | — |
| 110408 | 2.6 | 0.89 | 049-0981 | — |
| 103108 | 7.7 | 0.30 | 049-0981 | — |
| 110308 | 7.2 | 0.31 | 049-0981 | 026-0815 |
| 112008 | 28.8 | 0.57 | 026-0815 | — |
| 112108 | 41.6 | 0.58 | 026-0815 | — |
| 120208 | 59.9 | 0.81 | 026-0815 | — |
| 120308 | 18.1 | 0.36 | 026-0815 | 049-0981 |
| 120408 | 26.5 | 0.65 | 026-0815 | 049-0981 |
| 120508 | 21 4 | 0.54 | 026-0815 | 049-0981 |
| 120808 | 29.5 | 0.68 | 026-0815 | — |
| 121108 | 15 9 | 0.47 | 026-0815 | 049-0981 |
| 120108 | 7.1 | 0.53 | 026-0815 | 049-0981 |

Renazorb-014 Analytical Data

| Batch # | Surface Area (m^2/g) | D10 (um) Sonicated SOP-QC-GMP-2402 | D50 (um) Sonicated SOP-QC-GMP-2402 | D90 (um) Sonicated SOP-QC-GMP-2402 | Bulk Density (g/cc) | Po4 binding @4.5 pH (rxn comp. %) | XRD phase 1 ID (major phase) | XRD phase 2 |
|---|---|---|---|---|---|---|---|---|
| 101008 | — | — | — | — | — | — | — | — |
| 102308 | 12.0 | 1.6 | 22 | 60 | 0.41 | 89 | 037-0804 | — |
| 101408 | 20.3 | 2.3 | 8 | 27 | 0.20 | 84 | 037-0804 | 034-1494 |
| 102208 | 18.8 | 0.5 | 18 | 55 | 0.65 | 83 | 037-0804 | — |
| 102108 | 21.8 | 3.9 | 12 | 32 | 0.19 | 92 | 037-0804 | 23-0322 |
| 102708 | 15.7 | 1.5 | 4 | 32 | 0.21 | 84 | 037-0804 | 23-0322 |
| 101608 | 12.8 | 2.4 | 6 | 14 | 0.14 | 59 | 037-0804 | 23-0322 |
| 100108 | 23.5 | — | — | — | 0.71 | 90 | 037-0804 | — |
| 110608 | 29.3 | 1.4 | 4 | 31 | 0.58 | 93 | 037-0804 | — |
| 110708 | 16.7 | 7.4 | 47 | 160 | 0.77 | 80 | 037-0804 | — |
| 102408 | 12.1 | 1.9 | 23 | 60 | 0.45 | 90 | 037-0804 | — |
| 100908 | 7.6 | 2.7 | 5 | 9 | 0.43 | 39 | 037-0804 | — |
| 101708 | 16.8 | 1.5 | 13 | 56 | 0.35 | 91 | 037-0804 | 08-0477 |
| 112608 | 6.7 | 3.6 | 7 | 14 | 0.35 | 39 | 037-0804 | 023-0322 |
| 100208 | 13.9 | — | — | — | 0.76 | 86 | 037-0804 | — |
| 100808 | 29.9 | 6.8 | 47 | 114 | 0.91 | 92 | 037-0804 | — |
| 110508 | 16.7 | 6.6 | 50 | 151 | 0.56 | 92 | 037-0804 | — |
| 101308 | 23.0 | 6.4 | 45 | 134 | 0.84 | 89 | 037-0804 | — |
| 112408 | 24.7 | 8.1 | 55 | 135 | 0.97 | 92 | 037-0804 | — |
| 120908 | 25.3 | 3.9 | 36 | 100 | 0.84 | 86 | 037-0804 | — |
| 121508 | 24.4 | 12.8 | 76 | 200 | 0.95 | 87 | 037-0804 | — |
| 121608 | 21.0 | 10.0 | 55 | 145 | 0.95 | pending | 037-0804 | — |
| 110408 | 5.6 | 9.8 | 14 | 19 | 0.88 | 16 | 037-0804 | — |

TABLE 6-continued

| Results of Second Block of Experiments Processing Data and Observations | | | | | | | | | |
|---|---|---|---|---|---|---|---|---|---|
| 103108 | 8.4 | 2.3 | 4 | 9 | 0.28 | 83 | 037-0804 | 23-0322 |
| 110308 | 9.9 | 1.5 | 4 | 17 | 0.31 | 81 | 037-0804 | — |
| 112008 | 24.9 | 2.1 | 24 | 82 | 0.63 | 85 | 037-0804 | — |
| 112108 | 16.5 | 6.5 | 38 | 102 | 0.68 | 65 | 037-0804 | — |
| 120208 | 37.3 | 3.9 | 23 | 93 | 1.00 | 67 | 037-0804 | — |
| 120308 | 13.6 | 1.8 | 4 | 52 | 0.33 | 85 | 037-0804 | — |
| 120408 | 27.3 | 4.1 | 32 | 93 | 0.64 | 95 | 037-0804 | 023-0322 |
| 120508 | 20.2 | 3.9 | 30 | 82 | 0.66 | 92 | 037-0804 | — |
| 120808 | 22.8 | 5.9 | 31 | 80 | 0.95 | 66 | 037-0804 | — |
| 121108 | 13.9 | — | — | — | — | — | 037-0804 | 023-0320 |
| 120108 | 7.8 | 2.3 | 9 | 109 | 0.25 | 85 | 037-0804 | — |

The same equipment was used for all lots. As indicated, some parameters were deliberately adjusted (reaction temp, pH, conc.) but the remaining processes and equipment were maintained as consistently as possible with the level of instrumentation/control contained in the process.

Table 7 below demonstrates the variability that was observed in these tests. Thus while certain conclusions may fairly be drawn, inconsistencies in these data still indicate that additional variables may play a role in controlling the desirable properties of LCH and LDOC.

TABLE 7

Variability in Characteristics

Processing Data and Observations

| Batch # | Average Reaction Temp (° C.) | Average Reaction pH | Product Concentration (g/L), theoretical | Does LCH gel during reaction? | Filter Cake Moisture (%) |
|---|---|---|---|---|---|
| 102108 | 75.0 | 6.50 | 36.0 | Y | 83.6 |
| 102708 | 75.0 | 6.50 | 36.0 | Y | 62.4 |
| 110608 | 80.0 | 6.0 | 55.0 | Y | 55.1 |
| 110708 | 80.0 | 6.0 | 55.0 | Y | 47.7 |
| 100208 | 85.0 | 6.50 | 36.0 | N | 52.1 |
| 100808 | 85.0 | 6.50 | 36.0 | Y | 42.2 |
| 112008 | 85.0 | 6.00 | 43.5 | N | 85.1 |
| 112108 | 85.0 | 6.0 | 43.5 | N | 58.8 |
| 120208 | 85.0 | 6.00 | 43.5 | N | 58.1 |
| 120408 | 85.0 | 6.00 | 43.5 | N | 69.8 |
| 120508 | 85.0 | 6.00 | 43.5 | Y | 47.9 |
| 120808 | 85.0 | 6.00 | 43.5 | N | 76.2 |

Renazorb-013 Analytical Data

| Batch # | Surface Area (m^2/g) | Bulk Density (g/cc)* | XRD phase 1 ID (major phase) | XRD phase 2 |
|---|---|---|---|---|
| 102108 | 26.0 | 0.24 | 026-0815 | 19-0981 + un |
| 102708 | 11.1 | 0.29 | 026-0815 | Unidentified |
| 110608 | 34.8 | 0.58 | 026-0815 | 049-0981 |
| 110708 | 17.8 | 0.68 | 026-0815 | 094-0981 |
| 100208 | 14.5 | 0.60 | 026-0815 | |
| 100808 | 43.4 | 0.74 | 026-0815 | |
| 112008 | 20.78 | 0.57 | 026-0815 | |
| 112108 | 41.59 | 0.58 | 026-0815 | |
| 120208 | 59.91 | 0.81 | 026-0815 | |
| 120408 | 26.53 | 0.65 | 026-0815 | 049-0981 |
| 120508 | 21.40 | 0.54 | 026-0815 | 094-0981 |
| 120808 | 29.51 | 0.68 | 026-0815 | |

Renazorb-014 Analytical Data

| Batch # | Surface Area (m^2/g) | D10 (um) Sonicated SOP-QC-GMP-2402 | D50 (um) Sonicated SOP-QC-GMP-2402 | D90 (um) Sonicated SOP-QC-GMP-2402 | Bulk Density (g/cc) |
|---|---|---|---|---|---|
| 102108 | 21.8 | 3.9 | 12 | 32 | 0.19 |
| 102708 | 15.7 | 1.5 | 4 | 32 | 0.21 |

TABLE 7-continued

Variability in Characteristics

| | | | | | |
|---|---|---|---|---|---|
| 110608 | 29.29 | 1.4 | 4 | 31 | 1 |
| 110708 | 16.66 | 7.4 | 47 | 160 | 0.8 |
| 100208 | 13.9 | | | | 0.76 |
| 100808 | 29.9 | 6.8 | 47 | 114 | 1.42 |
| 112008 | 24.85 | 2.1 | 24 | 82 | 0.63 |
| 112108 | 16.45 | 6.5 | 38 | 102 | 0.68 |
| 120208 | 37.26 | 3.9 | 23 | 93 | 1.00 |
| 120408 | 27.34 | 4.1 | 32 | 93 | 0.64 |
| 120508 | 20.18 | | | | |
| 120808 | 22.76 | | | | 0.95 |

| Batch # | P04 binding @4.5 pH (rxn comp. %) | XRD phase 1 ID | XRD phase 2 1 |
|---|---|---|---|
| 102108 | | 037-0804 | 048-111 |
| 102708 | | 037-0804 | 23-032 |
| 110608 | | 037-0804 | |
| 110708 | | 037-0804 | |
| 100208 | 86 | 037-0804 | |
| 100808 | 92 | 037-0804 | |
| 112008 | 85 | 037-0804 | |
| 112108 | 65 | 037-0804 | |
| 120208 | 67 | 037-0804 | |
| 120408 | 95 | 037-0804 | 23-032 |
| 120508 | 92 | 037-0804 | |
| 120808 | 66 | 037-0804 | |

Example 2

An oral dosage form in the form of a swallowable table was produced using the LDOC ("RZB-014") of the present invention as provided in Table 8 below.

TABLE 8

Swallowable Oral Dosage Form of RZB-014

| Component | Function | Weight (mg/ tablet) at target level | % of each component at target level | % of API | % Low (−1) | % High (+1) |
|---|---|---|---|---|---|---|
| RZB-014 | active | 666.67 | 88.24% | — | — | — |
| Povidone | Wet binder | 38.50 | 6.82% | 5.77 | 4.80 | 6.80 |
| ProSolv (a blend of Micro-crystalline Cellulose, Silica Colloidal, Colloidal Silicon Dioxide, Silicic Acid) | Dry binder | 30.81 | 4.00% | 4.62 | 2.60 | 6.60 |

TABLE 8-continued

| Swallowable Oral Dosage Form of RZB-014 | | | | | | |
|---|---|---|---|---|---|---|
| Component | Function | Weight (mg/ tablet) at target level | % of each com-ponent at target level | % of API | % Low (−1) | % High (+1) |
| Ac-Di-Sol (croscarmellose sodium) | disintegrant | 30.81 | 4.00% | 4.62 | 2.60 | 6.60 |
| Magnesium stearate | lubricant | 2.33 | 0.30% | 0.35 | 0.15 | 0.55 |

Eight lots of dosage form were prepared. The povidone was dissolved in the same amount of purified water in each run. Briefly, the active (RZB-014) was added to a Glatt Fluid Bed granulator ("Midi-Glatt"), and the solution was sprayed at a rate of about 7 g/min. The granulation was dried for about an hour (until LOD below 2% was achieved). The granules were milled through a Comil with a #16 mesh screen. The granules were then added to a PK blender together with the Prosolv and Ac-Di-Sol and blended for 5 minutes. The magnesium stearate was added to the blender and blended for an additional 2 minutes. The granules were compressed on a mini tablet press using only 2 stations of the available 8 stations. Eight lots of tablets were compressed using 11.11 mm diameter round/standard concave tooling. Granules and tablets from each test composition were evaluated for loss on drying (LOD), size distribution, densities, compressibility, thickness, friability, hardness, average weight, disintegration time, and in vitro phosphate binding. The following is a table of the results obtained:

TABLE 9

Results for Swallowable Dosage Form of RZB-014

| S # | Parameter | Run 1 | Run 2 | Run 3 | Run 4 | Run 5 |
|---|---|---|---|---|---|---|
| 1 | Loss on Drying of Granules (%) | 1.82 | 1.72 | 1.38 | 1.83 | 1.13 |
| 2 | Sieve Analysis of Granules Using #20, #30, #40, #50, #60 and #80 sieves | | | | | |
| | Mean Size (mm) | 0.298 | 0.275 | 0.289 | 0.290 | 0.286 |
| 3 | Bulk Density of Granules (g/cc) | 1.1360 | 1.1060 | 1.0720 | 1.0940 | 1.1100 |
| 4 | Tap Density of Granules (g/cc) | 1.3209 | 1.3654 | 1.2916 | 1.3340 | 1.3537 |
| 5 | Compressibility of Granules (%) | 14.00 | 19.00 | 17.00 | 17.99 | 18.00 |
| 6 | Flow of Granules | | | | | |
| | Funnel-without Lubrication | Poor | Poor | Poor | Good | Poor |
| | Funnel-with Lubrication | Poor | Poor | Good | Good | Good |
| | Hopper-with Lubrication | Good | Good | Good | Good | Good |
| 7 | Tablet Thickness (mm) | 4.88 ± 0.01 | 4.9 ± 0.01 | 5.18 ± 0.01 | 5.21 ± 0.01 | 5.21 ± 0.01 |
| 8 | Tablet Friability (%) | 0.162 | 0.013 | 0.141 | 0.013 | 0.091 |
| 9 | Tablet Hardness (kp) | 8.00 ± 0.33 | 7.70 ± 0.50 | 7.83 ± 0.39 | 8.53 ± 0.37 | 7.10 ± 0.41 |
| 10 | Average weight of Tablets (mg) | 732.7 ± 10.68 | 754.1 ± 4.94 | 777.1 ± 6.35 | 785.4 ± 4.68 | 769.5 ± 11.56 |
| 11 | Tablet Disintegration Time (Seconds) | 8.33 ± .82 | 20.00 ± 1.26 | 15.50 ± 1.22 | 13.33 ± 1.03 | 12.83 ± 0.41 |
| 12 | Phosphate Binding of Tablets in 15 minutes (%) | 63.39 ± 1.93 | 82.79 ± 8.87 | 87.79 ± 6.06 | 60.85 ± 5.46 | 72.90 ± 2.51 |

| S # | Parameter | Run 6 | Run 7 | Run 8 |
|---|---|---|---|---|
| 1 | Loss on Drying of Granules (%) | 1.17 | 1.07 | 1.91 |
| 2 | Sieve Analysis of Granules Using #20, #30, #40, #50, #60 and #80 sieves | | | |
| | Mean Size (mm) | 0.288 | 0.274 | 0.284 |
| 3 | Bulk Density of Granules (g/cc) | 1.1170 | 1.0900 | 1.1820 |
| 4 | Tap Density of Granules (g/cc) | 1.3458 | 1.2960 | 1.4071 |
| 5 | Compressibility of Granules (%) | 17.00 | 15.90 | 16.00 |
| 6 | Flow of Granules | | | |
| | Funnel-without Lubrication | Poor | Poor | Poor |
| | Funnel-with Lubrication | Good | Good | Good |
| | Hopper-with Lubrication | Good | Good | Good |
| 7 | Tablet Thickness (mm) | 5.17 ± 0.01 | 5.36 ± 0.01 | 5.38 ± 0.01 |
| 8 | Tablet Friability (%) | 0.013 | 0.076 | 0.024 |
| 9 | Tablet Hardness (kp) | 6.13 ± 0.47 | 7.47 ± 0.50 | 7.93 ± 0.30 |

TABLE 9-continued

| Results for Swallowable Dosage Form of RZB-014 | | | | |
|---|---|---|---|---|
| 10 | Average weight of Tablets (mg) | 772.1 ± 5.50 | 786.2 ± 7.53 | 825.2 ± 5.62 |
| 11 | Tablet Disintegration Time (Seconds) | 10.17 ± 0.41 | 11.00 ± 0.00 | 16.00 ± 0.00 |
| 12 | Phosphate Binding of Tablets in 15 minutes (%) | 61.43 ± 5.56 | 67.83 ± 7.77 | 80.35 ± 4.58 |

Example 3

Additional formulations in the form of chewable tablets, sprinkle powders/granules and suspensions comprising RZB-014 were prepared.

Specifically, three chewable tablet formulations (FS-22, FS-30 and FS-31) containing 500 mg of RZB-014 (referred to hereinbelow as "SPI-014"); two sprinkle (capsule) formulations (SP-11 and SP-12) containing 500 mg of SPI-014 were formulated, and two oral suspension formulations (S-2 and S-7) containing 100 mg/mL or 500 mg/5 mL of SPI-014 were formulated. Materials used in formulations are listed below.

TABLE 10

| Materials |
|---|
| Material |
| SPI-014 (Lanthanum dioxycarbonate) |
| Lactose Monohydrate and Povidone, NF (Ludipress LCE) |
| Microcrystalline Cellulose, NF |
| Microcrystalline Cellulose and Guar gum, NF (Avicel CE-15) |
| Microcrystalline Cellulose and Sodium Carboxymethyl cellulose (Avicel RC-591) |
| Croscarmellose Sodium, USP/NF |
| Hydroxypropyl Cellulose NF |
| Polysorbate 80, NF |
| Magnesium stearate, NF |
| Colloidal Silicone Dioxide, NF |
| Purified water, USP |
| Sodium Alginate, NF |
| Carnauba Wax, |
| Glyceryl Behenate, NF |
| Povidone, USP |
| Magnesium Stearate, NF |
| Silicified Microcrystalline Cellulose NF, |
| Aspartame, NF |
| Peppermint Oil, NF |
| Poloxamer 188, NF |
| Opadry, White YS-1-18027-A |

TABLE 10-continued

| Materials |
|---|
| Material |
| Carbopol 974 P NF |
| Hypromellose, USP |
| Sodium Carboxy Methyl Cellulose, 7H4F |
| Methyl Cellulose, NF |
| Propyl Paraben, NF |
| Methyl Paraben, NF |
| Disacharin Sodium, USP |
| Sorbic Acid, NF |

I. Chewable Tablets:

Chewable tablets using various combinations of diluents and SPI-014 API were formulated by using direct compression and roller compaction. The target was to identify compositions that show disintegration time of 5-30 minutes.

Direct Compression Process: Various quantities of the SPI-014 API, diluents, binders, disintegrants, and lubricants were blended manually. Blends that showed good or moderate flow properties were compressed using round beveled edged punches with 14 mm diameter. The tablets were evaluated for average weight, thickness, hardness, friability and disintegration time in purified water (37° C.). Table 11 provided below includes formulation compositions, and observations.

Roller Compaction: Various quantities of the SPI-014 API and excipients were roller compacted using a TFC-LAB MICRO Roller Compactor under 2 tons roller pressure, 2 rpm roller speed, and 15 rpm feed screw speed. The sheets were granulated and passed through US screen #16. The granules were externally/internally mixed with diluents, binders and lubricants, and tested for the flow properties. The granules were compressed using round beveled edged punches with 14 mm or 16 mm diameter. The tablets were evaluated for average weight, thickness, hardness, friability and disintegration time in purified water (37° C.). Table 12 provided below shows formulation compositions and observations. Selected compositions were prepared with flavoring agent and sweetener. Table 13A and 13B list the formulation compositions.

TABLE 11

SPI-014 Chewable Tablets, 500 mg - Formulation Compositions Prepared by Direct Compression Process

| | | Quantity (mg/unit) | | | | | | |
|---|---|---|---|---|---|---|---|---|
| S # | Ingredients | FS-1 | FS-2 | FS-3 | FS-4 | FS-5 | FS-6 | FS-7 |
| 1 | SPI-014 | 666.7 | 666.7 | 666.7 | 666.7 | 666.7 | 666.7 | 666.7 |
| 2 | Microcrystalline cellulose and guar gum | 248.3 | 248.3 | — | — | — | — | 448.3 |
| 3 | Lactose monohydrate and Povidone, | — | — | 248.3 | 248.3 | — | — | — |
| 4 | Sodium Alginate | — | — | — | — | 248.3 | 248.3 | — |
| 5 | Hydroxy propyl cellulose | — | — | — | — | — | — | — |

TABLE 11-continued

SPI-014 Chewable Tablets, 500 mg - Formulation Compositions Prepared by Direct Compression Process

| | | | | | | | | |
|---|---|---|---|---|---|---|---|---|
| 6 | Carnauba Wax | — | — | — | — | — | — | — |
| 7 | Glyceryl Behenate | — | — | — | — | — | — | — |
| 8 | Polyvinyl Pyrolidone | 40.0 | 40.0 | 40.0 | 40.0 | 40.0 | 40.0 | 40.0 |
| 9 | Croscarmellose sodium | 40.0 | | 40.0 | — | 40.0 | — | — |
| 10 | Magnesium Stearate | 5.0 | 5.0 | 5.0 | 5.0 | 5.0 | 5.0 | 5.0 |
| | Total | 1000.0 | 960.0 | 1000.0 | 960.0 | 1000.0 | 960.0 | 1160.0 |
| | Observations | | | | | | | |
| 1 | Flow of the blend through funnel | Good | Good | Moderate | = | Poor | Poor | Poor |
| 2 | Average weight (g) (n = 10) | 0.986 ± 0.013 | 0.992 ± 0.017 | 1.007 ± 0.010 | 0.997 ± 0.014 | — | — | — |
| 3 | Thickness (mm) | 3.91 | 3.75 | 3.99 | 3.78 | — | — | — |
| 4 | Friability (% w/w) | 0.18 | 0.22 | 0.16 | 0.14 | — | — | — |
| 5 | Hardness (kp) | 8.4 | 8.0 | 10.2 | 9.8 | — | — | — |
| 6 | Disintegration time (Minutes) | 1 | 2 | 1 | 1 | — | — | — |

| S # | Ingredients | FS-8 | FS-9 | FS-10 | FS-11 | FS-12 | FS-13 |
|---|---|---|---|---|---|---|---|
| 1 | SPI-014 | 666.7 | 666.7 | 666.7 | 666.7 | 666.7 | 666.7 |
| 2 | Microcrystalline cellulose and guar gum | — | — | — | — | 100 | 164.15 |
| 3 | Lactose monohydrate and Povidone, | — | — | — | — | — | — |
| 4 | Sodium Alginate | — | — | — | — | — | — |
| 5 | Hydroxy propyl cellulose | — | 288.3 | — | — | 228.3 | 164.15 |
| 6 | Carnauba Wax | — | — | 293.3 | — | — | — |
| 7 | Glyceryl Behenate | — | — | — | 293.3 | — | — |
| 8 | Polyvinyl Pyrolidone | 288.3 | — | — | — | — | — |
| 9 | Croscarmellose sodium | — | — | — | — | — | — |
| 10 | Magnesium Stearate | 5.0 | 5.0 | — | — | 5.0 | 5.0 |
| | Total | 960.0 | 960.0 | 960.0 | 960.0 | 1000.0 | 1000.0 |
| | Observations | | | | | | |
| 1 | Flow of the blend through funnel | Poor | Good | Good | Moderate | Moderate | Moderate |
| 2 | Average weight (g) (n = 10) | — | 0.998 ± 0.005 | 0.989 ± 0.013 | 0.999 ± 0.010 | 1.013 ± 0.011 | 1.002 ± 0.001 |
| 3 | Thickness (mm) | — | 4.34 | 4.16 | 4.27 | 4.24 | 3.89 |
| 4 | Friability (% w/w) | — | 0.27 | 0.39 | 0.21 | 0.11 | 0.17 |
| 5 | Hardness (kp) | — | 4.8 | 4.1 | 5.2 | 8.2 | 8.4 |
| 6 | Disintegration time (Minutes) | — | >45 | >45 | >45 | >45 | 3 |

TABLE 12

A: SPI-014 Formulation Compositions Prepared by Roller Compaction Chewable Tablets, 500 mg -

| | | Quantity (mg/unit) | | | | | |
|---|---|---|---|---|---|---|---|
| # | Ingredients | FS-14 | FS-15 | FS-16 | FS-17 | FS-18 | FS-19 |
| 1 | SPI-014 | 666.7 | 666.7 | 666.7 | 666.7 | 666.7 | 666.7 |
| 2 | Microcrystalline cellulose and guar gum | 109.43 | 218.87 | 109.43 | 164.15 | 218.87 | 500 |

TABLE 12-continued

| | | | | | | | |
|---|---|---|---|---|---|---|---|
| 3 | Microcrystalline cellulose | — | — | — | — | — | — |
| 4 | Silicified Microcrystalline Cellulose | — | — | — | — | — | — |
| 5 | Hydroxy propyl cellulose | 218.87 | 109.43 | — | — | — | — |
| 6 | Hydroxy propyl cellulose | — | — | 218.87 | 164.15 | 109.43 | — |
| 7 | Glyceryl Behenate | — | — | — | — | — | — |
| 8 | Polyvinyl Pyrolidone | — | — | — | — | — | 325.8 |
| 9 | Magnesium Stearate | 5.0 | 5.0 | 5.0 | 5.0 | 5.0 | 15.0 |
| 10 | Aspartame | — | — | — | — | — | — |
| 11 | Peppermint Oil | — | — | — | — | — | — |
| | Total | 1000.0 | 1000.0 | 1000.0 | 1000.0 | 1000.0 | 1507.5 |
| | Observations | | | | | | |
| 1 | Flow of the blend through funnel | Good | Good | Good | Good | Good | Good |
| 2 | Average weight (g) (n = 10) | 0.999 ± 0.013 | 0.994 ± 0.011 | 1.005 ± 0.022 | 0.991 ± 0.011 | 0.982 ± 0.013 | 1.519 ± 0.017 |
| 3 | Thickness (mm) | 4.18 | 4.03 | 4.34 | 4.27 | 4.28 | 5.87 |
| 4 | Friability (% w/w) | 0.34 | 0.45 | 0.19 | 0.26 | 0.21 | 0.18 |
| 5 | Hardness (kp) | 7.8 | 6.1 | 8.1 | 9.2 | 6.8 | 8.1 |
| 6 | Disintegration time (min) | >45 | >45 | >45 | >45 | >45 | >45 |

| | | Quantity (mg/unit) | | | | | | |
|---|---|---|---|---|---|---|---|---|
| S # | Ingredients | FS-20 | FS-21 | FS-22 | FS-23 | FS-24 | FS-25 | FS-26 |
| 1 | SPI-014 | 666.7 | 666.7 | 666.7 | 666.7 | 666.7 | 666.7 | 666.7 |
| 2 | Microcrystalline cellulose and guar gum | 333.2 | — | — | — | — | — | |
| 3 | Microcrystalline cellulose | 166.8 | — | — | — | — | — | — |
| 4 | Silicified Microcrystalline Cellulose | — | 818.3 | 568.3 | 683.3 | 416.65 | 683.3 | 608.3 |
| 5 | Hydroxy propyl cellulose | — | — | — | — | — | — | — |
| 6 | Hydroxy propyl cellulose | — | — | — | — | — | — | — |
| 7 | Glyceryl Behenate | — | — | — | 150 | 416.65 | 75 | 112.5 |
| 8 | Polyvinyl Pyrolidone | 318.3 | — | 225 | — | — | 75 | 112.5 |
| 9 | Magnesium Stearate | 15 | 15 | 15 | — | — | — | — |
| 10 | Aspartame | — | — | 20 | — | — | — | — |
| 11 | Peppermint Oil | — | — | 5 | — | — | — | — |
| | Total | 1500.0 | 1500.0 | 1500.0 | 1500.0 | 1500.0 | 1500.0 | 1500.0 |
| | Observations | | | | | | | |
| 1 | Flow of the blend through funnel | Good | Good | Good | Good | Good | Good | Good |
| 2 | Average weight (g) (n = 10) | 1.502 ± 0.019 | 1.492 ± 0.014 | 1.498 ± 0.013 | 1.511 ± 0.013 | 1.489 ± 0.018 | 1.492 ± 0.010 | 1.498 ± 0.014 |
| 3 | Thickness (mm) | 5.93 | 5.69 | 5.43 | 5.35 | 5.44 | 5.32 | 5.28 |
| 4 | Friability (% w/w) | 0.13 | 0.17 | 0.21 | 0.17 | 0.26 | 0.31 | 0.25 |
| 5 | Hardness (kp) | 10.3 | 19.8 | 10.4 | 9.3 | 8.2 | 8.9 | 8.9 |
| 6 | Disintegration time (min) | 1-2 | 1-2 | 13-17 | 2-3 | >45 | 1-2 | 1-2 |

B: SPI-014 Chewable Tablets, 500 mg - Formulation Compositions Prepared by Roller Compaction Process

| | | Quantity (mg)/unit | | | | |
|---|---|---|---|---|---|---|
| S. # | Ingredients | FS-27 | FS-28 | FS-29 | FS-30 (FS-29 repeat) | FS-31 |
| 1 | SPI-014 | 666.7 | 666.7 | 666.7 | 666.7 | 666.7 |
| 2 | Microcrystalline cellulose and guar gum | — | — | — | — | 558.0 |
| 3 | Microcrystalline cellulose | — | — | 787.3 | 762.3 | — |

TABLE 12-continued

| | | | | | | |
|---|---|---|---|---|---|---|
| 4 | Silicified Microcrystalline Cellulose | 533.3 | 578.3 | — | — | — |
| 5 | Poloxamer 188 | — | — | 30.5 | 15.5 | — |
| 6 | Glyceryl Behenate, | 150.0 | 127.5 | 15.5 | 30.5 | — |
| 7 | Polyvinyl Pyrolidone, | 150.0 | 127.5 | — | — | 235.3 |
| 8 | Magnesium Stearate | — | — | — | — | 15.0 |
| 9 | Aspartame | — | — | — | 20.0 | 20.0 |
| 10 | Peppermint Oil | — | — | — | 5.0 | 5.0 |
| | Total | 1500.0 | 1500.0 | 1500.0 | 1500.0 | 1500.0 |
| | | | Observations | | | |
| 1 | Flow of the blend through funnel | Good | Good | Good | Good | Good |
| 2 | Average weight (g) (n = 10) | 1.516 ± 0.012 | 1.507 ± 0.011 | 1.481 ± 0.010 | 1.494 ± 0.013 | 1.482 ± 0.015 |
| 3 | Thickness (mm) (n = 10) | 5.51 | 5.56 | 5.32 | 5.17 | 5.24 |
| 4 | Friability (% w/w) | 0.34 | 0.28 | 0.21 | 0.32 | 0.23 |
| 5 | Hardness (kp) | 14.8 | 8.4 | 10.8 | 11.7 | 7.9 |
| 6 | Disintegration time (min) | 27-32 | 8-10 | 22-24 | 14-18 | 10-14 |

Results:

Three prototype compositions (FS-22, FS-30 and FS-31) showed good flow characteristics and expected disintegration time (5-30 minutes). Other compositions showed either fast (<5 minutes) or slow (>45 minutes) disintegration. The SPI-014 (Lanthanum) contents of these compositions were as follows:

Chewable Tablets Composition FS-22: 474.4 mg/tablet.

Chewable Tablets Composition FS-30: 501.4 mg/tablet.

Chewable Tablets Composition FS-31: 487.0 mg/tablet.

II. Sprinkle Oral Powder or Granules:

Sprinkles are capsule or sachet dosage forms, where the entire contents (powders/granules) are sprinkled onto food before ingestion. Sprinkle dosages provide a benefit to patients who have difficulty in swallowing solid dosage forms. Such dosage forms are familiar to one of skill in the art.

Dry Granulation/Roller compaction Process: Various quantities of the SPI-014 and selected dry binders were roller compacted using TFC-LAB MICRO Roller Compactor under 2 tons roller pressure, 2 rpm roller speed, and 15 rpm feed screw speed. The sheets were passed through US screen #16, and evaluated for the uniformity of the particle size. Table 13 provided below shows formulation compositions.

Spray Granulation Process: SPI-014 was loaded onto a MidiGlatt fluid bed processor, and sprayed with selected granulating liquids, according to normal operating conditions. Table 13 shows formulation compositions.

Wet Granulation Process: As provided in the formulation compositions disclosed in Table 13, various quantities of SPI-014 were granulated with the binder solution (such as 10% w/v of Opadry or Klucel—LF) in a planetary mixer. The wet mass was tray dried at 60° C. until the LOD reaches below 3% w/w. It was then passed though sieve #14, evaluated for the size uniformity by visual observations, and filled in gelatin capsules (size '00').

TABLE 13

SPI-014 Sprinkles, 500 mg - Formulation Compositions

| | | Quantity (mg)/unit | | | |
|---|---|---|---|---|---|
| S. # | Ingredients | SP-1 | SP-2 | SP-3 | SP-4 |
| 1 | SPI-014 | 666.7 | 666.7 | 666.7 | 666.7 |
| 2 | Microcrystalline cellulose and guar gum | 666.7 | — | — | — |

TABLE 13-continued

SPI-014 Sprinkles, 500 mg - Formulation Compositions

| | | | | | |
|---|---|---|---|---|---|
| 3 | Lactose Monohydrate and Povidone | — | 666.7 | — | — |
| 4 | Sodium Alginate | — | — | 666.7 | — |
| 7 | Hydroxy propyl cellulose | — | — | — | 666.7 |
| 10 | Microcrystalline cellulose | — | — | — | — |
| 11 | Hydroxy propyl cellulose (Klucel-HF) | — | — | — | — |
| 12 | Hydroxy propyl cellulose (Klucel-LF) | — | — | — | — |
| 13 | Opadry | — | — | — | — |
| | Total | 1333.4 | 1333.4 | 1333.4 | 1333.4 |
| | Process | Roller compaction (Dry granulation) | | | |
| | Uniformity in Size | More fines/less granules | | | |

| S. # | Ingredients | SP-5 | SP-6 | SP-7 | SP-8 | SP-9 | SP-10 |
|---|---|---|---|---|---|---|---|
| 1 | SPI-014 | 666.7 | 666.7 | 666.7 | 666.7 | 666.7 | 666.7 |
| 2 | Micro-crystalline cellulose and guar gum (Avicel CE-15) | — | — | — | — | — | — |
| 3 | Lactose Monohydrate and Povidone | — | — | — | — | — | — |
| 4 | Sodium Alginate | — | — | — | — | — | — |
| 7 | Hydroxy propyl cellulose | — | — | — | — | — | — |
| 10 | Micro-crystalline cellulose | 666.7 | — | — | — | — | — |
| 11 | Hydroxy propyl cellulose | — | 666.7 | — | — | — | — |
| 12 | Hydroxy propyl cellulose | — | — | 666.7 | — | — | 66.7 |

TABLE 13-continued

| SPI-014 Sprinkles, 500 mg - Formulation Compositions | | | | | | | |
|---|---|---|---|---|---|---|---|
| 13 | Opadry | — | — | — | 66.7 | 133.4 | — |
| | Total | 1333.4 | 1333.4 | 1333.3 | 733.4 | 800.1 | 733.4 |
| | Process | Spray Granulation | | | | | |
| | Uniformity in Size | More fines/less granules | | | | | |

| S. # | Ingredients | SP-11 | SP-12 |
|---|---|---|---|
| 1 | SPI-014 | 666.7 | 666.7 |
| 2 | Microcrystalline cellulose and guar gum(Avicel CE-15) | — | — |
| 3 | Lactose Monohydrate and Povidone | — | — |
| 4 | Sodium Alginate | — | — |
| 7 | Hydroxy propyl cellulose | — | — |
| 10 | Microcrystalline cellulose | — | — |
| 11 | Hydroxy propyl cellulose | — | — |
| 12 | Hydroxy propyl cellulose | — | 66.7 |
| 13 | Opadry | 133.4 | — |
| Total | | 800.1 | 733.4 |
| Process | | Wet granulation | |
| Uniformity in Size | | Uniform granules | |

Results: Two prototype compositions (SP-10 and SP-11) yielded uniform granules, and showed good flow characteristics. The SPI-014 (Lanthanum) contents of these compositions were as follows:

Sprinkle (Capsule) Composition SP-10: 537.5 mg/capsule;

Sprinkle (Capsule) Composition SP-11: 510.2 mg/capsule.

III. Suspensions:

Suspensions are homogeneous mixtures containing an insoluble solid dispersed in a liquid with the aid of a suspending agent and are familiar to one of skill in the art. Although suspensions are thermodynamically unstable systems and undergo phase separation/sedimentation over time, an ideal suspension will be dispersed uniformly when mixed.

Suspensions comprising SPI-014 API, and selected suspending agents, sweeteners, flavors, and preservatives were formulated as shown in Table 14. The suspending agent was dissolved in about 50% of water using a overhead stirrer. SPI-014 was added into about 30% of water and homogenized. The drug suspension was added into the solution of suspending agent, and mixed for 30 minutes. The remaining constituents were added, and the volume was made up to 100% with water.

Compositions that formed uniform suspensions were evaluated for the microscopic examination, density, and sedimentation for 7 days.

TABLE 14

SPI-014 Suspensions, 500 mg/5 mL - Formulation Compositions

| | Quantities Used (%) | | | | | | |
|---|---|---|---|---|---|---|---|
| Ingredients | S1 | S2 | S3 | S4 | S5 | S6 | S7 |
| SPI-014 | 13.334 | 13.334 | 13.334 | 13.334 | 13.334 | 13.334 | 13.334 |
| Micro-crystalline Cellulose and Sodium CMC | 1.500 | 1.500 | | | | | |
| Carbopol 934 NF | | | 0.600 | | | | |
| Hypro-mellose | | | | 1.000 | | | |
| Hydroxy propyl cellulose | | | | | 4.000 | | |
| Sodium Carboxy Methyl Cellulose | | | | | | 0.500 | |
| Methyl Cellulose | | | | | | | 1.000 |
| Propyl Paraben | 0.020 | | | 0.020 | 0.020 | | |
| Methyl Paraben | 0.200 | | | 0.200 | 0.200 | | |
| Disacharin Sodium | 0.150 | 0.150 | | 0.150 | 0.150 | 0.150 | 0.150 |
| Polysorbate 80 | 0.100 | 0.100 | | 0.100 | 0.100 | 0.100 | 0.100 |
| Sorbic Acid | | 0.050 | | | | 0.100 | 0.050 |
| Flavoring Agent | | 0.100 | | 0.100 | 0.100 | | 0.100 |
| Purified Water Q.S. | 100.000 | 100.000 | 100.000 | 100.000 | 100.000 | 100.000 | 100.000 |

Results: Compositions S2, S4 and S7 formed uniform suspensions, and therefore were evaluated for physical stability for 7 days. The densities of these two formulations were 1.09, and 1.07 g/mL, respectively. The SPI-014 (Lanthanum) content of these compositions were as follows:

Suspension Composition S2: 91.9 mg/mL;

Suspension Composition S7: 98.2 mg/mL.

Example 4

An analytical test method for the determination of phosphate binding capacity of lanthanum carbonate drug substance (DS) and drug products (DP) in pH 4.5 buffer using an ion chromatography system is provided in detail below.

Specifically, the scope of the study provided herein is to determine the phosphate binding kinetics/capacity of lanthanum carbonate drug substance (DS) and drug product (DP) in acetate buffer solutions containing a known amount of dissolved phosphate at pH=4.5 using the USP Dissolution Apparatus and determined by Ion Chromatography System.

Briefly, phosphate content is determined using the IC (Ion Chromatography) System equipped with conductivity detector, and the quantitation is achieved by comparing the response of the unknown sample against the external calibration curve. The samples are filter and inject directly thru the system.

Required Materials:

Reagents:

Phosphorus IC Standard, NIST-traceable, 1000 ppm;

Ultrapure Deionized (DI) water, 18.2 MΩ;

pH buffers 4, 7 and 10 (for standardizing pH meter);

Glacial Acetic Acid, ACS grade;

Sodium Hydroxide, ACS grade;

Phosphoric Acid, ACS grade.

IC System

Dionex ICS-3000 System

Conductivity Detector;

Autosampler: capable of injecting 10 μL;

Pump: capable of a flow of 1.2 mL/min;

Data System: Chromeleon 7;

Analytical Column: Dionex Ion®Pac AS11, 4 mm×250 mm, P/N: 044076;

Pre-column: Dionex Ion®Pac AG11, 4 mm×50 mm, P/N 044078;

Eluent Generator: EG Cartridge KOH;

Ion chromatography autosampler vials and caps.

Preparation of Linearity Standard Solutions:

Prepare the following solutions using NIST Traceable Phosphorus Standard 1000 mg/L as provided in Table 15 below:

TABLE 15

Phosphorus Linearity Standards

| Standard | Phosphorus Concentration (mg/L)* | Volume of 1000 mg/L Phosphorus Standard | Final dilution volume with diluent |
|---|---|---|---|
| 1 | 50 | 2.5 | 50 |
| 2 | 100 | 5.0 | 50 |
| 3 | 200 | 10.0 | 50 |
| 4 | 250 | 12.5 | 50 |
| 5 | 300 | 15.0 | 50 |

*Calculate the concentration base on the purity stated in the Certificate of Analysis (CofA).

Phosphate Reaction Solution (0.5 M Acetate Buffer, pH 4.5): Add the following quantity of the components in the order listed in Table 16 below:

TABLE 16

Phosphate Reaction Solution (0.5 M Acetate Buffer, pH 4.5)

| No. | Component | Quantity (mL) |
|---|---|---|
| 1 | Water | 4286 |
| 2 | Acetic Acid Solution (5.0M) | 600 |
| 3 | Phosphoric Acid Stock Solution (1.62M $H_3PO_4$) | 30 |
| 4 | 50% Sodium Hydroxide solution | 94 |
| 5 | 4% Sodium Hydroxide solution | approx. 160 |
| 6 | Adjust the pH of the solution to 4.5 by adding 4% Sodium Hydroxide. Fill the volume of the container with water. | |
| 7 | Total Volume | 6000 |

Test Samples

Weight of the Drug Substance (DS) needed for testing: Calculate the weight of the API (Lanthanum Dioxycarbonate Anhydrous, $La_2O_2CO_3$) equivalent to 1.0 g of Lanthanum based on the % La content of the DS provided in the Certificate of Analysis (CofA).

Weight of the Drug Product (DP) needed for testing: Weigh individual drug product (tablet or capsule) and record the weight in the notebook. Calculate the amount (g) of elemental Lanthanum in the Drug Product based on the CofA.

Dissolution Conditions are provided as follows:

Apparatus: USP Apparatus II (Paddle);

Temperature: 37° C.±0.5° C.;

Stirring Speed: 180 RPM;

Medium: 1000 mL of Phosphate Reaction solution; (0.5M Acetate Buffer, pH 4.5);

Medium sampling: 5 mL at 0, 30, 60 and 90 minutes for Drug Substance; 5 mL at 0, 30, 60 and 90 minutes for Drug Product.

Sample Solutions: Filter the samples through 0.45 μm Acrodics PVDF membrane filter before injection.

IC Analysis

Chromatographic Conditions

The methodology for chromatographic conditions is provided below in Table 17:

TABLE 17

Methods for Chromatographic Conditions

| | | |
|---|---|---|
| Mobile Phase | DI $H_2O$ | |
| Flow Rate | 1.2 mL/min | |
| Eluent | t = 0 | Run |
| Generator | t = 0 | 5.0 mM |
| | t = 10 min | 42.0 mM |
| | t = 10.1 min | 5.0 mM |
| | t = 13 min | 5.0 mM |
| | t = 15 min | Stop run |
| Conductivity Detector | Suppressor, Cell Temp. 35° C. Type: ASRS_4 mm Current: 125 mA | |
| Column Temp. | 30° C. | |
| Autosampler Temp. | 25° C. | |
| Injection Volume | 10 μL | |

Calculations

Calculations to determine the phosphorus content are provided below:

Step 1: Phosphorus content (mg/L) $R=[A-B] \times C \div D$; where $A$=IC reading (mg/L); $B$=IC reading (mg/L) for time zero (blank); $C$=Dilution (mL); and $D$=Aliquot (mL).

Step 2: Percent Reaction Completion ($R \times N$) at $T=30$ min=$\{(R_0-R_{30}) \div (1000 \times 30.974)\} \times 100 \div M$; where $R_0$="T=0" sample results (mg/L); $R_{30}$="T=30" sample results (mg/L); 1000=Reaction Volume (mL); 30.974=Molecular weight of Phosphorus; M=moles of La initially present in the reaction; amount of La taken in (g)/138.91 molecular weight for La.

Example (with Theoretical Numbers):

$$\{(248.0-29.3)=(1000\times30.974)\}\times100\div0.0072=98\%$$

Step 3: Percent Reaction Completion ($R \times N$) at $T=60$, 90 and 120 min. Substitute the T=30 reading with T=60, T=90 and T=120, and use the same equation as that for T=30.

Step 4: Phosphate Bound per gram Lanthanum at $T=30$ min=$\{(R_0-R_{30}) \times V \times (94.974 \div 30.974)\} \div L$; where $R_0$="T=0" sample results (mg/L); $R_{30}$="T=30" sample results (mg/L); V=Volume (L) of reaction solution; 94.974=Molecular weight of Phosphate ($PO_4$); 30.974=Molecular weight of Phosphorus; and L=gram of La initially present in the reaction.

Step 5: Phosphate Bound per gram Lanthanum at T=60, 90 and 120 min. Substitute the T=30 reading with T=60, T=90 and T=120, and use the same equation as that for T=30.

Example 5

Phosphate binding data for lanthanum formulations of the present invention were determined according to the Ion Chromatography method described in Example 4. Results of such experiments are provided herein as Tables 18 and 19.

TABLE 18

Phosphate Binding Data (IC method)

| Time (min) | % reaction | mg $PO_4$/g La |
|---|---|---|
| A. FOSRENOL Chewable Tablet, Lot# A46193B | | |
| 0 | 0.0 | 0.0 |
| 30 | 16.5 | 112.9 |
| 60 | 26.1 | 178.5 |
| 90 | 40.2 | 274.7 |
| B. Formulated Chewable Tablet, Lot# FS31 | | |
| 0 | 0.0 | 0.0 |
| 30 | 28.4 | 194.4 |
| 60 | 32.9 | 224.8 |
| 90 | 46.6 | 318.6 |
| C. Formulated Sprinkle Capsule, Lot# SP12 | | |
| 0 | 0.0 | 0.0 |
| 30 | 84.7 | 578.9 |
| 60 | 93.4 | 638.6 |
| 90 | 94.4 | 645.6 |

TABLE 18-continued

Phosphate Binding Data (IC method)

| Time (min) | % reaction | mg $PO_4$/g La |
|---|---|---|
| D. Formulated Suspension, Lot# S7 | | |
| 0 | 0.0 | 0.0 |
| 30 | 38.8 | 265.3 |
| 60 | 40.0 | 273.2 |
| 90 | 35.5 | 243.0 |
| E. Formulated Suspension, Lot# S2, prep. 1 | | |
| 0 | 0.0 | 0.0 |
| 30 | 107.2 | 732.7 |
| 60 | 106.6 | 728.7 |
| 90 | 107.1 | 732.5 |
| F. Forumulated Suspension, Lot# S2, prep. 2 | | |
| 0 | 0.0 | 0.0 |
| 30 | 104.7 | 716.1 |
| 60 | 104.2 | 712.7 |
| 90 | 104.8 | 716.5 |
| G. Formulated Suspension, Lot# S2, prep. 3 | | |
| 0 | 0.0 | 0.0 |
| 30 | 104.9 | 717.2 |
| 60 | 105.5 | 721.4 |
| 90 | 105.1 | 718.3 |

TABLE 19

Phosphate binding study with Renazorb-014 swallowable tablets Lot# FSPE-20110331-1

| Time (min) | % reaction | mg $PO_4$/g La |
|---|---|---|
| 0 | 0.0 | 0.0 |
| 30 | 89.9 | 614.8 |
| 60 | 96.4 | 659.2 |
| 90 | 97.8 | 668.7 |

Example 6

The porosity of the LDOC compound referred to herein as RZB-014 was analyzed and compared to that of the LDH and LDOC compounds of the '782 patent discussed above on a Micromeritics TriStar 3000 static pressure surface area analyzer using nitrogen as the adsorbate. The Barrett, Joyner, and Halenda (BJH) method was used to calculate pore size. This method uses the Kelvin model of pore filling and applies only to the mesopore (internal width between approximately 2 and 50 nm) and small macropore size range (internal width between 50 nm and approximately 300 nm).

Results:

Data is provided hereinbelow as Table 20:

TABLE 20

Porosity Data

| | Surface Area | | | Pore volume | | | | Pore Size | |
|---|---|---|---|---|---|---|---|---|---|
| | BET | | | | | | | Adsorption | Desorption |
| Lot | Surface area ($m^2$/g) | Adsorption (cumulative) ($m^2$/g) | Desorption (cumulative) ($m^2$/g) | Total- <6.4182 nM ($cm^3$/g) | Adsorption (cumulative) ($cm^3$/g) | Desorption (cumulative) ($cm^3$/g) | Average pore width (nm) | pore diameter (nm) | pore diameter (nm) |
| RZB-14 (264317) | 25.3032 | 28.7342 | 33.8946 | 0.029726 | 0.039915 | 0.040680 | 4.69909 | 5.5584 | 4.8008 |
| RZB-14 (264314) | 32.0039 | 34.6533 | 35.5324 | 0.027236 | 0.049897 | 0.053462 | 3.40406 | 5.7595 | 6.0183 |

TABLE 20-continued

| Porosity Data | | | | | | | | | |
|---|---|---|---|---|---|---|---|---|---|
| | Surface Area | | | | | | | Pore Size | |
| | BET | | | Pore volume | | | | Adsorption | Desorption |
| Lot | Surface area ($m^2$/g) | Adsorption (cumulative) ($m^2$/g) | Desorption (cumulative) ($m^2$/g) | Total- <6.4182 nM ($cm^3$/g) | Adsorption (cumulative) ($cm^3$/g) | Desorption (cumulative) ($cm^3$/g) | Average pore width (nm) | pore diameter (nm) | pore diameter (nm) |
| RZB-12 (264316) | 6.9408 | 7.1717 | 7.3477 | 0.005344 | 0.008331 | 0.008371 | 3.07991 | 4.6467 | 4.5569 |
| RZB-11 (264315) | 13.6072 | 14.2711 | 14.5752 | 0.011198 | 0.019111 | 0.019513 | 3.29190 | 5.3566 | 5.3552 |

Results indicate that:

a) the surface areas of the two lots of RZB-14 are greater than the surface area of the LCH and LDOC compounds prepared according to the methods disclosed in U.S. Pat. No. 7,588,782 (RZB-11 & 12, respectively);

b) the LDOC compound produced according to the methods of the instant invention (both lots of RZB-14) have much higher pore volumes than RZB-12 and slightly bigger pore volume than RZB-11;

c) there is not much difference in the values of pore diameter among the LCH and LDOC compounds studied in this experiment (RZB-11, RZB-12 and both lots of RZB-14). Hence, the number of pores must be much greater in RZB-14 compared to RZB-12 and RZB-11.

With regard to phosphate binding kinetics, these data suggest that the higher volume of RZB-14 may explain higher phosphate binding of RZB-14 at 6.5 pH, as phosphate binding at higher pH is most likely limited by diffusion of phosphate into the pores.

Example 7

The morphology of LCH and LDOC compounds referred to herein as RZB-011, RZB-012 and RZB-014 were analyzed using scanning electron microscopy (SEM) according to conventional methods. See FIGS. 11-20.

Results provided herein confirm previous data which indicated that the morphologies of RZB-012 and RZB-14 are significantly different, and particularly the distinguishing spherical morphology of RZB-014 of the present invention.

Example 8

The following procedure may be used to determine the phosphate binding kinetics/capacity in solutions at a buffered pH=4.5 for lanthanum dioxycarbonate.

Briefly, a heated, acetate buffered acidic solution, adjusted to a known pH and containing a known amount of phosphate is stirred constantly throughout the test in a dissolution unit. To this stirred solution is added a known amount of lanthanum compound at time=0. At pre-specified intervals (T=30, 60 minutes) samples of the stirred slurry are taken and immediately filtered. All samples are diluted in the proper matrix and analyzed for phosphorus using an Inductively Coupled Plasma instrument equipped with an Optical Emission spectrophotometer detector (ICP-OES).

Apparatus/Equipment

Calibrated USP approved Dissolution Apparatus
Calibrated four-place analytical balance
Calibrated timer
Calibrated/Traceable thermometer (capable of 37° C.)
pH meter w/temperature compensation and appropriate probes
Magnetic stir plate
Magnetic stir bar (1" & 3" long)
Class A glass volumetric flask (10, 50, 100, 500, 1000, 2000 mL)
Class A graduated cylinders (100 to 1000 mL)
Class A volumetric glass pipettes (1 to 20 ml)
Pyrex Beakers (100, 250, 1500 mL, and ≥10 L)
10 mL & 50 mL sample tube rack
10 mL & 50 mL plastic sample tubes w/caps
20 mL plastic syringes w/plunger
0.2 μm syringe filter (20 to 25 mm diameter)
Qualified ICP-OES Reagents 1.1 Deionized water to USP <1231> (D.I.)
1.2 Certified Phosphate calibration standard (1,000 mg/L)
1.3 Secondary Solid Standard—To be taken through the entire disintegration test
1.4 Reference Standard—Same chemical as being tested with historical data
1.5 Quality Control (QC) standard—to be either and independent 1,000 or 10,000 mg/L certified AAS standard or a multi-element certified standard containing phosphorus
1.6 pH buffers (4, 4.62 or a buffer close to 4.5, 7)—Follow the manufacturers' standardization instructions. Standardize daily using pH 4 & 7 buffers and check standardization prior to beginning a new series of tests using pH 4.62 buffer. Re-standardize when standardization check is greater than ±0.05 pH units of buffer value. Report standardization & check information to the pH log book
1.7 Hydrochloric Acid (10% v/v)—In a 2 L vessel add 200 mL concentrated HCl to 1500 mL of D.I. Dilute to mark with D.I., cap and shake. Store for up to 6 months in a sealed container
1.8 Glacial Acetic Acid (5.0M HOAc)
1.8.1 In a 1500 mL beaker add a 3" magnetic stirring bar and 1 L of D.I.
1.8.2 Using a class A graduated cylinder add 572.0 mL of Glacial Acetic Acid and stir.
1.8.3 Quantitatively transfer contents to a class A 2 L volumetric flask and add D.I. to 2.0 L mark.
1.8.4 Cap and shake well to mix.
1.8.5 Transfer to a clean, labeled sealable 2 L glass vessel. Store up to 1 year.
1.9 Sodium Hydroxide (50% NaOH or 12.5N NaOH)
1.9.1 In a 500 mL Pyrex beaker add a 1" magnetic stirring bar and 250 mL of D.I. Begin stirring.
1.9.2 Weigh 250 g of NaOH pellets and transfer to the stirring beaker. CAUTION: Do not splash! Solution will heat up!

Stir until pellets have dissolved and the solution has come back down to room temperature.

1.9.3 Quantitatively transfer to a 500 mL volumetric flask and add enough D.I. so that the meniscus is approximately one inch below the 500 mL mark.

1.9.4 Cap and shake gently to mix. CAUTION: Solution will heat up! Let stand until the solution has come back down to room temperature.

1.9.5 Fill to 500 mL mark with D.I.

1.9.6 Cap and shake well to mix.

1.9.7 Transfer to a clean, labeled sealable 500 mL plastic container. Store up to 6 months.

1.10 Phosphoric Acid (1.62M H3HPO4 or 50.1 g/L P)

1.10.1 Place a 3" magnetic stir bar in the bottom of a 1.0 L Pyrex beaker and add ~600 mL of D.I. Place on a magnetic stir plate and begin stirring 1.10.2 Determine the weight of phosphoric acid required by obtaining the percent $H_3PO_4$ from the CoA and following this calculation:

1.10.2.1 $H_3PO_4$ to be weighed (g)=50.1×3.164×100÷% $H_3PO_4$ according to CoA Example: The CoA for the $H_3PO_4$ reads 85.5%. Therefore 50.1×3.164×100=85.5÷185.4 grams $H_3PO_4$ 1.10.3 Weigh the required amount of concentrated phosphoric acid into a clean Pyrex beaker.

1.10.4 Slowly and quantitatively transfer the phosphoric acid to the stirred 1.0 L Pyrex beaker containing the 600 mL D.I. Rinse the $H_3PO_4$ beaker with D.I. and add washings to the 1.0 L beaker. CAUTION: Do not splash.

1.10.5 Stir and allow solution to cool to room temperature.

1.10.6 Quantitatively transfer the solution to a 1.0 L volumetric flask.

1.10.7 Fill to 1 L mark with D.I.

1.10.8 Cap and shake well to mix.

1.10.9 Analyze this stock solution to verify phosphorus concentration:

1.10.9.1 Dilute stock 1:100 followed by a 5:100 dilution in 10% HCl matrix. The total dilution will be 1:2000 and expected concentration is 25 mg/L P.

1.10.9.2 Prepare a 10% HCl matrix standard curve of 0 and 30 mg/L P, Matrix blank, and a 20 mg/L P QC check standard using the third party certified phosphorus solution.

1.10.9.3 Analyze diluted sample, QC Standard, and Matrix Blank for phosphorus using the 213.617 nm wavelength. The standard curve of 0, 30 mg/L is linear for ICP at the 213.617 nm wavelength.

1.10.9.4 Acceptance Criteria:

1.10.9.4.1 Stock phosphate solution=50.1±1.3 g/L P.

1.10.9.4.2 Phosphorus QC check=100±2% recovery 1.10.10 Transfer approved stock phosphate solution to a clean, labeled sealable 1 L glass container. Store up to 1 year.

2.0 Procedure

Dissolution Unit & Working Phophate Solution Preparation:

2.1 Sampling will occur at T=0, 30 and 60 minutes. Determine the number of plastic sample tubes required. 3 tubes per test.

2.2 Pre-label the plastic sample tubes and place them in a rack. Cover to keep clean and set aside.

2.3 Fill adiabatic bath on the Dissolution apparatus to mark using tap water. Ready this test unit.

2.4 Set adiabatic bath temperature to 37° C.

2.5 Working Phosphate Solution (9 Liters)

2.5.1 Place a 3" stir bar at the bottom of a 10 L Pyrex beaker.

2.5.2 Using class A graduated cylinders add exactly 7000 mL of D.I., 900 mL of 5.0M HOAc and 45 mL of 1.62M $H_3PO_4$ to the 10 L Pyrex beaker. Place on a magnetic stirrer and begin stirring.

2.5.3 Carefully add 155 mL of 50% NaOH. Stir for 10 minutes before continuing to next step.

2.5.4 While stirring, with a standardized pH meter monitor the pH of the solution in the 10 L Pyrex beaker. Adjust solution to pH=4.5±0.05 using the 50% NaOH. Continue stirring for 10 minutes. If the pH=4.5±0.05 continue to next step. If not continue adjusting pH.

2.5.4.1 Record the total volume of the additional 50% NaOH additions.

2.5.5 Add the appropriate volume of D.I. using a class A graduated cylinder so that the total volume equals 9 Liters. Continue stirring for at least 10 minutes.

| | | | | |
|---|---|---|---|---|
| Example: | DI = | 7000 mL | } → | Unchanging volumes |
| 5.0M HOAc = | | 900 mL | | |
| 1.62M $H_3PO_4$ = | | 45 mL | | |
| 50% NaOH = | | 155 mL | | |
| 50% NaOH = Variable Volume | | +5 mL | → | |
| TOTAL = | | 8105 mL | | |

Therefore add: (9000 mL − 8105 mL) = 895 mL DI 2.5.5.1 Record the pH of this "working phosphate solution".

2.6 Using a class A graduated cylinder, transfer 1.0 L of the 9 L solution to each of the dissolution reaction vessels. Note that a maximum of eight tests can be performed simultaneously.

2.7 Replace cover on reaction vessel and begin stirring the reaction vessels at a rate of 180 rpm. Allow water bath and reaction vessel solutions to rise in temperature and achieve a steady 37±1° C. Verify temperature using calibrated traceable thermometer. Record observations.

T=0 SAMPLE:

2.8 Using a 20 mL syringe remove ~20 mL aliquot from each of the dissolution vessels and dispense them into properly labeled 50 mL sample tubes—one tube for each vessel. Cap tube.

2.9 Dispose of 20 mL syringe.

2.10 Add 1.33±0.003 grams of the LDOC compound at T=0. Start timer. Add LDOC at ~3 minute intervals to ensure that samples from each vessel can be pulled at the required times.

T=30 SAMPLE:

2.11 At T=30±0.25 minutes take a grab sample from each vessel using the following protocol:

2.11.1 Using a 20 mL syringe remove ~20 mL of slurry.

2.11.2 Place a 0.2 μm syringe filter firmly on the tip and dispose of the initial 2 mL.

2.11.3 With the 0.2 μm syringe filter still in place dispense remaining solution into the properly labeled 50 mL sample tube. Cap tube.

2.11.4 Dispose of syringe and 0.2 μm filter

T=60 SAMPLE:

2.12 At T=60±0.25 minutes take grab samples using the same protocol for the T=30 sample.

2.13 Determine pH of the slurry in each of the dissolution vessels. Note pH.

2.14 When test is completed, clean all glassware thoroughly and rinse with D.I. Lanthanum carbonate compounds are soluble in acid. Clean residue from glassware using dilute acid. Triple rinse with DI.

Sample Preparation:

2.15 Dilute T=0, 30 and 60 samples 1:10 and add sufficient concentrated HCl to obtain a final concentration of 10% HCl (v/v). {example: 5 mL of sample+5 mL concentrated HCL diluted with D.I. to 50 mL in a volumetric flask}

2.16 Cap, shake, and submit for analysis.

Sample Analysis:

2.17 Allow for instrument warm-up as per manufacturers' instructions 2.17.1 Prepare a "Matrix Matching" Standard Curve of 0, 30 mg/L, Matrix Blank, and QC standard (use class A volumetric glassware):

2.17.1.1 ~0.5M HOAc—Using graduated cylinder add 57.2 mL of glacial acetic acid to a 2 L volumetric flask. Dilute to volume with D.I., cap, and shake. Store any unused solution in a tightly sealed Nalgene™ container.

2.17.1.1.1 0 mg/L—In a 100 mL volumetric flask, add 10 mL of ~0.5M HOAc and 10 mL of concentrated HCl and dilute to mark with D.I. Cap and shake.

2.17.1.1.2 30 mg/L—In a 100 mL volumetric flask, add 10 mL of ~0.5M HOAc and 10 mL of concentrated HCl and 3 mL of 1000 mg/L certified phosphorous standard and dilute to mark with D.I. Cap and shake.

2.17.1.1.3 Matrix Blank—In a 100 mL volumetric flask, add 10 mL of ~0.5M HOAc and 10 mL of concentrated HCl and dilute to mark with D.I. Cap and shake.

2.17.1.1.4 20 mg/L QC Standard—In a 100 mL volumetric flask, add 10 mL of ~0.5M HOAc and 10 mL of concentrated HCl and 2 mL of INDEPENDENT 1000 mg/L certified phosphorous standard and dilute to mark with D.I.

2.17.2 Analyze diluted samples, QC Standards, and Matrix Blank for phosphorus using the 213.617 nm wavelength. The standard curve of 0, 30 mg/L is linear for ICP at the 213.617 nm wavelength.

2.17.3 Report the % Reaction Completion for T=30 and T=60.

3.0 Calculations 3.1 R=[A−B]×C÷D where: R=Result (mg/L)

A=ICP reading (mg/L)

B=ICP reading (mg/L) for matrix blank

C=Dilution (mL)

D=Aliquot (mL)

3.2

$$R \times N \text{ completion} = \frac{\{(R0 - Rt) \div (1000 \times 30.974)\} \times 100}{(W \times \text{factor} \div 138.906)}$$

where:

R0="T=0" Result (mg/L)

Rt="T=30" or "T=60" Results (mg/L)

1000=Reaction Volume (mL)

30.974=Atomic Weight of phosphorous

W=Sample Weight (g)

factor=(% La in sample)=100 (% La should be available on the Certificate of Analysis for the LDOC. If it is not, an acceptable value to use is: factor=0.7512)

138.906=Atomic Weight of Lanthanum

Example

% Reaction Completion for an LDOC Sample $$\left\{\frac{\{(248.0 - 29.3) \div (1000 \times 30.974)\} \times 100}{(1.3314 \times 0.7512 \div 138.906)} = \frac{0.7061}{0.0072} = 98\%\right\}$$

3.3 Mean (m)—Describes the technique of taking an average. Adding together the numerical values (x, y, z, etc.) of an analysis and dividing this sum by the number n of measurement yields the mean. Expressed in terms of the units of the original data.

$x=m=(x+y+z)\div n$ where:

x=m=Mean or average x,y,z=Individual measurements n=Total number of measurements m=average (a:z) (Excel Calculation)

where: m=Mean or average a:z=Represents the data range in the Excel spreadsheet 3.4 σ=$d_s$=stdev (a:z) (Excel Calculation where: σ=$d_s$=Standard deviation a:z=Represents the data range in the Excel spreadsheet 3.5% RSD=σ=m×100 where: RSD=Relative standard deviation σ=$d_s$=Standard deviation m=Mean 3.6 SR=R×100/V where: SR=Standard Recovery (%)

R=Calculated Result (% R×N Completion)

V=Accepted Value (% R×N Completion)

4.0 Quality Control 4.1 Replicates:

4.1.1 Include one repeat in the dissolution unit with every set of samples (for non-release testing analyses).

4.1.2 Run triplicates for a Release Testing (i.e. Certificate of Analysis).

4.2 Blanks:

4.2.1 Include a reagent blank in the dissolution unit with every set of samples.

4.2.2 Include a matrix blank for ICP-OES analysis. Use the ICP result obtained for this matrix blank when calculating sample results (see Calculation section).

4.3 Standards:

4.3.1 Include an In-House standard in the dissolution unit with every set of samples 4.3.2 Include a certified third party QC standard in the ICP-OES analyses. Use this to verify standard curves and instrument operation.

4.4 Acceptance Criteria:

4.4.1 Replicates should be ≤6% RSD (see Calculation section)

4.4.2 In-House Standard: % recovery should be 90 to 110% of the CoA value (see Calculation section)

4.4.3 QC Standard: % recovery should be 98 to 102% of the certified value (see Calculation section)

4.4.4 Stock Phosphate Solution must be 50.1±1.3 g/L as phosphorous. This will ensure the T=0 sample is 250±6.3 mg/L as phosphorous.

4.5 Out of Specification (OOS)—Follow in-house OOS SOP 5.0 References 5.1 See also US patent by Anormed Patent, U.S. Pat. No. 5,968,976: "Pharmaceutical composition containing selected lanthanum carbonate hydrates".

Any and all literature references, patents, patent applications or other publications disclosed herein are incorporated by reference herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of producing a lanthanum carbonate compound comprising reacting a soluble salt of lanthanum chloride with ammonium carbonate in a solvent at a reaction temperature from between about 75 degrees C. to about 90 degrees C., at a pH of from about 6.0 to 7.5, and precipitating the reaction product, wherein the reaction product is lanthanum carbonate hydroxide which includes about 0.5% by weight or less of sodium.

2. The method of claim 1 wherein the amount of lanthanum chloride relative to the amount of ammonium carbonate in the reaction ranges from between about 1:0.8 and about 1:4.

3. The method of claim 1 wherein the lanthanum carbonate hydroxide produced has a pattern matching ICDD file 26-815.

4. The method of claim 1 further comprising calcining the reaction product at a temperature between about 400 and about 700 degrees C. for at least two hours to produce lanthanum dioxycarbonate comprising one or more polymorphs of formulae $La_2O_2CO_3$ and $La_2CO_5$ and which includes about 0.75% by weight or less of sodium.

5. The method of claim 4 wherein the calcination temperature is about 550 degrees C.

6. The method of claim 4 wherein the resulting lanthanum dioxycarbonate comprises no more than about 5% by weight of the polymorph of formula $La_2CO_5$.

7. The method of claim 4 wherein the resulting lanthanum dioxycarbonate comprises no more than about 1% by weight of the polymorph of formula $La_2CO_5$.

* * * * *